United States Patent
Hogenkamp et al.

(10) Patent No.: US 6,737,418 B2
(45) Date of Patent: May 18, 2004

(54) ARYL SUBSTITUTED PYRAZOLES, IMIDAZOLES, OXAZOLES, THIAZOLES AND PYRROLES, AND THE USE THEREOF

(75) Inventors: Derk Hogenkamp, Carlsbad, CA (US); Ravindra Upasani, Foothill Ranch, CA (US); Phong Nguyen, Placentia, CA (US)

(73) Assignee: Euro-Celtique S.A. (LU)

( * ) Notice: Subject to any disclaimer, the term of this patent is extended or adjusted under 35 U.S.C. 154(b) by 0 days.

(21) Appl. No.: 10/134,697

(22) Filed: Apr. 30, 2002

(65) Prior Publication Data

US 2003/0069292 A1 Apr. 10, 2003

Related U.S. Application Data

(62) Division of application No. 09/533,864, filed on Mar. 24, 2000, now Pat. No. 6,414,011.
(60) Provisional application No. 60/126,553, filed on Mar. 26, 1999.

(51) Int. Cl.[7] ............... A61K 31/42; A61K 31/4164; C07D 233/02; C07D 263/30; C07D 277/02
(52) U.S. Cl. ............... 514/183; 514/365; 514/374; 514/396; 514/399; 548/300.1; 548/311.1; 548/333.1; 548/335.5; 548/341.5; 548/235; 548/202; 548/204; 548/205
(58) Field of Search ................... 514/183, 365, 514/374, 396, 399; 548/300.1, 311.1, 333.1, 335.5, 341.5, 235, 202, 204, 205

(56) References Cited

U.S. PATENT DOCUMENTS

| | | | |
|---|---|---|---|
| 4,072,498 A | | 2/1978 | Moon et al. ............ 71/92 |
| 4,540,648 A | | 9/1985 | Scheler ............ 430/172 |
| 4,769,062 A | | 9/1988 | Lange et al. ............ 71/90 |
| 5,104,960 A | * | 4/1992 | Inbasekaran et al. ....... 528/125 |
| 5,602,156 A | | 2/1997 | Kohn et al. ............ 514/359 |
| 5,741,818 A | | 4/1998 | Dimmock ............ 514/590 |
| 5,744,492 A | | 4/1998 | Kohn et al. ............ 514/359 |
| 6,057,346 A | | 5/2000 | Kohn et al. ............ 514/359 |

FOREIGN PATENT DOCUMENTS

| | | |
|---|---|---|
| EP | 269238 | 6/1988 |
| EP | 446180 | 9/1991 |
| HU | P905605 | 5/1993 |
| JP | 59075257 | 4/1984 |
| JP | 5287563 | 11/1993 |
| JP | 7-25849 | 1/1995 |
| JP | 7025849 | 1/1995 |
| JP | 10168063 | 6/1998 |
| WO | WO 91/00277 | 1/1991 |
| WO | WO 93/23374 | 11/1993 |
| WO | WO 96/40628 | 12/1996 |
| WO | WO 98/40364 | 9/1998 |
| WO | 9840364 | * 9/1998 |
| WO | WO 98/50348 | 11/1998 |
| WO | WO 98/52940 | 11/1998 |
| WO | WO 99/11627 | 3/1999 |
| WO | 9911634 | * 3/1999 |

OTHER PUBLICATIONS

Yamada et al, "Synthesis and Bleaching activity . . . ", CAS Abstract:118:185719–1993:185719, also cited as Biosc., Biotech.,Biochem.,56/12, 1943–8(1992).*

Anderson, W.K. et al., "Antileukemic Activity of Derivatives of 1,2–Dimethyl–3,4–bis(hydroxymethyl)–5–phenylpyrrole Bis(N–methylcarbamate)." *J. Med. Chem.* 22:977–980, American Chemical Society (1979).

Bensimon, G. et al., "A Controlled Trial of Riluzole in Amyotrophic Lateral Sclerosis," *New Engl. J. Med.* 330:585–591, Massachusetts Medical Society (1994).

Brown, C.M. et al., "Neuroprotective properties of lifarizine compared with those of other agents in a mouse model of focal cerebral ischaemia," *British J. Pharmacol.* 115:1425–1432, Stockton Press (1995).

Buchan, A.M. et al., "AMPA Antagonists: Do They Hold More Promise for Clinical Stroke Trials Than NMDA Antagonists?," *Stroke Suppl. I* 24:148–152, American Heart Association (1993).

Catterall, W.A., "Neurotoxins that Act on Voltage–Sensitive Sodium Channels in Excitable Membranes," *Ann. Rev. Pharmacol. Toxicol.* 20:15–43, Annual Reviews, Inc. (1980).

(List continued on next page.)

Primary Examiner—Mukund J. Shah
Assistant Examiner—Sudhaker B. Patel
(74) Attorney, Agent, or Firm—Sterne, Kessler, Goldstein, & Fox, P.L.L.C.

(57) ABSTRACT

This invention relates to compounds having the Formula I:

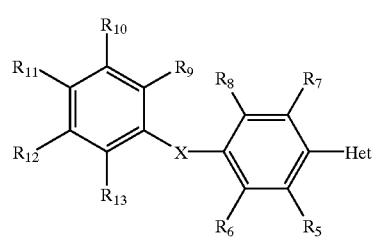

I or a pharmaceutically acceptable salt, prodrug or solvate thereof, wherein Het and $R_5$–$R_{13}$ are set in the specification. The invention also is directed to the use of compounds of Formula I for the treatment of neuronal damage following global and focal ischemia, for the treatment or prevention of neurodegenerative conditions such as amyotrophic lateral sclerosis (ALS), and for the treatment, prevention or amelioration of both acute or chronic pain, as antitinnitus agents, as anticonvulsants, and as antimanic depressants, as local anesthetics, as antiarrhythmics and for the treatment or prevention of diabetic neuropathy.

39 Claims, No Drawings

OTHER PUBLICATIONS

Catterall, W.A., "Common modes of drug action on Na+ channels: local anesthetics, antiarrhythmics and anticonvulsants," *Trends Pharmacol. Sci. 8:*57–65, Elsevier Science Publishers B.V. (1987).

Catterall, W.A., "Structure and Function of Voltage–Sensitive Ion Channels," *Science 242:*50–61, American Association for the Advancement of Science (1988).

Creveling, C.R. et al., "Batrachotoxin–Induced Depolarization and [$^3$H] Batrachotoxinin–A 20α–Benzoate Binding in a Vesicular Preparation from Guinea Pig Cerebral Cortex," *Mol. Pharmacol. 23:*350–358, The American Society for Pharmacology and Experimental Therapeutics (1983).

Dann, O. et al., "Synthesen antimikrobieller biskationischer 2–(Phenoxyphenyl)–indole und –1–benzofurane," *Liebigs Ann. Chem. 3:*409–425, Verlag Chemie (1984).

Dann, O. et al., Syntheses of antimicrobial biscationic 2–(phenoxyphenyl)indoles and –1–benzofurans, *Chem. Abstracts 100:*Abstract No. 209577w, Chemical Abstract Service (1984).

Denicoff, K.D. et al., "Efficacy of Carbamazepine Compared With Other Agents: A Clinical Practice Survey," *J. Clin. Psychiatry 55:*70–76, Physicians Postgraduate Press, Inc. (1994).

Dimmock, J.R. et al., "(Aryloxy)aryl Semicarbazones and Related Compounds: A Novel Class of Anticonvulsant Agents Possessing High Activity in the Maximal Electroshock Screen," *J. Med. Chem. 39:*3984–3997, American Chemical Society (1996).

Donaldson, I., "Tegretol: A double blind trial in tinnitus," *Laryngol. Otol. 95:* 947–951, Headley Brothers Ltd. (1981).

Ermikov, A.F. et al., "Photoelectron spectra of 2–arylpyrroles and their structural analogs," *Zh. Obshch. Khim. 58:*450–457, Izdatelstvo Nauka (1988).

Ermikov, A.F. et al., "Photoelectron spectra of 2–arylpyrroles and their structural analogs," *Chem. Abstracts 110:*Abstract No. 114125q, Chemical Abstract Service (1989).

Filer, C.N., "The Preparation and Characterization of Tritiated Neurochemicals," *Chapter 6 in Isotopes in the Physical and Biomedical Sciences, vol. 1, Labeled Compounds (Part A)*, pp. 156–192, Elsevier Science (1987).

Fournie–Zaluski, M–C. et al., "Design of Orally Active Dual Inhibitors of Neutral Endopeptidase and Angiotensin–Converting Enzyme with Long Duration of Action," *J. Med. Chem. 39:*2594–2605, American Chemical Society (1996).

Golovanova, N. I. et al., "Substituent Effects on the Frequency of NH Stretching Bands in Pyrroles," *Russian J. of Organic Chem. 29:*1092–1096 (1993). A translation of *Zhurnal Organicheskoi Khimii 29:*1319–1324, Izdatelstvo Nauka (1993).

Graham, S.H. et al., "Neuroprotective Effects of a Use–Dependent Blocker of Voltage–Dependent Sodium Channels, BW619C89, in Rat Middle Cerebral Artery Occlusion," *J. Pharmacol. Exp. Ther. 269:*854–859, The American Society for Pharmacology and Experimental Therapeutics (1994).

Graham, S.H. et al., "A Dose–Response Study of Neuroprotection using the AMPA Antagonist NBQX in Rat Focal Cerebral Ischemia," *J. Pharmacol. Exp. Ther. 276:*1–4, The American Society for Pharmacology and Experimental Therapeutics (1996).

Grandberg, I.I. et al., "Dehydrogenation of Phenylpyrazolines with Functional Groups on the Benzene Ring," *J. Gen. Chem. USSR 30:*1404–1408, Consultants Bureau (1960).

Hamill, O.P. et al., "Improved Patch–Clamp Techniques for High–Resolution Current Recording from Cells and Cell–Free Membrane Patches," *Pfluegers Arch. 391:*85–100, Springer–Verlag (1981).

Hunskaar, S. et al., "Formalin test in mice, a useful technique for evaluating mild analgesics," *J. Neurosci. Methods 14:*69–76, Elsevier Science Publishers B.V. (1985).

Iwasaki, Y. et al., "CNQX prevents spinal motor neuron death following sciatic nerve transectin in newborn rats," *J. Neurological Sci. 134:*21–25, Elsevier Science B.V. (1995).

Korostova, S.E. et al., "Pyrroles from Ketoximes and Acetylene, 42. Features of the Synthesis of New 2–Arylpyrroles," *Chemistry Of Herocyclic Compounds 28:*510–514, Consultants Bureau (1992). A translation of *Khimiya Geterotsiklicheskikh Soedinenii 5:*609–613 (1992).

Korshak, V.V. et al., "Synthesis of Polymers by Polycyclization. Polypyrazoles–V.," *Polym. Sci. USSR 6:*1186–1195, Pergamon Press (1964).

Korshak, V.V. et al., "Synthesis of Polyhydrazones and Polypyrazoles by a Polycyclization Reaction," *J. Polym. Sci. Part A3:* 2425–2439, Interscience Publishers (1965).

Kuo, C.–C. et al., "Slow Binding of Phenytoin to Inactivated Sodium Channels in Rat Hippocampal Neurons," *Mol. Pharma. 46:*716–725, The American Society for Pharmacology and Experimental Therapeutics (1994).

Kuwano, E. et al., "Synthesis and Insect Growth Regulatory Activity of 1,5–Disubstituted Imidazoles with Non–terpene Chains," *Agric. Biol. Chem.* 55:2999–3004, Agricultural Chemical Society of Japan (1991).

Majumdar, B. et al., "An electrocochleographic study of the effect of lignocaine on patients with tinnitus," *Clin. Otolaryngol. 8:* 175–180, Blackwell Scientific Publications (1983).

Møller, A.R., "Similarities Between Chronic Pain and Tinnitus," *Am. J. Otol. 18:*577–585, W.B. Suanders (1997).

Ohizumi, Y. et al., "Specific Inhibition of [$^3$H] Saxitoxin Binding to Skeletal Muscle Sodium Channels by Geographutoxin II, a Polypeptide Channel Blocker," *J. Biol. Chem. 261:*6149–6152, The American Society of Biological Chemists (1986).

Pevarello, P. et al., "Synthesis and Anticonvulsant Activity of a New Class of 2–[(Arylkyl)amino]alkanamide Derivatives," *J. Med. Chem. 41:*579–590, American Chemical Society (1998).

Pichon, M. et al., "C–Glycosylation of Cyclin N–Acyliminium Ions with Trimethylsilyloxyfuran," *Tetrahedron Lett. 37:* 7963–7966, Pergamon Press (1996).

Radwan, S.M., "Synthesis and Reactions of Some Diphenyl Sulfides," *Collect. Czech. Chem. Commun. 57:*1553–1558, Institute of Organic Chemistry and Biochemistry, Academy of Sciences of the Czechoslovak Republic (1992).

Ragsdale, D.S. et al., "Frequency and Voltage–Dependent Inhibition of Type IIA Na+ Channels, Expressed in a Mammalian Cell line, by Local Anesthetic, Antiarrhythmic, and Anticonvulsant Drugs," *Mol. Pharmacol. 40:*756–765, The American Society for Pharmacology and Experimental Therapeutics (1991).

Schubert, H. et al., "p–Aryl– und p–Alkoxyphenyl–imidazole," *J. Prakt. Chem. 18:*192–202, Lepzig (1962).

Schubert, H. et al., "p–Aryl– and p–alkoxyphenyl–imidazoles," *Chem. Abstracts 58:*Abstract No. 11344g, Chemical Abstract Service (1963).

List of abstracts concerning SCRIP 1870:8, PJD Publications Ltd. (1993) provided by client.

List concerning *SCRIP* 1773:14, PJD Publications, Ltd. (1992) provided by client.

Sheardown, M.J. et al., "AMPA, but not NMDA, receptor antagonism is neuroprotective in gerbil global ischaemia, even when delayed 24 h," *Eur. J. Pharmacol.* 236:347–353, Elsevier Science Publishers B.V. (1993).

Simpson, J.J. et al., "Recent advances in the pharmacological treatment of tinnitus," *Trends Pharmacol. Sci.* 20:12–18, Elsevier In Association with the International Union of Pharmacology (1999).

Stille, J.K. et al., "Polymers from 1,3–Dipole Addition Reactions: The Nitrilimine Dipole from Acid Hydrazide Chlorides," *J. Polym. Sci. Part A–1* 6:2317–2330, Interscience Publishers (1968).

Stys, P.K. et al., "Ionic Mechanism of Anoxic Injury in Mammalian CNS White Matter: Role of $Na^+$ Channels and $Na^+$–$Ca^{2+}$ Exchanger," *J. Neurosci.* 12:430–439, Society of Neuroscience (1992).

Szmant, H.H. et al., "p–Nitro p–Acylphenyl Sulfides and Related Compounds," *J. Am. Chem. Soc.* 78: 4386–4389, American Chemical Society (1956).

Taylor, C.P. et al., "Na+ channels as targets for neuroprotective drugs," *Trends Pharmacol. Sci.* 16:309–316, Elsevier In Association with the International Union of Pharmacology (1995).

Todorova, N. et al., "Synthesis if 2–substituted benzimidazoles," *Tr. Nauchnoizsled. Khim.–Farm. Inst.* 10:85–94, Chemical Pharmaceutical Resarch Institute (1978).

Todorova, N. et al., "Synthesis of 2–substituted benzimidazoles," *Chem. Abstracts* 94:Abstract No. 30644w, Chemical Abstract Service (1981).

Tonndorf, J., "The analogy between tinnitus and pain: A suggestion for a physiological basis of chronic tinnitus," *Hear. Res.* 28:271–275, Elsevier/North–Holland Biomedical Press (1987).

Trofimov, B.A. et al., "Pyrroles from Ketoximes and Acetylene. III.* Synthesis of 2–Aryl– and 1–Vinyl–2–arylpyrroles," *Chemistry of Heterocyclic Compounds* 14:399–401, Consultants Bureau (1978). A translation of *Khimiya Geterotsiklicheskikh Soedinenii* 4:489–491, (1978).

Vedoorn, T.A. et al., "Functional Properties of Recombinant Rat $GABA_A$ Receptors Depend upon Subunit Composition," *Neuron* 4:919–928, Cell Press (1990).

Vodenicharov, R.I. et al., "Spectral Behaviour of 2–Substituted Benzimidazole Derivatives of Biphenyl and Biphenylether," *Dokl. Bolg. Akad. Nauk.* 31: 441–444, Akedemiia, Sofia (1978).

Walker, J., "Experiments on the Synthesis of Potential Cortical Hormone Substitutes. Hydroxy–carbonyl Derivatives of Diphenyl Ether and Related Compounds," *J. Chem. Soc.* 347–353, The Chemical Society (1942).

Wrathall, J.R. et. al., "Amelioration of Functional Deficits from Spinal Cord Trauma with Systemically Administered NBQX, and Antagonist of Non–N–methyl–D–aspartate receptors," *Exp. Neurology* 137:119–127, Academic Press, Inc. (1996).

Yamada, N. et al., "Synthesis and Bleaching Activity of 1,5–Disubstituted Imidazoles," *Biosci. Biotech. Biochem.* 56:1943–1948, Japan Society for Bioscience, Biotechnology and Agrochemistry (1992).

Inai, M. et al., "Preparation of indole derivatives as antiestrogenic agents," *Chemical Abstracts* 121:Abstract No. 133962d, Chemical Abstract Service (1994).

Hirohara, Y. et al., "Pyrazoles, their preparation, and agrochemical microbicides containing them," *Chemical Abstracts* 129:Abstract No. 91737s, Chemical Abstract Service (1998).

Derwent WPI, English language abstract of JP5287563 (Document AM2).

Derwent WPI, English language abstract of JP7025849 (Document AN2).

Derwent WPI, English language abstract of JP59075257 (Document AO2).

Hilborn, J.G., et al., "Poly(aryl ether–benzoxazoles)," *Macromol.* 23:2854–2861, American Chemical Society (1990).

Hedrick, J.L., "Imide–aryl ether benzothiazoles," *Polymer* 33:1399–1405, Butterworth–Heinemann (1992).

English language abstract of Document AM3, JP 7–25849, Derwent World Patents Index Accession No. C95–109395.

English language abstract of HU P905605, Derwent World Patents Index Accession No. 8532617.

CAPLUS DN 130:223302 also cited as WO 9911634 showing the various structures.*

Farber et al, "Antiepileptic drug & Agents . . . ", PubMed Abstr. 12192617,also cited as Mol. Psychiatry,7/7, 726–33(2002).*

Caputi et al, "Neuroprotective actions in vivo and electrophysiological actions in vitro of 202W92",PubMed Abstr. 11701138,also cited asd Brain Res. 19/2,259–68(2001).*

Agrawal et al, "Persistent sodium channel activity mediates subthreshold membrane potential . . . ", PubMed Abstr. 11226669,also cited as Neuroscience, 102/1,53–64(2001).*

Rawan et al,Coll. Czech. Chem. Commun. 57:1553–58(1992).*

Hilborn J.G. et al Macromolecules, 23:2854–61 (1990).*

Hedrich J.L., Polymer 33:1399–1405 (1992).*

Kroshak, V.V. et al., "Synthesis of Polymers by Polycyclization. Polypyrazoles—VI," *Polym. Sci. USSR* 6:1196–1201, Pergamon Press (1964).

* cited by examiner

ARYL SUBSTITUTED PYRAZOLES, IMIDAZOLES, OXAZOLES, THIAZOLES AND PYRROLES, AND THE USE THEREOF

This application is a divisional of U.S. patent application Ser. No. 09/533,864, filed Mar. 24, 2000, now U.S. Pat. No. 6,414,011 now allowed, which claims the benefit, under 35 U.S.C. 119(e), of the earlier filing date of U.S. Provisional Application No. 60/126,553, filed Mar. 26, 1999. The contents of each of these applications are fully incorporated by reference.

BACKGROUND OF THE INVENTION

1. Field of the Invention

This invention is in the field of medicinal chemistry. In particular, the invention relates to aryl substituted pyrazoles, imidazoles, oxazoles thiazoles and pyrroles, and the discovery that these compounds are anticonvulsants and act as blockers of sodium ($Na^+$) channels.

2. Related Background Art

Several classes of therapeutically useful drugs, including local anesthetics such as lidocaine and bupivacaine, antiarrhythmics such as propafenone and amioclarone, and anticonvulsants such as lamotrigine, phenytoin and carbamazepine, have been shown to share a common mechanism of action by blocking or modulating $Na^+$ channel activity (Catterall, W. A., Trends Pharmacol. Sci. 8:57–65 (1987)). Each of these agents is believed to act by interfering with the rapid influx of $Na^-$ ions.

Recently, other $Na^+$ channel blockers such as BW619C89 and lifarizine have been shown to be neuroprotective in animal models of global and focal ischemia and are presently in clinical trials (Graham et al., J. Pharmacol. Exp. Ther. 269:854–859 (1994); Brown et al., British J. Pharmacol. 115:1425–1432 (1995)).

The neuroprotective activity of $Na^+$ channel blockers is due to their effectiveness in decreasing extracellular glutamate concentration during ischemia by inhibiting the release of this excitotoxic amino acid neurotransmitter. Studies have shown that unlike glutamate receptor antagonists, $Na^-$ channel blockers prevent hypoxic damage to mammalian white matter (Stys el al., J. Neurosci. 12:430–439 (1992)). Thus, they may offer advantages for treating certain types of strokes or neuronal trauma where damage to white matter tracts is prominent.

Another example of clinical use of a $Na^-$ channel blocker is riluzole. This drug has been shown to prolong survival in a subset of patients with ALS (Bensim et al., New Engl. J. Med. 330:585–591 (1994)) and has subsequently been approved by the FDA for the treatment of ALS. In addition to the above-mentioned clinical uses, carbamazepine, lidocaine and phenytoin are occasionally used to treat neuropathic pain, such as from trigeminal neurologia, diabetic neuropathy and other forms of nerve damage (Taylor and Meldrum, Trends Pharmacol. Sci. 16:309–316 (1995)), and carbamazepine and lamotrigine have been used for the treatment of manic depression (Denicott et al., J. Clin. Psychiatry 55: 70–76 (1994)). Furthermore, based on a number of similarities between chronic pain and tinnitus (Moller, A. R. Am. J. Otol. 18: 577–585 (1997); Tonndorf, J. Hear. Res. 28: 271–275 (1987)) it has been proposed that tinnitus should be viewed as a form of chronic pain sensation (Simpson, J. J. and Davies, E. W. Tip. 20: 12–18 (1999)). Indeed, lignocaine and carbamazepine have been shown to be efficacious in treating tinnitus (Majumdar, B. et al. Clin. Otolaryngol. 8: 175–180 (1983); Donaldson, I. Laryngol. Otol. 95: 947–951 (1981)).

It has been established that there are at least five to six sites on the voltage-sensitive $Na^+$ channels which bind neurotoxins specifically (Catterall, W. A., Science 242:50–61 (1988)). Studies have further revealed that therapeutic antiarrhythmics, anticonvulsants and local anesthetics whose actions are mediated by $Na^+$ channels, exert their action by interacting with the intracellular side of the $Na^+$ channel and allosterically inhibiting interaction with neurotoxin receptor site 2 (Catterall, W. A., Ann. Rev. Pharmacol. Toxicol. 10:15–43 (1980)).

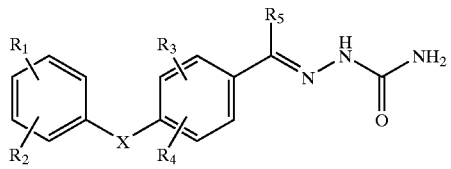

PCT International Published Application WO96/40628 discloses semicarbazones represented by the following Formula:

where $R_1$–$R_4$ are independently hydrogen, halogen, $C_{1-9}$ alkyl, $C_{3-9}$ cycloalkyl, cyano, $C_{1-9}$ alkoxy, or $C_{6-10}$ aryloxy; $R_5$ is hydrogen, $C_{1-9}$ alkyl, $C_{3-9}$ cycloalkyl, or $C_{6-10}$ aryl; and X is oxygen or sulfur. The compounds are disclosed to be useful as anticonvulsants.

Dimmock et al., (J. Med. Chem. 39:3984–3997 (1996)) discloses (aryloxy)aryl semicarbazones that displayed anticonvulsant activities when administered intraperitoneally to mice or orally to rats.

Pevarello et al., (J. Med. Chem. 41:579–590 (1998)) discloses 2-[(arylalkyl)amino]alkanamide derivatives represented by the following Formula:

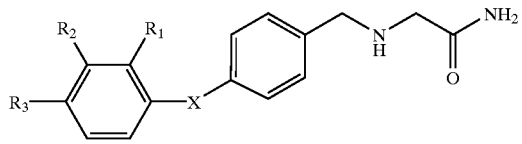

where $R_1$ is chloro, fluoro, trifluoromethyl, $R_2$ is chloro, cyano, fluoro, methyl, nitro, methoxy and trifluoromethyl, $R_3$ is chloro and fluoro and X is $CH_2O$, a bond, $CH_2$, $CH_2CH_2$, $CH_2S$, $CH_2NH$, $OCH_2$, $CH_2CH_2O$, $CH_2CH_2CH_2O$, $CH_2N(Me)$, $NHCH_2$, $CONH$ and $CH=CH$. The compounds are disclosed to be useful as anticonvulsants due to activity as sodium channel blockers.

PCT International Published Application WO 98/52940 discloses substituted pyrazoles of the following Formulae:

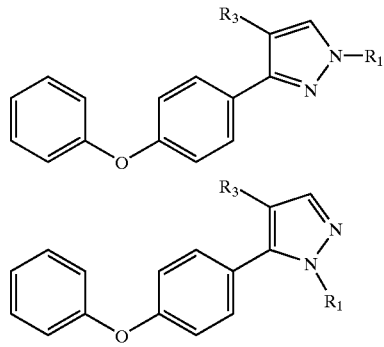

where $R_1$ is alkylsulfinyl, arylsulfinyl, alkylsulfonyl and acyl and $R_3$ is limited to pyridinyl, pyrimidinyl, quinolinyl, purinyl, C-attached malemides and pyridiones. The compounds are disclosed to be useful as p38 kinase inhibitors.

PCT International Published Application WO 98/50348 discloses substituted sulfonamides of the following Formula:

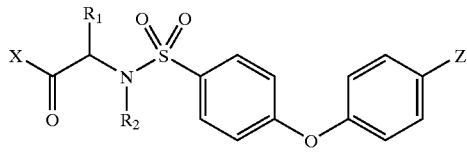

where Z is a heteroaryl group. The compounds are disclosed to be metalloproteinase inhibitors.

Japanese Patent Application JP 10168063 (CA 129:91737) discloses compounds of the following Formulae:

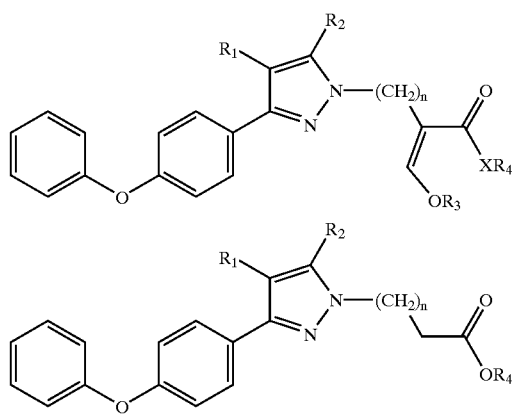

The compounds are described as microbiocides.

European Patent Application EP 446180 discloses substituted pyrazoles of the following Formula:

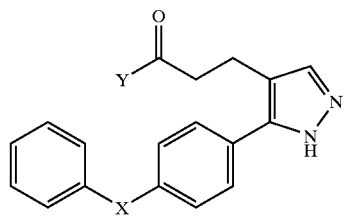

wherein X is oxygen and Y is $OC_2H_5$ or OH. The compounds are disclosed as starting materials.

Radwan, S. M. (*Collect. Czech. Chem. Commun.* 57(7). 1553–1558 (1992)) describes the synthesis of the compound of the following Formula:

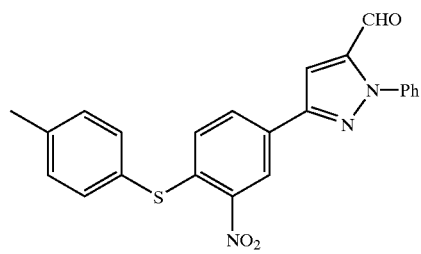

Korshak, K. K., et al., (*Polym. Sci. USSR (Engl. Transl.)* 6: 1087, 1196–1198 (1964) and *J. Polym. Sci. Part A* 3: 2425–2439 (1965)) describe the synthesis of the following compounds:

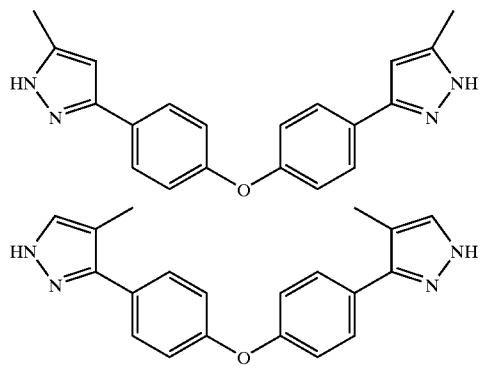

Stille et al. (*J. Polym. Sci. Part A-1* 6: 2317–2330 (1968)) describe the synthesis of the following compound:

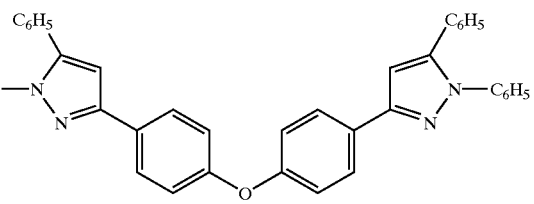

Szmant et al., (*J. Am. Chem. Soc.* 78: 4386–4389 (1956)) describes the following compound:

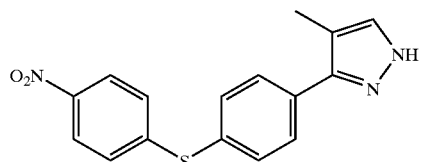

Grandberg et al. (*J. Gen. Chem. USSR (Engl. Transl)* 30: 1404–1408 (1960)) describe the synthesis of 3-(4-phenoxyphenyl)pyrazoles of the following Formula:

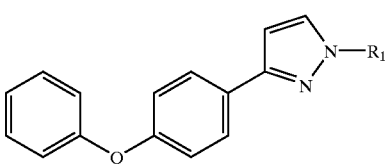

where $R_1$ is hydrogen or $C(O)NH_2$. With $R_1$ hydrogen, the picrate salt was also prepared.

The following pyrazoles are part of the available chemical directory (ACD):

2-chloro-6-[4-(1H-pyrazol-5-yl)phenoxy]benzonitrile; 2-chloro-6-[4-(1-methyl-1H-pyrazol-5-yl)phenoxy] benzonitrile; 2-chloro-6-[4-[1-(4-chlorobenzoyl)-1H-pyrazol-5-yl]phenoxy]benzonitrile; 2-[4-(1-acetyl-1H-pyrazol-5-yl)phenoxy]-6-chlorobenzonitrile; 2-chloro-6-(-4-[1-[(4-chlorophenyl)sulfonyl]-1H-pyrazol-5-yl] phenoxy)benzonitrile; 2-chloro-6-[4-[1-(methylsulfonyl)-1H-pyrazol-5-yl]phenoxy] benzonitrile; 2-chloro-6-[4-[1-(4-chlorophenyl)-1H-pyrazol-3-yl]phenoxy]benzonitrile; 3-(4-phenoxyphenyl)-1H-pyrazole; 3-[4-(4-nitrophenoxy)

phenyl]-1H-pyrazole; 3-[4-(4-methoxyphenoxy) phenyl]-1H-pyrazole; 3-[4-(phenylthio)phenyl]-1H-pyrazole; 3-[4-(phenylsulfonyl)phenyl]-1H-pyrazole; 5-(methylthio)-3-(4-phenoxyphenyl)-1H-pyrazole; N1-phenyl-5-(methylthio)-3-(-4-phenoxyphenyl)-1H-pyrazole-1-carboxamide; (4-chlorophenyl)[5-(methylthio)-3-(4-phenoxyphenyl)-1H-pyrazol-1-yl] methanone; N1-(4-chlorophenyl)-5-(methylthio)-3-(4-phenoxyphenyl)-1H-pyrazole-1-carboxamide; [5-(methylthio)-3-(-4-phenoxyphenyl)-1-pyrazol-1-yl] (phenyl)methanone; 3-(2-chloro-4[4-chlorophenoxy]) phenyl pyrazole; 1-phenylcarbamoyl-3-(2-chloro-4-[4-chlorophenoxy]phenyl pyrazole; 3-(2-chloro-4[4-chlorophenoxy])phenyl-1-(4-chlorophenylcarbamoyl) pyrazole; 3-(2-chloro-4[4-chlorophenoxyl]phenyl-1-(4-chlorobenzoyl)pyrazole; 1-(4-chlorobenzene-sulfonyl-3-(2-chloro-4-[4-chlorophenoxy] phenylpyrazole; 1-(2,4-dichlorophenylsulfonyl)-3-dimethylamino-4-(4-phenoxyphenyl)-pyrazole; N1-phenyl-5-morpholino-3-(4-phenoxypheny)-1H-pyrazole-1-carboxamide; 3-chloro-2-[5-[4-(phenylthio)phenyl]-1H-pyrazol-1-y]-5-(trifluoromethyl)-pyridine and 2-chloro-6-[4-(1-methyl-1H-pyrazol-3-yl)phenoxy]-benzonitrile.

Yamada et al. describe in *Biosci. Biotechnol. Biochem.* 56:1943–1948 (1992) the synthesis of the compounds of the following formula:

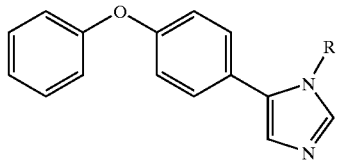

wherein R is H or Et. The compounds were inactive as bleaching agents in lettuce seedlings.

Kuwano et al. (*Agric. Biol. Chem.* 55:2999–3004 (1991)) describe the synthesis of the compound of the formula:

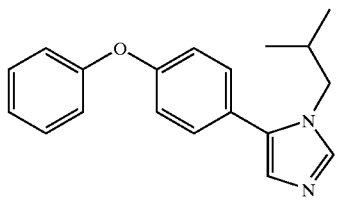

The compound is described as an insecticide.

Walker et al. (*J. Chem. Soc.* 347–350 (1942) describe the following compound as its picrate salt:

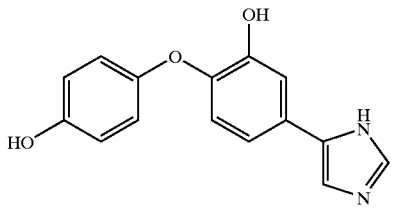

Schubert et al. (*J. Prakt. Chem.* 18 (No. 3–4): 192–202 (1962)) describes a compound of formula:

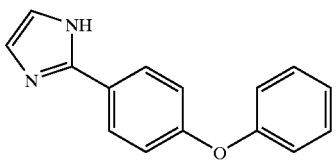

European Patent Application No. 269238 describes 2-(4-phenoxyphenyl)-14-imidazole-4,5-dicarbonitrile and 5-cyano-2-(4-phenoxyphenyl)-1H-imidazole-4-carboxamide as plant growth regulators.

WO 99/11627, JP 05287563, JP 59075257, Todorova et al. (*Tr. Nauchnoizsled. Khim.—Farm. Inst.* 10: 85–94 (1978)), and Vodenicharov et al. (*Dokl. Bolg. Akad. Nauk* 31(4): 441–444 (1978)) describe substituted benzimidazole derivatives.

Golanova et al. (*Zh. Org. Khim.* 29:1319–1324 (1993)), Ermikow et al. (*Z. Obshch. Khim.* 58: 450–457 (1988)), and Trofimov et al. (*Khim. Geterotsikl. Soedin.* 4: 489–491 (1978)) disclose 2-(4-phenoxyphenyl)-1H-pyrrole. No pharmaceutical use is described or suggested.

JP 07025849 describes a method for preparing 5-(4-phenoxyphenyl)-2-(trifluoromethyl)-1H-pyrrole-3-carbonitrile which is stated to be useful as intermediate for agrochemicals and pharmaceuticals.

Korostova et al. (*Khim. Geterotsikl. Soedin.* 5: 609–613 (1992)) disclose the synthesis of 2-[4-(phenylthio)phenyl]-1H-pyrrole.

Anderson et al. (*J. Med Chem.* 22: 977–980 (1979)) disclose substituted 1,2-dimethyl-5-[4-(phenylthio)]-1H-pyrroles and 1,2-dimethyl-5-[4-(phenylsulfonyl)]-1H-pyrroles that have antileukemic activity.

WO 93/23374 describes the preparation of several indole derivatives that are stated to have antiestrogenic properties.

Dann et al. (*Liebigs Ann. Chem.* 3: 409–425 (1984)) discloses several indole derivatives having antimicrobial activity.

2-[4-[3-(Aminoiminomethyl)phenoxy]phenyl]-1H-indole-6-carboximidamide has been reported to have antihyperpensive, antitumor, antifertility, antifungal and antibacterial properties.

Compounds of Formula I have not been used heretofor for treating a disorder responsive to the blockade of sodium channels in a mammal.

SUMMARY OF THE INVENTION

The present invention is related to the discovery that aryl substituted pyrazoles, imidazoles, oxazoles, thiazoles and pyrroles represented by Formula I are anticonvulsants and act as blockers of sodium ($Na^+$) channels.

The invention is also related with treating a disorder responsive to the blockade of sodium channels in a mammal suffering from excess activity of said channels by administering an effective amount of a compound of Formula I as described herein.

The present invention is also directed to the use of a compound of Formula I for the treatment of neuronal damage following global and focal ischemia, and for the treatment or prevention of neurodegenerative conditions, such as amyotrophic lateral sclerosis (ALS), for the treatment of tinnitus, as antimanic depressants, as local anesthetics, as antiarrhythmics, as anticonvulsants and for the treatment or prevention of diabetic neuropathy and for the treatment of pain including both acute and chronic pain and migraine headache.

Another aspect of the present invention is directed to the use of the compounds of Formula I as blockers of sodium channels.

A third aspect of the present invention is to provide a method for treating, preventing or ameliorating neuronal loss following global and focal ischemia; treating, preventing or ameliorating pain including acute and chronic pain, and neuropathic pain; treating, preventing or ameliorating convulsion and neurodegenerative conditions; treating, preventing or ameliorating manic depression; using as local anesthetics, antiarrhythmics, and treating tinnitus by administering a compound of Formula I to a mammal in need of such treatment.

A further aspect of the present invention is to provide a pharmaceutical composition useful for treating disorders responsive to the blockade of sodium ion channels, containing an effective amount of a compound of Formula I in a mixture with one or more pharmaceutically acceptable carriers or diluents.

A number of compounds useful in the present invention have not been heretofor reported. Thus, the present invention is also directed to novel aryl substituted pyrazoles, imidazoles, oxazoles, thiazoles and pyrroles of Formula I.

Further, the present invention is directed to $^3$H and $^{14}$C radiolabeled compounds of Formula I and their use as radioligands for their binding site on the sodium channel.

Additional embodiments and advantages of the invention will be set forth in part of the description which follows, and in part will be obvious from the description, or may be learned by practice of the invention. The embodiments and advantages of the invention will be realized and attained by means of the elements and combinations particularly pointed out in the appended claims.

It is to be understood that both the foregoing general description and the following detailed description are exemplary and explanatory only and are not restrictive of the invention, as claimed.

DETAILED DESCRIPTION OF THE INVENTION

The present invention arises out of the discovery that the aryl substituted pyrazoles, imidazoles, oxazoles, thiazoles and pyrroles of Formula I are anticonvulsants and act as blockers of Na$^+$ channels. In view of this discovery, compounds of Formula I are useful for treating disorders responsive to the blockade of sodium ion channels.

The compounds useful in this aspect of the present invention are the aryl substituted pyrazoles, imidazoles, oxazoles, thiazoles and pyrroles represented by Formula I:

I a pharmaceutically acceptable salt, prodrug or solvate thereof, wherein:

Het is a heteroaryl selected from the group consisting of

-continued

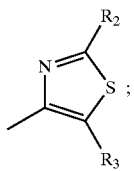

(x)

$R_1$ is selected from the group consisting of hydrogen, alkyl, cycloalkyl, aryl, aralkyl, heteroaryl, $C(O)R_{14}$, $CH_2C(O)R_{14}$, $S(O)R_{14}$, and $SO_2R_{14}$ all of which may be optionally substituted;

$R_2$, $R_3$, and $R_4$ are independently selected from the group consisting of hydrogen, alkyl, cycloalkyl, alkenyl, alkynyl, haloalkyl, aryl, aminoalkyl, hydroxyalkyl, alkoxyalkyl, alkylthio, alkylsulfinyl, alkylsulfonyl, carboxyalkyl, cyano, amino, alkylamino, aminocarbonyl, alkylaminocarbonyl, arylaminocarbonyl, aralkylaminocarbonyl, alkylcarbonylamino, arylcarbonylamino, aralkylcarbonylamino, alkylcarbonyl, heterocyclocarbonyl, aminosulfonyl, alkylaminosulfonyl, alkylsulfonyl, and heterocyclosulfonyl, or the R groups in adjacent carbon atoms can be taken together with the carbon atoms to which they are attached to form a carbocycle or a heterocycle. Examples of bridges formed by R groups taken together are —$OCH_2O$—, —$OCF_2O$—, —$(CH2)_3$—, —$(CH_2)_4$—, —$OCH_2H_2O$—, —$CH_2N(R_{15})CH_2$—, —$CH_2CH_2N(R_{15})CH_2$—, —$CH_2N(R_{15})CH_2CHl_2$—and —CH=CH—CH=CH—; where $R_{15}$ is hydrogen, alkyl, or cycloalkyl;

$R_5$, $R_6$, $R_7$, $R_8$, $R_9$, $R_{10}$, $R_{11}$, $R_{12}$, and $R_{13}$ are independently selected from the group consisting of hydrogen, halo, haloalkyl, aryl, cycloalkyl, saturated or partially unsaturated heterocycle, heteroaryl, alkyl, alkenyl, alkynyl, arylalkyl, arylalkenyl, arylalkynyl, heteroarylalkyl, heteroarylalkenyl, heteroarylalkynyl, cycloalkylalkyl, heterocycloalkyl, hydroxyalkyl, aminoalkyl, carboxyalkyl, alkoxyalkyl, nitro, amino, ureido, cyano, acylamino, amide, hydroxy, thiol, acyloxy, azido, alkoxy, carboxy, carbonylamido and alkylthiol; or $R_9$ and $R_{10}$ or $R_{10}$ and $R_{11}$ are taken together with the carbon atoms to which they are attached to form a carbocycle or a heterocycle. Examples of bridges formed by $R_9$ and $R_{10}$ or $R_{10}$ and $R_{11}$ taken together are —$OCH_2O$—, —$OCF_2O$—, —$(CH_2)_3$—, —$(CH_2)_4$—, —$OCH_2CH_2O$—, —$CH_2N(R_{15})CH_2$—, —$CH_2CH_2N(R_{15})CH_2$—, —$CH_2N(R_{15})CH_2CH_2$— and —CH=CH—CH=CH—; where $R_{15}$ is defined as above;

$R_{14}$ is selected from the group consisting of amino, alkyl, alkenyl, alkynyl, $OR_{16}$, alkylamino, dialkylamino, alkenylamino, cycloalkyl, aralkyl, aryl, heteroaryl, arylalkenyl, arylalkynyl, arylalkylamino, dialkylaminoalkenyl, heterocycle, heterocycloalkylamino, and cycloalkylalkylamino, all of which can be optionally substituted; wherein $R_{16}$ is selected from the group consisting of hydrogen, optionally substituted alkyl, and an alkalimetal; and X is one of O, S, $NR_{15}$, $CH_2$, $NR_{15}C(O)$, or $C(O)NR_{15}$, where $R_{15}$ is defined as above.

One group of useful compounds of the invention are compounds of the general Formula I, wherein Het is (i)–(vi), $R_1$–$R_{16}$ and X are as defined above with the following provisos that:
1) when Het is (i) or (ii),
   a) $R_1$ is H and X is O or S, at least one of $R_2$, $R_3$ and $R_2$–$R_{13}$ is other than H, except that $R_{11}$ is not $NO_2$ when $R_3$ is $C_3$, and $R_3$ is not —$CH_2CH_2COOH$ when the other substituents are each H;
   b) $R_1$ is H, X is O and one of $R_9$–$R_{13}$ is $NO_2$ or $OCH_3$, at least one the other substituents is other than H;
   c) X is O, $R_9$ or $R_{13}$ is CN and a Cl group is ortho to CN, at least one of $R_2$, $R_3$ and $R_5$–$R_8$ is other than H;
   d) X is O, $R_5$ and $R_{11}$ are Cl, at least one of $R_6$, $R_7$, $R_8$, $R_9$, $R_{10}$, $R_{12}$ and $R_{13}$ is other than H;
   e) X is O, $R_2$ is methylthio, $R_1$ is H or $C(O)R_{14}$ wherein $R_{14}$ is optionally substituted phenyl, at least one of $R_5$–$R_{13}$ is other than H; or
   f) $R_1$ is $C(O)NH_2$ and X is O, at least one of $R_2$, $R_3$ and $R_5$–$R_{13}$ is other than H;
2) when Het is (iii),
   a) $R_1$ is H, X is O or $CH_2$ and $R_2$ and $R_3$ together form —CH=CH—CH=CH—, $R_5$–$R_{13}$ are not all H;
   b) $R_1$ is Et and $R_2$ and $R_3$ together form —CH=CH—CH=CH—, X is not —NEt; or
   c) $R_1$ is H and X is O, $R_2$–$R_{13}$ are not all H;
3) when Het is (iv) and $R_1$ is H or alkyl, $R_2$–$R_{13}$ are not all H; or
4) when Het is (vi),
   a) X is O, S, or $CH_2$, $R_2$ and $R_4$ do not together form —CH=CH—CH=CH—;
   b) $R_1$ is H and X is O or S, $R_2$–$R_{13}$ are not all H; or
   c) X is S and $R_1$ and $R_2$ both are Me, at least one of $R_3$ and $R_4$ is other than—$CH_2OH$.

One group of preferred compounds falling within the scope of Formula I include compounds wherein $R_1$ is $C(O)R_{14}$ or $SO_2R_{14}$, where $R_{14}$ is amino or $C_{1-6}$ alkyl and X is O or S.

One group of preferred compounds falling within the scope of Formula I include compounds wherein $R_1$ is optionally substituted heteroaryl, optionally substituted $C_{1-6}$ alkyl, or $CH_2C(O)R_{14}$, wherein $R_{14}$ is an optionally substituted heterocycle, such as N-morpholinyl, N-pyrrolidinyl or N-piperazinyl, optionally substituted $C_{1-6}$ alkyl, $C_{1-6}$ alkylamino, $C_{1-6}$ dialkylamino, or $OR_{16}$, wherein $R_{16}$ is $C_{1-6}$ alkyl.

One group of preferred compounds falling within the scope of Formula I include compounds wherein Het is selected from the group consisting of (i), (ii), (iv) and (v).

When Het is (iii), (iv) or (v), $R_1$ is preferably H or alkyl and $R_2$ and $R_3$ are both hydrogen.

Preferably, when Het is (vi), $R_1$ is hydrogen, $R_2$ is selected from the group consisting of aminocarbonyl, alkylaminocarbonyl, alkylcarbonyl, heterocyclocarbonyl, aminosulfonyl, alkylaminosulfonyl, alkylsulfonyl, and heterocyclosulfonyl, preferably aminocarbonyl, and $R_3$ and $R_4$ are both hydrogen.

One group of preferred compounds falling within the scope of Formula I include compounds wherein Het is selected from the group consisting of (vii), (viii), (ix) and (x).

Preferably, $R_1$ is selected from the group consisting of an alkyl optionally substituted by halogen, hydroxy, carbamoyloxy, $C_{1-6}$ acyl, $C_{1-6}$ alkylsulfonylamino, aryl, preferably phenyl, or aminocarbonyl, heteroaryl, preferably pyrimidine, $C(O)R_{14}$, $CH_2C(O)R_{14}$, or $SO_2R_{14}$, wherein $R_{14}$ is selected from the group consisting of $C_{1-6}$ alkyl, $C_{2-6}$ alkenyl, $OR_{16}$, amino, $C_{1-6}$ alkylamino, di($C_{1-6}$)alkylamino, $C_{2-6}$ alkenylamino, di($C_{1-6}$)alkylaminoalkenyl, heterocycle, and heterocyclo($C_{1-6}$)alkyl-amino, all of which can be optionally substituted, and wherein $R_{16}$ is as defined above.

Preferably, $R_{14}$ is selected from the group consisting of $C_{1-6}$ alkyl, $C_{1-6}$ alkenyl, $OR_{16}$, amino, $C_{1-6}$ alkylamino, di($C_{1-6}$)alkylamino, $C_{2-6}$ alkenylamino, di($C_{1-6}$)alkylamino ($C_{2-6}$)alkenyl, heterocycle, and heterocyclo($C_{1-6}$) alkylamino, all of which can be optionally substituted, wherein $R_{16}$ is as defined above.

Preferably, $R_2$–$R_4$ are independently selected from the group consisting of hydrogen, $C_1$–$C_6$ alkyl, $C_2$–$C_6$ alkenyl, $C_2$–$C_6$ alkynyl, amino($C_1$–$C_6$)alkyl, amino, $C_1$–$C_6$ alkylthio, cyano, $C_1$–$C_6$ alkylsulfinyl, hydroxy($C_1$–$C_6$)alkyl, $C_1$–$C_6$ alkoxy, aminocarbonyl, $C_1$–$C_6$ alkylaminocarbonyl, $C_6$–$C_{10}$ arylaminocarbonyl, $C_6$–$C_{10}$ aryl($C_1$–$C_6$) alkylcarbonylamino, $C_1$–$C_6$ alkylcarbonylamino, $C_6$–$C_{10}$ arylcarbonylamino, $C_6$–$C_{10}$ aryl($C_1$–$C_6$) alkylcarbonylamino, $C_1$–$C_6$ alkylcarbonyl, heterocyclocarbonyl, aminosulfonyl, $C_1$–$C_6$ alkylaminosulfonyl, $C_1$–$C_6$ alkylsulfonyl, and heterocyclosulfonyl, more preferably hydrogen, $C_1$–$C_6$ alkyl, $C_1$–$C_6$ alkoxy, amino ($C_1$–$C_6$)alkyl, $C_1$–$C_6$ alkylthio and aminocarbonyl.

Preferred values of $R_5$–$R_{13}$ include hydrogen, halo, $C_1$–$C_6$ haloalkyl, $C_6$–$C_{10}$ aryl, $C_4$–$C_7$ cycloalkyl, $C_1$–$C_6$ alkyl, $C_2$–$C_6$ alkenyl, $C_2$–$C_6$ alkynyl, $C_6$–$C_{10}$ aryl($C_1$–$C_6$) alkyl, $C_6$–$C_{10}$ aryl($C_2$–$C_6$)alkenyl, $C_6$–$C_{10}$ aryl($C_2$–$C_6$) alkynyl, $C_1$–$C_6$ hydroxyalkyl, nitro, amino, ureido, cyano, $C_1$–$C_6$ acylamido, hydroxy, thiol, $C_1$–$C_6$ acyloxy, azido, $C_1$–$C_6$ alkoxy, or carboxy. The groups $R_5$–$R_{13}$ each take place of a hydrogen atom that would otherwise be present in any position on the aryl ring to which the R group is attached.

Especially preferred are compounds where $R_5$–$R_8$ are all hydrogen.

Preferably X is O or S, more preferably X is O.

Preferably, $R_3$ and $R_4$ are both H.

Another group of useful compounds of this invention are those having the Formula II:

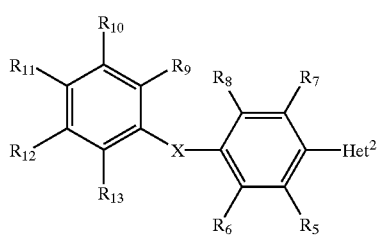

II or a pharmaceutically acceptable salt, prodrug or solvate thereof, wherein $Het^2$ is selected from the group consisting of

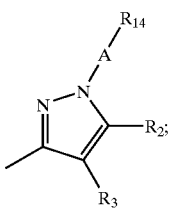

(i)²

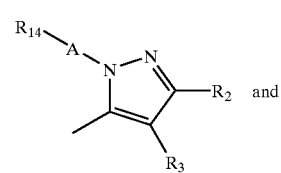

(ii)² and

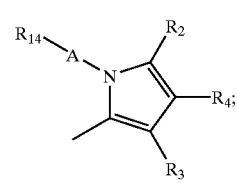

(vi)²

A is selected from the group consisting of C(O), $CH_2C(O)$, S(O) and $SO_2$;

$R_{2-15}$ are as defined previously with respect to Formula I; and

X is O or S, with the proviso that when $Het^2$ is (i)² or (ii)² a) X is O, $R_2$ is methylthio, $R_1$ is H or $C(O)R_{14}$ wherein $R_{14}$ is optionally substituted phenyl, at least one of $R_5$–$R_{13}$ is other than H; or b) $R_1$ is $C(O)NH_2$ and X is O, at least one of $R_2$, $R_3$ and $R_5$–$R_{13}$ is other than H.

Especially preferred compounds with respect to Formula II include those wherein:

$R_{14}$ is amino, optionally substituted $C_1$–$C_6$ alkyl, optionally substituted $C_1$–$C_6$ alkylamino or optionally substituted heterocycle, such as N-morpholinyl, N-pyrrolidinyl and N-piperazinyl;

$R_2$, $R_3$, and $R_4$ are independently hydrogen, $C_1$–$C_6$ alkyl, $C_1$–$C_6$ alkylthio or $C_1$–$C_6$ alkylsulfinyl; and X is O;

with the proviso that the compound is not 3-(4-phenoxyphenyl)-1H-pyrazole-1-carboxamide.

Also, preferred compounds of Formula II include those where A is C(O) or $CH_2C(O)$, X is O and $R_{14}$, $R_2$, $R_3$, and $R_4$ are as defined above.

Further, preferred compounds of Formula II include those where A is S(O) or $SO_2$, preferably $SO_2$, $R_2$–$R_4$ are independently H or $C_{1-6}$ alkyl and X is O. Also, preferred compounds of Formula II include those where A is S(O) or $SO_2$, preferably SO2, $R_2$–$R_4$ are H, $R_{14}$ is methyl and X is O.

Further another group of useful compounds of the invention are those having the Formula III:

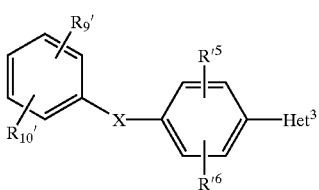

or a pharmaceutically acceptable salt, prodrug or solvate thereof, wherein

Het$^3$ is selected from the group consisting of

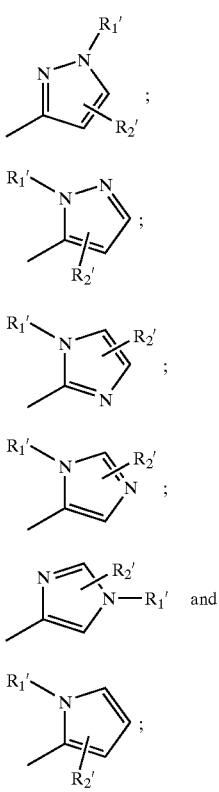

R'$_1$ is selected from the group consisting of hydrogen, optionally substituted alkyl, optionally substituted heteroaryl, C(O)R$_{14}$, CH$_2$C(O)R$_{14}$, S(O)R$_{14}$, and SO$_2$R$_{14}$;

R'$_2$ is attached to a carbon atom that is not the linking atom attached to the aryl group and is selected from the group consisting of hydrogen, alkyl, alkenyl, alkynyl, cyano, haloalkyl, aminoalkyl, hydroxyalkyl, alkoxyalkyl, alkylthio, alkylsulfinyl, alkylsulfonyl, carboxyalkyl, alkylamino, dialkylamino, aminocarbonyl, alkylaminocarbonyl, arylaminocarbonyl, aralkylaminocarbonyl, alkylcarbonylamino, arylcarbonylamino, aralkylcarbonylamino, alkylcarbonyl, heterocyclocarbonyl, aminosulfonyl, alkylaminosulfonyl, alkylsulfonyl, and heterocyclosulfonyl;

R'$_5$, R'$_6$, R'$_9$, and R'$_{10}$ are independently selected from the group consisting of hydrogen, halo, haloalkyl alkyl, alkenyl, alkynyl, hydroxyalkyl, aminoalkyl, carboxyalkyl, alkoxyalkyl, nitro, amino, ureido, cyano, acylamino, amide, hydroxy, thiol, acyloxy, azido, alkoxy, carboxy, carbonylamido and alkylthiol;

R$_{14}$ is selected from the group consisting of amino, alkyl, alkenyl, alkynyl, OR$_{16}$, alkylamino, dialkylamino, alkenylamino, dialkylaminoalkenyl, cycloalkyl, aralkyl, aryl, heteroaryl, arylalkenyl, arylalkenyl, heterocycle, heterocycloalkyl, and cycloalkylalkylamino, all of which can be optionally substituted; wherein R$_{16}$ is selected from the group consisting of hydrogen, optionally substituted alkyl, and an alkalimetal; and X is one of O, S, NR$_{15}$, CH$_2$, NR$_{15}$C(O), or C(O)NR$_{15}$ where R$_{15}$ is defined as above, with the following provisos that:

1) when Het is (i)$^3$ or (ii)$^3$,
  a) R'$_1$ is H and X is O or S, at least one of R'$_2$, R'$_5$, R'$_6$, R'$_9$ and R'$_{10}$ is other than H, except that R'$_9$ or R'$_{10}$ is not NO$_2$ when R'$_2$ is CH$_3$, and R'$_2$ is not —CH$_2$CH$_2$COOH when the other substituents are each H;
  b) R'$_1$ is H, X is O and R'$_9$ or R'$_{10}$ is NO$_2$ or OCH$_3$, at least one of the other substituents is other than H;
  c) X is O, R'$_9$ and R'$_{10}$ are CN and a Cl group ortho to CN, at least one of R'$_2$, R'$_5$ or R'$_6$ is other than H;
  d) X is O, R'$_5$ and R'$_9$ are Cl, at least one of R'$_6$ or R'$_{10}$ is other than H;
  e) X is O, R'$_2$ is methylthio, R'$_1$ is H or C(O)R$_{14}$ wherein R$_{14}$ is optionally substituted phenyl, at least one of R'$_5$, R'$_6$, R'$_9$ or R'$_{10}$ is other than H; or
  f) R'$_1$ is C(O)NH$_2$ and X is O, at least one of R'$_2$, R'$_5$, R'$_6$, R'$_9$ or R'$_{10}$ is other than H;
2) when Het is (iii)$^3$, R'$_1$ is H and X is O, R'$_5$, R'$_6$, R'$_9$ or R'$_{10}$ are not all H;
3) when Het is (iv)$^3$ and R'$_1$ is H or alkyl, R'$_5$, R'$_6$, R'$_9$ or R'$_{10}$ are not all H; or
4) when Het is (vi)$^3$, R'$_1$ is H and X is O or S, R'$_5$, R'$_6$, R'$_9$ or R'$_{10}$ are not all H.

Preferably X is O or S in compounds of Formula III.

Preferably, when Het$^3$ is (i)$^3$ or (ii)$^3$, R'$_1$ is heteroaryl, C(O)R$_{14}$, CH$_2$C(O)R$_{14}$, or SO$_2$R$_{14}$ wherein R$_{14}$ is amino, alkyl, alkylamino or heterocycle, more preferably amino, all of which can be optionally substituted. When R'$_2$ is aminocarbonyl, R'$_1$ is preferably hydrogen.

Preferably, when Het$^3$ is (vi)$^3$, R'$_1$ is hydrogen and R'$_2$ is selected from the group consisting of aminocarbonyl, alkylaminocarbonyl, alkylcarbonyl, heterocyclocarbonyl, aminosulfonyl, alkylaminosulfonyl, alkylsulfonyl, and heterocyclosulfonyl, preferably aminocarbonyl.

Preferably, when Het$^3$ is (iii)$^3$, (iv)$^3$ or (v)$^3$, R'$_1$ is hydrogen or alkyl, and R'$_2$ is hydrogen.

Preferably, R'$_2$ is selected from the group consisting of hydrogen, C$_1$–C$_6$ alkyl, halo(C$_1$–C$_6$)alkyl, amino(C$_1$–C$_6$) alkyl, hydroxy(C$_1$–C$_6$)alkyl, alkoxy(C$_1$–C$_6$)alkyl, C$_1$–C$_6$ alkylthio, C$_1$–C$_6$ alkylsulfinyl, carboxy(C$_1$–C$_6$)alkyl, C$_1$–C$_6$ alkylamino, aminocarbonyl, C$_1$–C$_6$ alkylaminocarbonyl, C$_1$–C$_6$ alkylcarbonyl, heterocyclocarbonyl, aminosulfonyl, C$_1$–C$_6$ alkylaminosulfonyl, C$_1$–C$_6$ alkylsulfonyl, and heterocyclosulfonyl; more preferably hydrogen, alkyl, halo (C$_1$–C$_6$)alkyl, amino(C$_1$–C$_6$)alkyl, alkoxy(C$_1$–C$_6$)alkyl, alkylthio, alkylamino, and aminocarbonyl. Most preferably R'$_2$ is hydrogen or aminocarbonyl.

Preferably, R'$_5$, R'$_6$, R'$_9$, and R'$_{10}$ are independently selected from the group consisting of hydrogen, halo, halo (C$_1$–C$_6$)alkyl, C$_1$–C$_6$ alkyl, hydroxy(C$_1$–C$_6$)alkyl, amino (C$_1$–C$_6$)alkyl, carboxy(C$_1$–C$_6$)alkyl, alkoxy(C$_1$–C$_6$)alkyl, nitro, amino, $C_1$–$C_6$ acylamino, amide, hydroxy, thiol, $C_1$–$C_6$ acyloxy, $C_1$–$C_6$ alkoxy, carboxy, carbonylamido and $C_1$–$C_6$ alkylthiol.

When $Het^3$ is $(i)^3$, $(ii)^3$ or $(vi)^3$, $R'_2$ is preferably attached to a carbon atom adjacent to a nitrogen atom.

Preferably, $Het^3$ is selected from the group consisting of $(i)^3$, $(ii)^3$, $(iii)^3$, $(iv)^3$ and $(v)^3$.

One group of preferable compounds of Formula III include compounds wherein $Het^3$ is $(i)^3$ or $(ii)^3$; $R'_1$ is $C(O)R_{14}$; $R'_2$ is as defined above; $R'_5$, $R'_6$, and $R'_{10}$ are independently selected from the group consisting of hydrogen, halo, haloalkyl, alkyl, alkenyl, alkynyl, hydroxyalkyl, aminoalkyl, carboxyalkyl, alkoxyalkyl, nitro, amino, ureido, cyano, acylamino, amide, hydroxy, thiol, acyloxy, azido, alkoxy, carboxy, carbonylamido and alkylthiol; $R'_9$ is selected from the group consisting of halo, haloalkyl, alkenyl, alkynyl, hydroxyalkyl, aminoalkyl, carboxyalkyl, alkoxyalkyl, nitro, amino, ureido, cyano, acylamino, amide, hydroxy, thiol, acyloxy, azido, alkoxy, carboxy, carbonylamido and alkylthiol; and $R_{14-16}$ and X are as defined above.

Another group of preferable compounds of Formula III include compounds wherein $Het^3$ is $(iii)^3$, $(iv)^3$, $(v)^3$ or $(vi)^3$; $R'_1$ is selected from the group consisting of hydrogen, optionally substituted alkyl, optionally substituted heteroaryl. $C(O)R_{14}$, $CH_2C(O)R_{14}$, $S(O)R_{14}$, and $SO_2R_{14}$; $R'_2$ is as defined above; $R'_5$, $R'_6$, and $R'_{10}$ are independently selected from the group consisting of hydrogen, halo, haloalkyl, alkyl, alkenyl, alkynyl, hydroxyalkyl, aminoalkyl, carboxyalkyl, alkoxyalkyl, nitro, amino, ureido, cyano, acylamino, amide, hydroxy, thiol, acyloxy, azido, alkoxy, carboxy, carbonylamido and alkylthiol; $R'_9$ is selected from the group consisting of halo, haloalkyl, alkenyl, alkynyl, hydroxyalkyl, aminoalkyl, carboxyalkyl, alkoxyalkyl, nitro, amino, ureido, cyano, acylamino, amide, hydroxy, thiol, acyloxy, azido, alkoxy, carboxy, carbonylamido and alkylthiol; and $R_{14-16}$ and X are as defined above.

Further another group of useful compounds of the invention are those having the Formula IV:

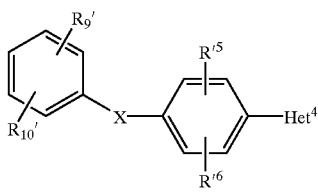

IV or a pharmaceutically acceptable salt, prodrug or solvate thereof, wherein $Het^4$ is selected from the group consisting of

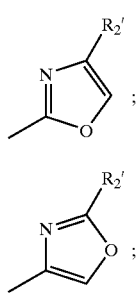

(vii)$^4$ (viii)$^4$

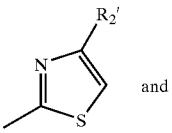

and (ix)$^4$

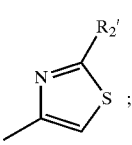

(x)$^4$ $R'_2$ is selected from the group consisting of hydrogen, alkyl, alkenyl, alkynyl, cyano, haloalkyl, aminoalkyl, hydroxyalkyl, alkoxyalkyl, alkylthio, alkylsulfinyl, alkylsulfonyl, carboxyalkyl, alkylamino, dialkylamino, aminocarbonyl, alkylaminocarbonyl, arylaminocarbonyl, aralkylaminocarbonyl, alkylcarbonylamino, arylcarbonylamino, aralkylcarbonylamino, alkylcarbonyl, heterocyclocarbonyl, aminosulfonyl, alkylaminosulfonyl, alkylsulfonyl, and heterocyclosulfonyl:

$R'_5$, $R'_6$, $R'_9$, and $R'_{10}$ are independently selected from the group consisting of hydrogen, halo, haloalkyl, alkyl, alkenyl, alkynyl, hydroxyalkyl, aminoalkyl, carboxyalkyl, alkoxyalkyl, nitro, amino, ureido, cyano, acylamino, amide, hydroxy, thiol, acyloxy, azido, alkoxy, carboxy, carbonylamido and alkylthiol; and X is one of O, S, $NR_{15}$, $CH_2$, $NR_{15}C(O)$, or $C(O)NR_{15}$ where $R_{15}$ is defined as above.

$Het^4$ is preferably selected from the group consisting of $(vii)^4$ and $(x)^4$. Preferably, $R'_2$, $R'_5$, $R'_6$, $R'_9$, and $R'_{10}$ are as described for Formula III.

Exemplary preferred compounds that may be employed in this method of invention include, without limitation:

3-[4-(4-fluorophenoxy)phenyl]-1H-pyrazole;

5-methylthio-3-(4-phenoxyphenyl)-1H-pyrazole-1-carboxamide;

5-methylsulfinyl-3-(4-phenoxyphenyl)-1H-pyrazole-1-carboxamide;

3-[4-(4-fluorophenoxy)phenyl]-1H-pyrazole-1-carboxamide;

3-[4-(4-nitrophenoxy)phenyl]-1H-pyrazole-1-carboxamide;

3-[4-(4-methoxyphenoxy)phenyl]-1H-pyrazole-1-carboxamide;

3-[4-(4-aminophenoxy)phenyl]-1H-pyrazole-1-carboxamide;

3-[4-(4-cyanophenoxy)phenyl]-1H-pyrazole-1-carboxamide;

3-[4-(3-chloro-2-cyanophenoxy)phenyl]-1H-pyrazole-1-carboxamide;

3-[4-(2,4-difluorophenoxy)phenyl]-1H-pyrazole-1-carboxamide;

3-[4-(4-chloro-2-fluorophenoxy)phenyl]-1H-pyrazole-1-carboxamide;

3-[4-(2-chloro-4-fluorophenoxy)phenyl]-1H-pyrazole-1-carboxamide;

1-[3-[4-(4-nitrophenoxy)phenyl]-1H-pyrazolyl]ethanone;

2-methyl-1-[3-(4-phenoxyphenyl)-1H-pyrazole] propanone;

1-methanesulfonyl-3-(4-phenoxy)phenyl-1H-pyrazole;

2-{5-[4-(4-fluorophenoxy)phenyl]-1H-pyrazol-1-yl}-1-(4-methyl)piperazin-1-yl-ethanone;

1-{5-[4-(4-fluorophenoxy)phenyl]-1H-pyrazol-1-yl}-2-methyl-propan-2-ol;

1-{5-[4-(4-fluorophenoxy)phenyl]-1H-pyrazol-1-yl}-propan-2-one;

1-morpholin-4-yl-2-{5-[4-(4-fluorophenoxy)phenyl]-1H-pyrazol-1-yl}-ethanone;

1-[2-(methanesulfonylamino)ethyl]-5-[4-(4-fluorophenoxy)phenyl]-1H-pyrazole;

1-(2-carbamoyloxyethyl)-5-[4-(4-fluorophenoxy)phenyl]-1H-pyrazole;

3-[4-(4-fluorophenylthio)phenyl]-1H-pyrazole-1-carboxamide;

3-[4-(4-fluorophenylthio)phenyl]-1H-pyrazole;

2-[5-[4-(4-fluorophenoxy)phenyl]-pyrazol-1-yl]ethanol;

3-[4-(4-fluorophenoxy)phenyl]-1H-pyrazole-1-carboxylic acid dimethylamide;

1-benzyl-5-[4-(4-fluorophenoxy)phenyl]-1H-pyrazole;

2-[3-[4-(4-fluorophenoxy)phenyl]-2H-pyrazol-2-yl]-1-pyrrolidin-1-yl ethanone;

2-(N-methylacetamido)-3-[4-(4-fluorophenoxy)phenyl]-2H-pyrazole;

2-{5-[4-(4-fluorophenoxy)phenyl]-pyrazol-1-yl}-acetamide;

2-{3-[4-(4-fluorophenoxy)phenyl]-pyrazol-1-yl}-acetamide;

3-{5-[4-(4-fluorophenoxy)phenyl]-pyrazol-1-yl}-propionamide;

3-[3-fluoro-4-(4-fluorophenoxy)phenyl]-1H-pyrazole-1-carboxamide;

2-{3-[4-(4-fluorophenoxy)phenyl]-pyrazol-1-yl}-pyrimidine; and

2-{3-[4-(4-trifluoromethylphenoxy)phenyl-1-pyrazol-1-yl}pyrimidine.

Additional useful compounds of the present invention include:

4-[4-(4-fluorophenoxy)phenyl]-1H-imidazole;

4-[4-(4-fluorophenoxy)-3-fluorophenyl]-1H-imidazole;

4-[4-(4-fluorophenoxy)-3-fluorophenyl]-1H-imidazole, hydrochloride salt;

4-[4-(2,4-difluorophenoxy)phenyl]-1H-imidazole;

4-[4-(2,4-difluorophenoxy)phenyl]-1H-imidazole, hydrochloride salt;

4-[4-(2-fluoro-4-chlorophenoxy)phenyl]-1-imidazole, hydrochloride salt;

4-(4-(4-trifluoromethylphenoxy)phenyl)-1H-imidazole, hydrochloride salt;

4-[4-(2,4-difluorophenoxy)phenyl]-2-methyl-1H-imidazole;

4-[4-(2,4-difluorophenoxy)phenyl]-1-methyl-1H-imidazole-2-carboxamide;

2-[4-(4-fluorophenoxy)phenyl]-1H-imidazole, hydrochloride salt;

2-[4-(4-fluorophenoxy)phenyl]-1H-benzimidazole;

2-[4-(4-fluorophenoxy)phenyl]-1H-imidazole-4-carboxamide;

2-[4-(4-fluorophenoxy)phenyl]-1H-imidazole-4-carbonitrile;

5-[4-(4-fluorophenoxy)phenyl]-pyrrole-2-carboxamide;

5-(4-phenoxyphenyl)pyrrole-2-carboxamide;

methyl 5-[4-(4-fluorophenoxy)phenyl]pyrrole-2-carboxylate;

2-[4-(4-fluorophenoxy)phenyl]oxazole-4-carboxamide; and

4-[4-(4-fluorophenoxy)-3-fluorophenyl]thiazole-2-carboxamide.

Useful aryl groups are $C_{6-14}$ aryl, especially $C_{6-10}$ aryl. Typical $C_{6-14}$ aryl groups include phenyl, naphthyl, phenanthryl, anthracyl, indenyl, azulenyl, biphenyl, biphenylenyl and fluorenyl groups.

Useful cycloalkyl groups are $C_{3-8}$ cycloalkyl. Typical cycloalkyl groups include cyclopropyl, cyclobutyl, cyclopentyl, cyclohexyl and cycloheptyl.

The term "heteroaryl" as employed herein refers to groups having 5 to 14 ring atoms; 6, 10 or 14 π electrons shared in a cyclic array; and containing carbon atoms and 1, 2 or 3 oxygen, nitrogen or sulfur heteroatoms (where examples of heteroaryl groups are: thienyl, benzo[b]thienyl, naphtho[2,3-b]thienyl, thianthrenyl, furyl, benzofuryl, pyranyl, isobenzofuranyl, benzoxazonyl, chromenyl, xanthenyl, phenoxathiinyl, 2H-pyrrolyl, pyrrolyl, imidazolyl, pyrazolyl, pyridyl, pyrazinyl, pyrimidinyl, pyridazinyl, indolizinyl, isoindolyl, 3H-indolyl, indolyl, indazolyl, purinyl, 4H-quinolizinyl, isoquinolyl, quinolyl, phthalazinyl, naphthyridinyl, quinazolinyl, cinnolinyl, pteridinyl, 4aH-carbazolyl, carbazolyl, β-carbolinyl, phenanthridinyl, acridinyl, perimidinyl, phenanthrolinyl, phenazinyl, thiazolyl, isothiazolyl, phenothiazinyl, isoxazolyl, furazanyl, and phenoxazinyl groups).

Useful halo or halogen groups include fluorine, chlorine, bromine and iodine.

Useful alkyl groups include straight-chained and branched $C_{1-10}$ alkyl groups, more preferably $C_{1-6}$ alkyl groups. Typical $C_{1-10}$ alkyl groups include methyl, ethyl, propyl, isopropyl, butyl, sec-butyl, tert-butyl, 3-pentyl, hexyl and octyl groups. Also contemplated is a trimethylene group substituted on two adjoining positions on the benzene ring of the compounds of the invention.

Useful alkenyl groups are $C_{2-6}$ alkenyl groups, preferably $C_{2-4}$ alkenyl. Typical $C_{2-4}$ alkenyl groups include ethenyl, propenyl, isopropenyl, butenyl, and sec-butenyl.

Useful alkynyl groups are $C_{2-6}$ alkynyl groups, preferably $C_{2-4}$ alkynyl. Typical $C_{2-4}$ alkynyl groups include ethenyl, propynyl, butynyl, and 2-butynyl groups.

Useful arylalkyl groups include any of the above-mentioned $C_{1-10}$ alkyl groups substituted by any of the above-mentioned $C_{6-14}$ aryl groups. Useful values include benzyl, phenethyl and naphthylmethyl.

Useful arylalkenyl groups include any of the above-mentioned $C_{2-4}$ alkenyl groups substituted by any of the above-mentioned $C_{6-14}$ aryl groups.

Useful arylalkynyl groups include any of the above-mentioned $C_{2-4}$ alkynyl groups substituted by any of the above-mentioned $C_{6-14}$ aryl groups. Useful values include phenylethynyl and phenylpropynyl.

Useful heteroarylalkyl groups include any of the above-mentioned $C_{1-10}$ alkyl groups substituted by any of the above-mentioned heteroaryl groups.

Useful heteroarylalkenyl groups include any of the above-mentioned $C_{2-4}$ alkenyl groups substituted by any of the above-mentioned heteroaryl groups.

Useful heteroarylalkynyl groups include any of the above-mentioned $C_{2-4}$ alkynyl groups substituted by any of the above-mentioned heteroaryl groups.

Useful cycloalkylalkyl groups include any of the above-mentioned $C_{1-10}$ alkyl groups substituted by any of the above-mentioned cycloalkyl groups.

Useful haloalkyl groups include $C_{1-10}$ alkyl groups substituted by one or more fluorine, chlorine, bromine or iodine atoms, e.g. fluoromethyl, difluoromethyl, trifluoromethyl, pentafluoroethyl, 1,1-difluoroethyl and trichloromethyl groups.

Useful hydroxyalkyl groups include $C_{1-10}$ alkyl groups substituted by hydroxy, e.g. hydroxymethyl, hydroxyethyl, hydroxypropyl and hydroxybutyl groups.

Useful alkoxy groups include oxygen substituted by one of the $C_{1-10}$ alkyl groups mentioned above.

Useful alkylthio groups include sulfur substituted by one of the $C_{1-10}$ alkyl groups mentioned above.

Useful acylamino groups are any $C_{1-6}$ acyl (alkanoyl) attached to an amino nitrogen, e.g. acetamido, propionamido, butanoylamido, pentanoylamido, hexanoylamido as well as aryl-substituted $C_{2-6}$ substituted acyl groups.

Useful acyloxy groups are any $C_{1-6}$ acyl (alkanoyl) attached to an oxy (—O—) group, e.g. acetoxy, propionoyloxy, butanoyloxy, pentanoyloxy, hexanoyloxy and the like.

The term heterocycle is used herein to mean saturated or partially unsaturated 3–7 membered monocyclic, or 7–10 membered bicyclic ring system, which consists of carbon atoms and from one to four heteroatoms independently selected from the group consisting of O, N, and S, wherein the nitrogen and sulfur heteroatoms can be optionally oxidized, the nitrogen can be optionally quaternized, and including any bicyclic group in which any of the above-defined heterocyclic rings is fused to a benzene ring, and wherein the heterocyclic ring can be substituted on carbon or on a nitrogen atom if the resulting compound is stable. Examples include, but are not limited to, pyrrolidine, piperazine, morpholine, imidazoline, pyrazolidine, benzodiazepines and the like.

Useful heterocycloalkyl groups include any of the above-mentioned $C_{1-10}$ alkyl groups substituted by any of the above-mentioned heterocyclic groups.

Useful alkylamino and dialkylainino groups are —$NHR_{17}$ and —$NR_{17}R_{18}$, wherein $R_{17}$ and $R_{18}$ are $C_{1-10}$ alkyl groups.

Aminocarbonyl group is —$C(O)NH_2$.

Useful alkylaminocarbonyl groups are carbonyl groups substituted by —$NHR_{17}$ and —$NR_{17}R_{18}$, wherein $R_{17}$ and $R_{18}$ are $C_{1-10}$ alkyl groups as defined above.

Useful alkylcarbonyl groups are carbonyl groups substituted by any of the above-mentioned $C_{1-10}$ alkyl groups.

Useful alkylthiol groups include any of the above-mentioned $C_{1-10}$ alkyl groups substituted by a —SH group.

Useful alkylsulfinyl groups include any of the above-mentioned $C_{1-10}$ alkyl groups attached to a sulfinyl (—SO—).

Useful alkylsulfonyl groups include any of the above-mentioned $C_{1-10}$ alkyl groups attached to a sulfonyl (—$SO_2$—).

Useful alkylaminosulfonyl groups include —$NHR_{17}$ and —$NR_{17}R_{18}$ groups attached to a sulfonyl, wherein $R_{17}$ and $R_{18}$ are $C_{1-10}$ alkyl groups as defined above.

Aminosulfonyl is —$SO_2NH_2$,

A carbamoyloxy group is —O—C(O)—$NH_2$.

A carboxy group is —COOH.

An azido group is —$N_3$.

An ureido group is —NH—C(O)—$NH_2$.

An amino group is —$NH_2$.

An amide group is an organic radical having —NHC(O)— as a functional group.

Optional substituents on $R_1$, $R'_1$ and $R_{14}$–$R_{16}$ include any one of halo, halo($C_{1-6}$)alkyl, aryl, heterocycle, cycloalkyl, $C_{1-6}$alkyl, $C_{2-6}$ alkenyl, $C_{2-6}$ alkynyl, aryl($C_{1-6}$)alkyl, aryl($C_{2-6}$)alkenyl, aryl($C_{2-6}$)alkynyl, cycloalkyl($C_{1-6}$)alkyl, heterocyclo($C_{1-6}$)alkyl, hydroxy($C_{1-6}$)alkyl, amino($C_{1-6}$)alkyl, carboxy($C_{1-6}$)alkyl, alkoxy($C_{1-6}$)alkyl, nitro, amino, ureido, cyano, $C_{1-6}$ acylamino, hydroxy, thiol, $C_{1-6}$ acyloxy, azido, $C_{1-6}$ alkoxy, carboxy, aminocarbonyl, carbamoyloxy, $C_{1-6}$ alkylsulfonylamino, $C_{1-6}$ acyl, and $C_{1-6}$ alkylthiol groups mentioned above. Preferred optional substituents include: halo, halo($C_{1-6}$)alkyl, hydroxy($C_{1-6}$)alkyl, amino ($C_{1-6}$)alkyl, hydroxy, nitro, $C_{1-6}$ alkyl, $C_{1-6}$ alkoxy, aminocarbonyl, carbamoyloxy, $C_{1-6}$ alkylsulfonylamino, $C_{1-6}$ acyl and amino.

Unlike the semicarbazones disclosed by Dimmock et al. in U.S. Pat. No. 5,741,818, which are somewhat flexible molecules, the pyrazoles, imidazoles, oxazoles, thiazoles and pyrroles are much more rigid. In addition, the electronics of the pyrazole, imidazole, oxazole, thiazole and pyrrole ring are very different from that of a semicarbazone. For example, the 2'-nitrogen present in the semicarbazone is now replaced with the nitrogen atom at the 2-position of the pyrazole and thus is part of the six electron aromatic ring. Unlike the aminoalkanamides described by Pevarello, which contain a basic amine (pKa>7), the heteroaryl compounds of the invention do not have to be basic. Pyrazole, for example, is half-protonated only at pH 2.5 and substitution with an electron withdrawing carbonyl is expected to reduce its basicity further. In addition, it was found that the primary amides present in the semicarbazones and the aminopropionamides are not necessary for activity as sodium channel blockers in the aryl-pyrazoles and -imidazoles claimed in the present application. Based on these considerations, it is an unexpected finding that the aryl substituted pyrazoles, imidazoles, oxazoles, thiazoles and pyrroles show good activity as sodium channel blockers.

Since the compounds of Formula I are blockers of sodium ($Na^+$) channels, a number of diseases and conditions mediated by sodium ion influx can be treated employing these compounds. Therefore, the invention is related to a method of treating, preventing or ameliorating neuronal loss associated with stroke, global and focal ischemia, CNS trauma, hypoglycemia and surgery, spinal cord trauma: as well as treating or ameliorating neurodegenerative diseases including Alzheimer's disease, amyotrophic lateral sclerosis, Parkinson's disease, treating or ameliorating anxiety, convulsions, glaucoma, migraine headache, and muscle spasm. The compounds of Formula I are also useful as antitinnitus agents, antimanic depressants, as local anesthetics, and as antiarrhythmics; as well as for treating, preventing or ameliorating pain including surgical, chronic and neuropathic pain. In each instance, the methods of the present invention require administering to an animal in need of such treatment an effective amount of a sodium channel blocker of the present invention, or a pharmaceutically acceptable salt or prodrug thereof.

The invention disclosed herein is meant to encompass all pharmaceutically acceptable salts thereof of the disclosed compounds. The pharmaceutically acceptable salts include, but are not limited to, metal salts such as sodium salt, potassium salt, secium salt and the like; alkaline earth metals such as calcium salt, magnesium salt and the like; organic amine salts such as triethylamine salt, pyridine salt, picoline salt, ethanolamine salt, triethanolamine salt, dicyclohexylamine salt, N,N'-dibenzylethylenediamine salt and the like; inorganic acid salts such as hydrochloride, hydrobromide, sulfate, phosphate and the like; organic acid salts such as formate, acetate, trifluoroacetate, maleate, tartrate and the like; sulfonates such as methanesulfonate, benzenesulfonate, p-toluenesulfonate, and the like; amino acid salts such as arginate, asparginate, glutamate and the like.

The invention disclosed herein is also meant to encompass prodrugs of the disclosed compounds. Prodrugs are considered to be any covalently bonded carriers which release the active parent drug in vivo.

The invention disclosed herein is also meant to encompass the in vivo metabolic products of the disclosed compounds. Such products may result for example from the oxidation, reduction, hydrolysis, amidation, esterification and the like of the administered compound, primarily due to enzymatic processes. Accordingly, the invention includes compounds produced by a process comprising contacting a compound of this invention with a mammal for a period of time sufficient to yield a metabolic product thereof. Such products typically are identified by preparing a radiolabelled compound of the invention, administering it parenterally in a detectable dose to an animal such as rat, mouse, guinea pig, monkey, or to man, allowing sufficient time for metabolism to occur and isolating its conversion products from the urine, blood or other biological samples.

The invention disclosed herein is also meant to encompass the disclosed compounds being isotopically-labelled by having one or more atoms replaced by an atom having a different atomic mass or mass number. Examples of isotopes that can be incorporated into the disclosed compounds include isotopes of hydrogen, carbon, nitrogen, oxygen, phosphorous, fluorine and chlorine, such as $^{2}H$, $^{3}H$, $^{13}C$, $^{14}C$, $^{15}N$, $^{18}O$, $^{17}O$, $^{31}P$, $^{32}P$, $^{35}S$, $^{18}F$, and $^{36}Cl$, respectively.

Some of the compounds disclosed herein may contain one or more asymmetric centers and my thus give rise to enantiomers, diastereomers, and other stereoisomeric forms. The present invention is also meant to encompass all such possible forms as well as their racemic and resolved forms and mixtures thereof. When the compounds described herein contain olefinic double bonds or other centers of geometric asymmetry, and unless specified otherwise, it is intended to include both E and Z geometric isomers. All tautomers are intended to be encompassed by the present invention as well.

As used herein, the term "stereoisomers" is a general term for all isomers of individual molecules that differ only in the orientation of their atoms in space. It includes enantiomers and isomers of compounds with more than one chiral center that are not mirror images of one another (diastereomers).

The term "chiral center" refers to a carbon atom to which four different groups are attached.

The term "enantiomer" or "enantiomeric" refers to a molecule that is nonsuperimposeable on its mirror image and hence optically active wherein the enantiomer rotates the plane of polarized light in one direction and its mirror image rotates the plane of polarized light in the opposite direction.

The term "racemic" refers to a mixture of equal parts of enantiomers and which is optically inactive.

The term "resolution" refers to the separation or concentration or depletion of one of the two enantiomeric forms of a molecule.

The invention is also directed to a method for treating disorders responsive to the blockade of sodium channels in animals suffering thereof. Particular preferred embodiments of the aryl substituted heteroaryl compounds for use in method of this invention are represented by previously defined Formulae I–IV.

The compounds of this invention may be prepared using methods known to those skilled in the art. The 1H-pyrazoles of the present invention can be prepared as illustrated by exemplary reactions in Scheme 1 and 2. Scheme 1 illustrates the formation of a pyrazole-1-carboxamide from the corresponding 3-substituted-1H-pyrazole using sodium cyanate:

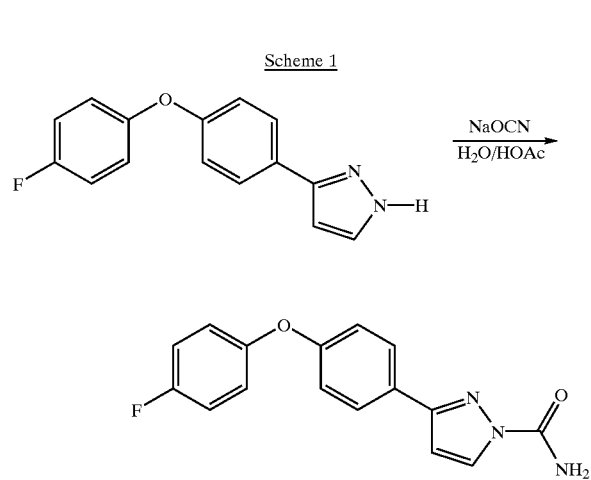

The 3-substituted-1H-pyrazoles were prepared as shown in Scheme 2 or were commerically available. 3-(4-Phenoxyphenyl)-1H-pyrazole, 3-[(4-nitrophenoxy)phenyl]-1H-pyrazole, 3-[(4-methoxyphenoxy)phenyl]-1H-1-pyrazole, 5-methylthio-3-(4-phenoxyphenyl)-1H-pyrazole and 3-[(3-chloro-2-cyanophenoxy)phenyl]-1H-pyrazole were obtained from Ryan Scientific (Isle of Palms, S.C.).

Scheme 2
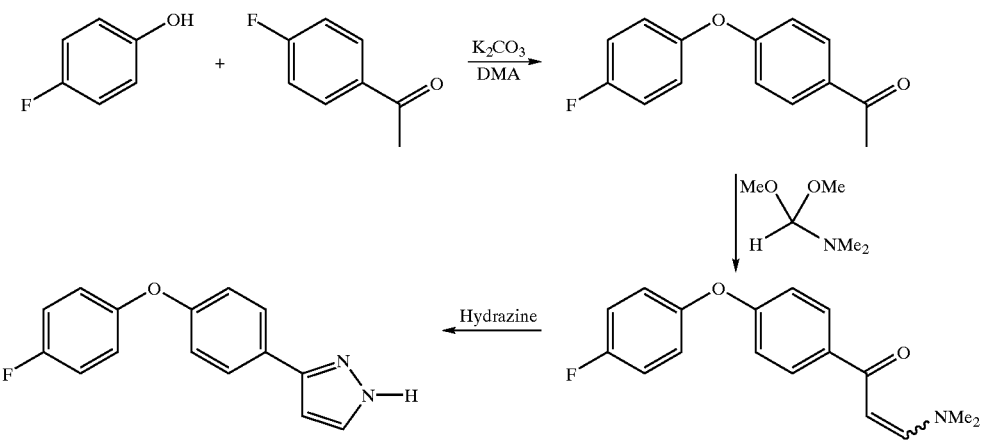
The 1,5-disubstituted pyrazoles can be prepared as shown in Scheme 3.
Scheme 3
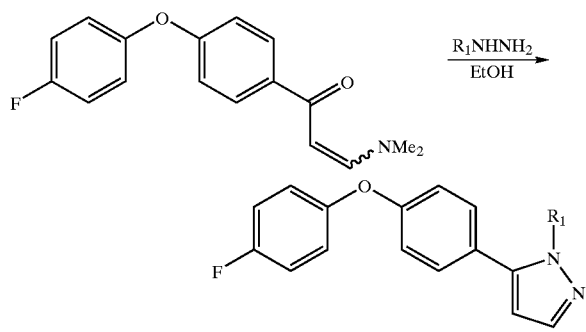
Major isomer formed
Compounds with Formula I wherein Het is (iii) can be prepared as illustrated by exemplary reactions in Scheme 4.
Scheme 4
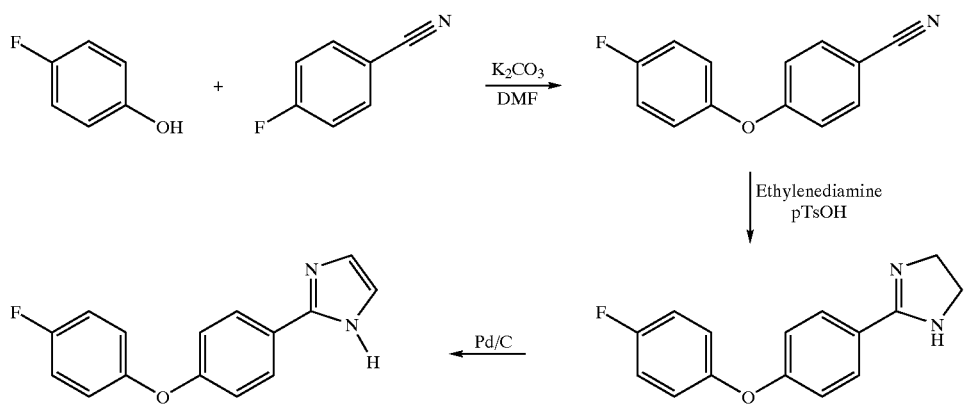
Compounds with Formula I where Het is (iv) and (v) can be prepared as illustrated by exemplary reactions in Scheme 5.

Scheme 5
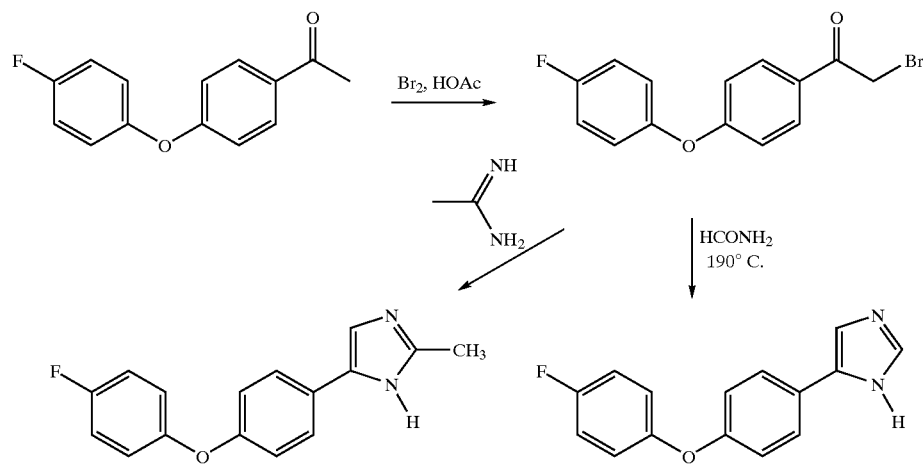
Compounds with Formula I where Het is (vi) can be prepared as illustrated by exemplary reactions in Scheme 6 using the method of Pichon, M. et al (*Tetrahedron Lett.* 37: 7963–7966 (1966)) and Fournie-Zaluski, M-C. et al. (*J. Med. Chem.* 39: 2594–2608 (1996)).
Scheme 6
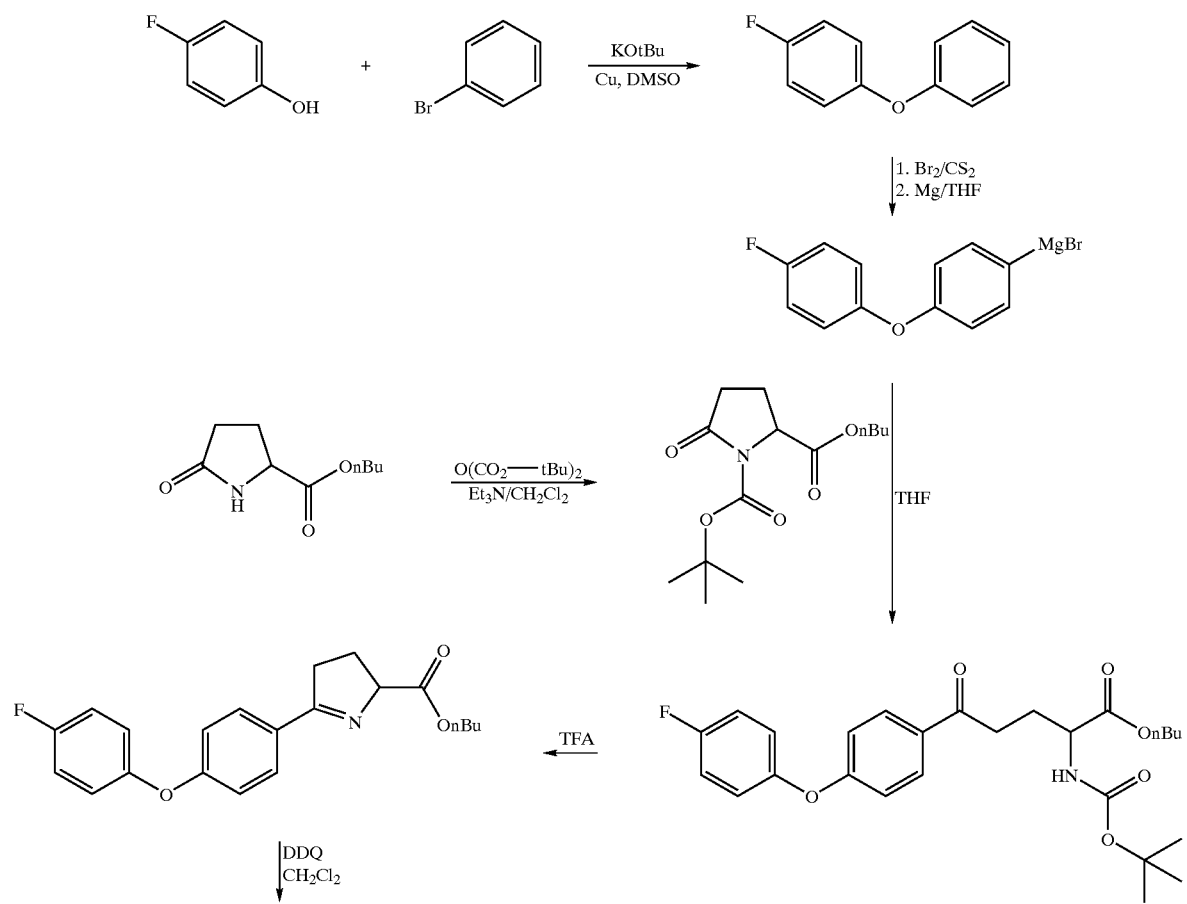

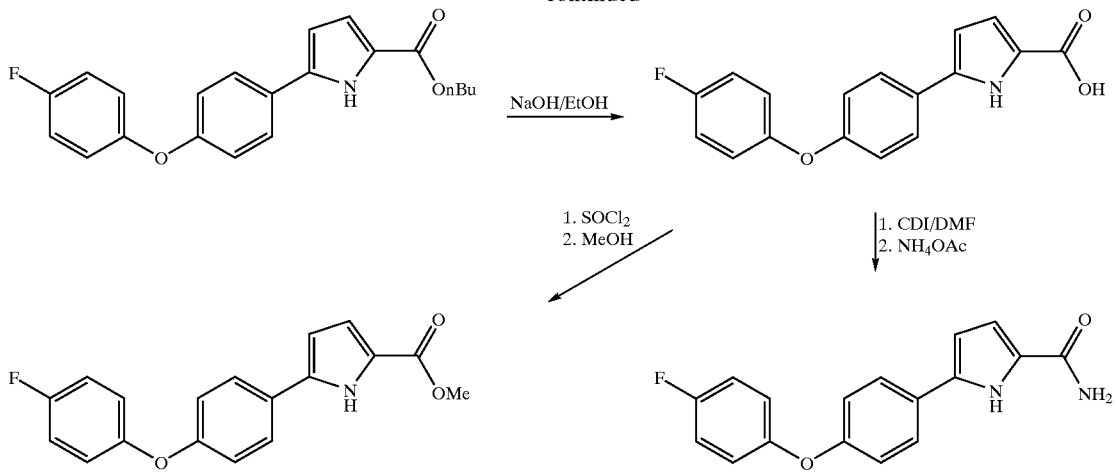

Compounds with Formula I wherein Het is (vii) can be prepared as illustrated in exemplary reactions in Sceme 7.

Scheme 7

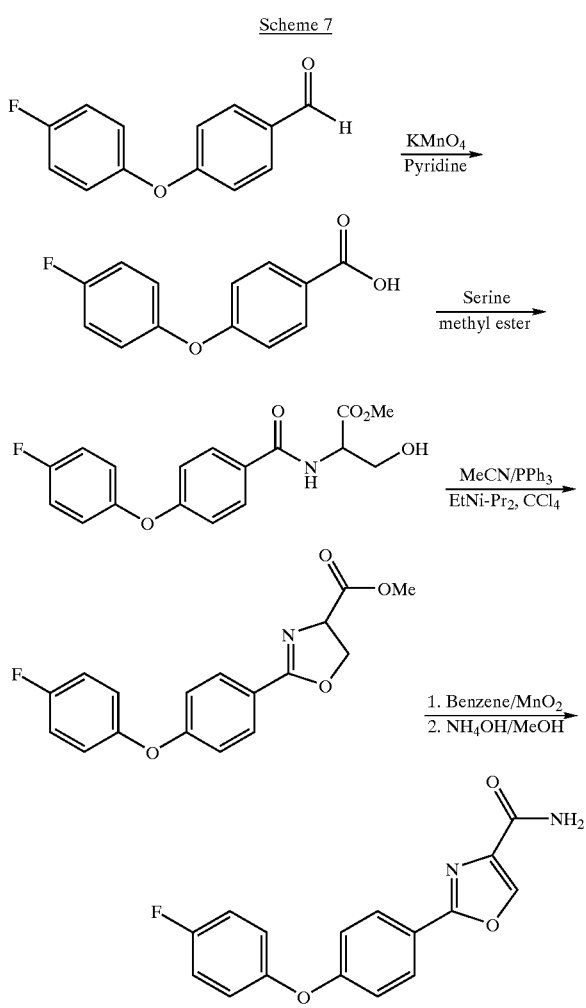

Compounds with Formula I where Het is (x) can be prepared as illustrated by examplary reactions in Scheme 8.

Scheme 8

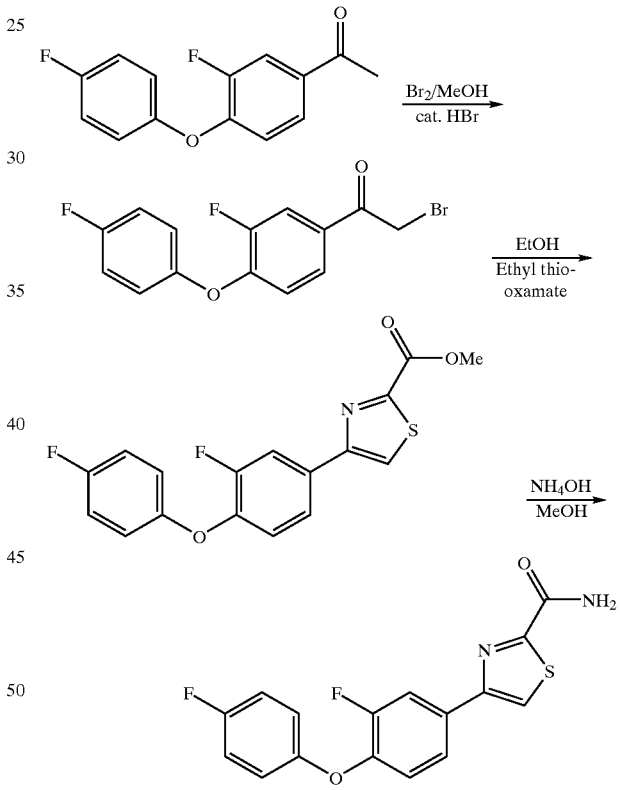

The invention is also directed to $^3$H and $^{14}$C radiolabeled compounds of Formula I and their use as radioligands for their binding site on the sodium channel. For example, one use of the labeled compounds of the invention is the characterization of specific receptor binding. Another use of the labeled compounds of the invention is an alternative to animal testing for the evaluation of structure-activity relationships. The receptor assay is performed at a fixed concentration of a labeled compound of Formula I and at increasing concentrations of a test compound in a competition assay.

Tritiated compounds of Formula I can be prepared by introducing tritium into the compound of Formula I by, for example, catalytic dehalogenation with tritium. This method includes reacting a suitably halogen-substituted precursor of a compound of Formula I with tritium gas in the presence of a suitable catalyst, for example Pd/C, in the presence or absence of a base. Other suitable methods for preparing tritiated compounds can be found in Filer, *Isotopes in the Physical and Biomedical Sciences, Vol. 1, Labeled Compounds* (Part A), Chapter 6. $^{14}$C-labeled compounds can be prepared by employing starting materials having a $^{14}$C carbon.

The compounds of the present invention were assessed by electrophysiological assays in dissociated hippocampal neurons for sodium channel blocker activity. These compounds also could be assayed for binding to the neuronal voltage-dependent sodium channel using rat forebrain membranes and [$^3$H]BTX-B.

Sodium channels are large transmembrane proteins that are expressed in various tissues. They are voltage sensitive channels and are responsible for the rapid increase of Na$^+$ permeability in response to depolarization associated with the action potential in many excitable cells including muscle, nerve and cardiac cells.

One aspect of the present invention is the discovery of the mechanism of action of the compounds herein described as specific Na$^+$ channel blockers. Based upon the discovery of this mechanism, these compounds are contemplated to be useful in treating or preventing neuronal loss due to focal or global ischemia, and in treating or preventing neurodegenerative disorders including ALS, anxiety, and epilepsy. They are also expected to be effective in treating, preventing or ameliorating neuropathic pain, surgical pain, chronic pain and tinnitus. The compounds are also expected to be useful as antiarrhythmics, anesthetics and antimanic depressants.

The present invention is directed to compounds of Formulae I–IV that are blockers of voltage-sensitive sodium channels. According to the present invention, those compounds having preferred sodium channel blocking properties exhibit an IC$_{50}$ of about 100 μM or less in the electrophysiological assay described herein. Preferably, the compounds of the present invention exhibit an IC$_{50}$ of 10 μM or less. Most preferably, the compounds of the present invention exhibit an IC$_{50}$ of about 1.0 μM or less. Substituted heteroaryl compounds of the present invention may be tested for their Na$^+$ channel blocking activity by the following electrophysiological and binding assays.

Electrophysiological Assay 1

Cell preparation: HEK-293 cells stably expressing the hSkM1 isoform of Na$^+$ channels (generous gift from Dr. A. L. George, Vanderbilt University Medical School) were cultured using standard techniques, as described previously (Verdoorn, T. A, et al., *Neuron* 4:919–928 (1990)). For electrophysiology, cells were plated onto 35 mm Petri dishes (pre-coated with poly-D-lysine) at a density of 1:40 on the day of re-seeding from confluent cultures. Our experience has been that cells are suitable for recordings for 2–3 days after plating.

Patch-clamp recordings of voltage-sensitive Na$^+$ currents: Whole-cell voltage-clamp recordings were made using conventional patch-clamp techniques (Hamill et al., *Pfluegers Arch.* 391:85–100 (1981)) with an Axopatch 200A amplifier (Axon Instruments, Foster City, Calif.). Recordings were made within 2–3 hours after neuron dissociation. The recording chamber was continuously superfused with the external solution (150 mM NaCl, 5.4 mM KCl, 1.8 mM CaCl$_2$, 1 mM MgCl$_2$, 10 mM HEPES, 10 mM glucose, pH 7.4 (NaOH)) at a speed of about 1 mL/min. Recording pipettes were pulled from thick-walled capillaries (WPI, Sarasota, Fla.) and fire-polished. The pipette resistances ranged from 1 to 3 MΩ when the pipettes were filled with internal solution containing (in mM): 110 CsF, 10 NaCl, 5 MgCl$_2$, 11 EGTA, 10 HEPES, pH adjusted to 7.4 with CsOH. Osmolality was set with a difference of 15–20 mmol/kg between external and internal solutions (lower inside the cell). Drugs and intervening wash-outs were applied through a linear array of flow pipes (Drummond Microcaps, 2 μL, 64-mm length). Compounds are dissolved in dimethylsulfoxide (DMSO) to make a 30 mM stock solution, which was subsequently diluted into the external solution to give final concentrations of 0.1–100 μM. At the highest (1%) concentration, DMSO inhibited the size of Na$^+$ current only slightly. Currents were recorded at room temperature (22–25° C.), filtered at 5 kHz with an active 8-pole Bessel filter (Frequency Devices, Haverhill, Mass.), digitized at 10–50 μs intervals, and stored using Digidata 1200 analog/digital interface with Pclamp6/Clampex software (Axon Instruments). Series resistance was cancelled typically by ~75% when necessary. The inhibitory potency of drugs was assessed by measuring reductions in the peak amplitude of Na$^+$ currents induced by increasing concentrations of compounds tested. Na$^+$ currents were elicited by stepping membrane voltage from holding potentials over the range −100 mV to −50 mV, to a pulse potential of −10 mV. The test pulse duration was 5–10 msec, repeated at a frequency ≦1 Hz. Concentration-inhibition curves were fitted with equation 1:

$$I/I_{control}=1/(1+([\text{compound}]/IC_{50})) \qquad \text{Eq. 1}$$

where I$_{control}$ is the maximal Na$^+$ current in the absence of antagonist, [compound] is the drug concentration, and IC$_{50}$ is the concentration of compound that produces half maximal inhibition.

Electrophysiological Assay 2

Cell preparation: HEK-293 (NaIIA-B2) cell line stably expressing the rBIIA isoform of Na$^+$ channels was established in-house. The cells were cultured using standard techniques, as described previously (Verdoorn, T. A, et al., *Neuron* 4:919–928 (1990)). For electrophysiology, cells were plated onto poly-D-lysine pre-coated Cellware 35 mm Petri dishes (BIOCOAT, Becton Dickinson) at a density of ~10$^4$ cells/dish on the day of re-seeding from confluent cultures. Our experience has been that cells are suitable for recordings for 2–3 days after plating.

Patch-clamp recordings of voltage-sensitive Na$^+$ currents. Whole-cell voltage-clamp recordings were made using conventional patch-clamp techniques (Hamill et al., *Pfluegers Arch.* 391:85–100 (1981)) with an Axopatch 200A amplifier (Axon Instruments, Foster City, Calif.). The recording chamber was continuously superfused with the external solution (150 mM NaCl, 5.4 mM KCl, 1.8 mM CaCl$_2$, 1 mM MgCl$_2$, 10 mM HEPES, 10 mM glucose, pH7.4 adjusted with NaOH, osmolality ~320 mmol/kg) at a speed of about 1 mL/min. Recording pipettes were pulled from the thick-walled capillaries (WPI, Sarasota, Fla.) and fire-polished. The pipette resistances ranged from 1 to 3 MΩ when the pipettes were filled with internal solution containing (in mM): 130 CsF, 20 NaCl, 2 MgCl$_2$, 10 EGTA, 10 HEPES, pH adjusted to 7.4 with CsOH, osmolality ~310 mmol/kg. Drugs and intervening wash-outs were applied through a linear array of flow pipes (Drummond Microcaps, 2 μL, 64-mm length). Compounds are dissolved in dimethylsulfoxide (DMSO) to make a 30 mM stock solution, which was subsequently diluted into the external solution to give final concentrations of 0.1–100 μM. At the highest (1%) concentration, DMSO inhibited the size of $Na^+$ current only slightly. Currents were recorded at room temperature (22–25° C.), filtered at 3 kHz with an active 8-pole Bessel filter (Frequency Devices, Haverhill, Mass.), digitized at 10–50 μs intervals, and stored using Digidata 1200 analog/digital interface with Pclamp6/Clampex software (Axon Instruments). Series resistance was cancelled typically by ~75% when necessary.

The following voltage pulse protocols were used to assess the potency and kinetics of inhibition of the $Na^+$ channels by the compounds (FIG. 1).

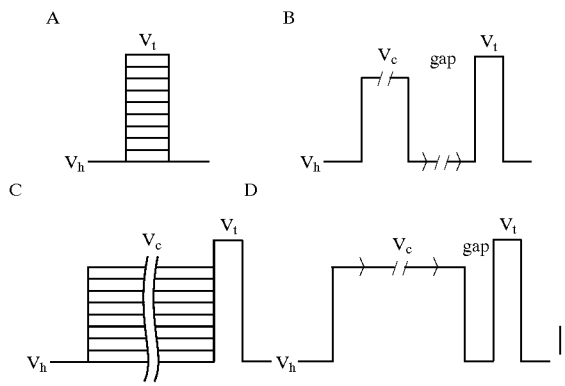

FIG. 1. Voltage pulse protocols. A. IV-curves. C. Steady-state inactivation. B. Repriming kinetics. D. Time course of binding.

Current-voltage relationship (IV-curve), protocol A, was used to report the voltage at which the maximal inward $Na^+$ current is achieved. This voltage was used throughout the experiment as testing voltage, $V_t$. The steady-state inactivation (or, availability) curve, protocol C, was used to get the voltage at which almost complete ($\geqq 95\%$) inactivation of $Na^+$ channels occurs; it served as voltage for conditioning prepulse, $V_c$, throughout the experiment. Protocol B reports how fast the channels recover from inactivation at hyperpolarized voltages. This permitted us to set up the duration of the hyperpolarization gap which is used in measurement of the kinetics of binding of compounds to inactivated $Na^+$ channels (protocol D). Channel repriming under control conditions was fast ($\geqq 90\%$ recovery during first 5–10 ms). If a drug substantially retards the repriming process then it becomes possible (protocol D) to accurately measure the kinetics of binding of the inhibitor to inactivated channels as well as the steady-state affinity ($k_+$ and $K_i$). To estimate $k_+$ values the reduction in peak currents in successive trials with varying pre-pulse duration was plotted as a function of pre-pulse duration and the time constant (τ) measured by mono-exponential fit. A plot of 1/τ as a function of antagonist concentration then allowed calculating of the macroscopic binding rates of the antagonists. To determine $K_i$ values the partial inhibition curves measured by fractional responses in steady-state were fitted with the logistic equation:

$$I/I_{control}=1/(1+([\text{antagonist}]/K_i)^p), \quad \text{Eq. 2}$$

where $I_{control}$ is the maximal $Na^+$ current in the absence of antagonist, [antagonist] is the drug concentration, $K_i$ is the concentration of antagonist that produces half maximal inhibition, and p is the slope factor.

In vitro Binding Assay

The ability of compounds of the present invention to modulate either site 1 or site 2 of the $Na^+$ channel was determined following the procedures fully described in Yasushi, *J. Biol. Chein.* 261:6149–6152 (1986) and Creveling, *Mol. Pharmacol.* 23:350–358 (1983), respectively. Rat forebrain membranes were used as sources of $Na^+$ channel proteins. The binding assays were conducted in 130 μM choline chloride at 37° C. for 60-minute incubation with [$^3$H] saxitoxin and [$^3$H] batrachotoxin as radioligands for site 1 and site 2, respectively.

In vivo Pharmacology

The compounds of the present invention may be tested for in vivo anticonvulsant activity after i.v., p.o. or i.p. injection using a number of anticonvulsant tests in mice, including the maximum electroshock seizure test (MES). Maximum electroshock seizures were induced in male NSA mice weighing between 15–20 g and male Sprague-Dawley rats weighing between 200–225 g by application of current (50 mA, 60 pulses/sec, 0.8 msec pulse width, 1 sec duration, D.C., mice; 99 mA, 125 pulses/sec, 0.8 msec pulse width, 2 sec duration, D.C., rats) using a Ugo Basile ECT device (Model 7801). Mice were restrained by gripping the loose skin on their dorsal surface and saline-coated corneal electrodes were held lightly against the two corneae. Rats were allowed free movement on the bench top and ear-clip electrodes were used. Current was applied and animals were observed for a period of up to 30 seconds for the occurrence of a tonic hindlimb extensor response. A tonic seizure was defined as a hindlimb extension in excess of 90 degrees from the plane of the body. Results were treated in a quantal manner.

The compounds may be tested for their antiociceptive activity in the formalin model as described in Hunskaar, S., O. B. Fasmer, and K. Hole, *J. Neurosci. Methods*14: 69–76 (1985). Male Swiss Webster NIH mice (20–30 g; Harlan, San Diego, Calif.) were used in all experiments. Food was withdrawn on the day of experiment. Mice were placed in Plexiglass jars for at least 1 hour to accommodate to the environment. Following the accommodation period mice were weighed and given either the compound of interest administered i.p. or p.o., or the appropriate volume of vehicle (10% Tween-80). Fifteen minutes after the i.p. dosing, and 30 minutes after the p.o. dosing mice were injected with formalin (20 μL of 5% formaldehyde solution in saline) into the dorsal surface of the right hind paw. Mice were transferred to the Plexiglass jars and monitored for the amount of time spent licking or biting the injected paw. Periods of licking and biting were recorded in 5 minute intervals for 1 hour after the formalin injection. All experiments were done in a blinded manner during the light cycle. The early phase of the formalin response was measured as licking/biting between 0–5 min, and the late phase was measured from 15–50 min. Differences between vehicle and drug treated groups were analyzed by one-way analysis of variance (ANOVA). A P value $\leqq 0.05$ was considered significant. Having activity in blocking the acute and second phase of formalin-induced paw-licking activity, the compounds are considered to be efficacious for acute and chronic pain. The compounds may be tested for their potential for the treatment of chronic pain (antiallodynic and antihyperalgesic activities) in the Chung model of peripheral neuropathy. Male Sprague-Dawley rats weighing between 200–225 g were anesthetized with halothane (1–3% in a mixture of 70% air and 30% oxygen) and their body temperature controlled during anesthesia through use of a homeothermic blanket. A 2-cm dorsal midline incision was then made at the L5 and L6 level and the para-vertibral muscle groups retracted bilaterally. L5 and L6 spinal nerves were then be exposed, isolated, and tightly ligated with 6–0 silk suture. A sham operation was performed exposing the contralateral L5 and L6 spinal nerves as a negative control.

Tactile Allodynia: Rats were transferred to an elevated testing cage with a wire mesh floor and allowed to acclimate for five to ten minutes. A series of Semmes-Weinstein monofilaments were applied to the plantar surface of the hindpaw to determine the animal's withdrawal threshold. The first filament used possessed a buckling weight of 9.1 gms (0.96 log value) and was applied up to five times to see if it elicited a withdrawal response. If the animal had a withdrawal response then the next lightest filament in the series would be applied up to five times to determine if it could elicit a response. This procedure was repeated with subsequent lesser filaments until there was no response and the lightest filament that elicited a response was recorded. If the animal did not have a withdrawal response from the initial 9.1 gms filament then subsequent filaments of increased weight were applied until a filament elicited a response and this filament was then recorded. For each animal, three measurements were made at every time point to produce an average withdrawal threshold determination. Tests were performed prior to and at 1, 2, 4 and 24 hours post drug administration. Tactile allodynia and mechanical hyperalgesia tests were conducted concurrently.

Mechanical Hyperalgesia: Rats were transferred to an elevated testing cage with a wire mesh floor and allowed to acclimate for five to ten minutes. A slightly blunted needle was touched to the plantar surface of the hindpaw causing a dimpling of the skin without penetrating the skin. Administration of the needle to control paws typically produced a quick flinching reaction, too short to be timed with a stopwatch and arbitrarily given a withdrawal time of 0.5 sec. The operated side paw of neuropathic animals exhibited an exaggerated withdrawal response to the blunted needle. A maximum withdrawal time of ten seconds was used as a cutoff time. Withdrawal times for both paws of the animals were measured three times at each time point with a five-minute recovery period between applications. The three measures were used to generate an average withdrawal time for each time point. Tactile allodynia and mechanical hyperalgesia tests were conducted concurrently.

The compounds may be tested for their neuroprotective activity after focal and global ischemia produced in rats or gerbils according to the procedures described in Buchan et al. (*Stroke*, Suppl. 148–152 (1993)) and Sheardown et al. (*Eur. J. Pharmacol.* 236:347–353 (1993)) and Graham et al. (*J. Pharmacol. Exp. Therap.* 276:1–4 (1996)).

The compounds may be tested for their neuroprotective activity after traumatic spinal cord injury according to the procedures described in Wrathall et. al. (*Exp. Neurology* 137:119–126 (1996)) and Iwasaki et. al. (*J. Neuro Sci.* 134:21–25 (1995)).

Compositions within the scope of this invention include all compositions wherein the compounds of the present invention are contained in an amount that is effective to achieve its intended purpose. While individual needs vary, determination of optimal ranges of effective amounts of each component is within the skill of the art. Typically, the compounds may be administered to mammals, e.g. humans, orally at a dose of 0.0025 to 50 mg/kg, or an equivalent amount of the pharmaceutically acceptable salt thereof, per day of the body weight of the mammal being treated for epilepsy, neurodegenerative diseases, anesthetic, arrhythmia, manic depression, and pain. For intramuscular injection, the dose is generally about one-half of the oral dose.

In the method of treatment or prevention of neuronal loss in global and focal ischemia, brain and spinal cord trauma, hypoxia, hypoglycemia, status epilepsy and surgery, the compound can be administrated by intravenous injection at a dose of about 0.025 to about 10 mg/kg.

The unit oral dose may comprise from about 0.01 to about 50 mg, preferably about 0.1 to about 10 mg of the compound. The unit dose may be administered one or more times daily as one or more tablets each containing from about 0.1 to about 10, conveniently about 0.25 to 50 mg of the compound or its solvates.

In addition to administering the compound as a raw chemical, the compounds of the invention may be administered as part of a pharmaceutical preparation containing suitable pharmaceutically acceptable carriers comprising excipients and auxiliaries which facilitate processing of the compounds into preparations which can be used pharmaceutically. Preferably, the preparations, particularly those preparations which can be administered orally and which can be used for the preferred type of administration, such as tablets, dragees, and capsules, and also preparations which can be administered rectally, such as suppositories, as well as suitable solutions for administration by injection or orally, contain from about 0.01 to 99 percent, preferably from about 0.25 to 75 percent of active compound(s), together with the excipient.

Also included within the scope of the present invention are the non-toxic pharmaceutically acceptable salts of the compounds of the present invention. Acid addition salts are formed by mixing a solution of the particular heteroaryl compound of the present invention with a solution of a pharmaceutically acceptable non-toxic acid such as hydrochloric acid, fumaric acid, maleic acid, succinic acid, acetic acid, citric acid, tartaric acid, carbonic acid, phosphoric acid, oxalic acid, dichloroacetic acid, and the like. Basic salts are formed by mixing a solution of the heteroaryl compound of the present invention with a solution of a pharmaceutically acceptable non-toxic base such as sodium hydroxide, potassium hydroxide, choline hydroxide, sodium carbonate and the like.

The pharmaceutical compositions of the invention may be administered to any animal that may experience the beneficial effects of the compounds of the invention. Foremost among such animals are mammals, e.g., humans, although the invention is not intended to be so limited.

The pharmaceutical compositions of the present invention may be administered by any means that achieve their intended purpose. For example, administration may be by parenteral, subcutaneous, intravenous, intramuscular, intraperitoneal, transdermal, or buccal routes. Alternatively, or concurrently, administration may be by the oral route. The dosage administered will be dependent upon the age, health, and weight of the recipient, kind of concurrent treatment, if any, frequency of treatment, and the nature of the effect desired.

The pharmaceutical preparations of the present invention are manufactured in a manner which is itself known, for example, by means of conventional mixing, granulating, dragee-making, dissolving, or lyophilizing processes. Thus, pharmaceutical preparations for oral use can be obtained by combining the active compounds with solid excipients, optionally grinding the resulting mixture and processing the mixture of granules, after adding suitable auxiliaries, if desired or necessary, to obtain tablets or dragee cores.

Suitable excipients are, in particular, fillers such as saccharides, for example lactose or sucrose, mannitol or sorbitol, cellulose preparations and/or calcium phosphates, for example tricalcium phosphate or calcium hydrogen phosphate, as well as binders such as starch paste, using, for example, maize starch, wheat starch, rice starch, potato starch, gelatin, tragacanth, methyl cellulose, hydroxypropylmethylcellulose, sodium carboxymethylcellulose, and/or polyvinyl pyrrolidone. If desired, disintegrating agents may be added such as the above-mentioned starches and also carboxymethyl-starch, cross-linked polyvinyl pyrrolidone, agar, or alginic acid or a salt thereof, such as sodium alginate. Auxiliaries are, above all, flow-regulating agents and lubricants, for example, silica, talc, stearic acid or salts thereof, such as magnesium stearate or calcium stearate, and/or polyethylene glycol. Dragee cores are provided with suitable coatings which, if desired, are resistant to gastric juices. For this purpose, concentrated saccharide solutions may be used, which may optionally contain gum arabic, talc, polyvinyl pyrrolidone, polyethylene glycol and/or titanium dioxide, lacquer solutions and suitable organic solvents or solvent mixtures. In order to produce coatings resistant to gastric juices, solutions of suitable cellulose preparations such as acetylcellulose phthalate or hydroxypropymethyl-cellulose phthalate, are used. Dye stuffs or pigments may be added to the tablets or dragee coatings, for example, for identification or in order to characterize combinations of active compound doses.

Other pharmaceutical preparations which can be used orally include push-fit capsules made of gelatin, as well as soft, sealed capsules made of gelatin and a plasticizer such as glycerol or sorbitol. The push-fit capsules can contain the active compounds in the form of granules which may be mixed with fillers such as lactose, binders such as starches, and/or lubricants such as talc or magnesium stearate and, optionally, stabilizers. In soft capsules, the active compounds are preferably dissolved or suspended in suitable liquids, such as fatty oils, or liquid paraffin. In addition, stabilizers may be added.

Possible pharmaceutical preparations, which can be used rectally, include, for example, suppositories, which consist of a combination of one or more of the active compounds with a suppository base. Suitable suppository bases are, for example, natural or synthetic triglycerides, or paraffin hydrocarbons. In addition, it is also possible to use gelatin rectal capsules which consist of a combination of the active compounds with a base. Possible base materials include, for example, liquid triglycerides, polyethylene glycols, or paraffin hydrocarbons.

Suitable formulations for parenteral administration include aqueous solutions of the active compounds in water-soluble form, for example, water-soluble salts and alkaline solutions. In addition, suspensions of the active compounds as appropriate oily injection suspensions may be administered. Suitable lipophilic solvents or vehicles include fatty oils, for example, sesame oil, or synthetic fatty acid esters, for example, ethyl oleate or triglycerides or polyethylene glycol-400 (the compounds are soluble in PEG-400). Aqueous injection suspensions may contain substances which increase the viscosity of the suspension, and include, for example, sodium carboxymethyl cellulose, sorbitol, and/or dextran. Optionally, the suspension may also contain stabilizers.

The following examples are illustrative, but not limiting, of the method and compositions of the present invention.

Other suitable modifications and adaptations of the variety of conditions and parameters normally encountered in clinical therapy and which are obvious to those skilled in the art are within the spirit and scope of the invention.

EXAMPLE 1

3-[4-(4-Fluorophenoxy)phenyl]-1H-pyrazole-1-carboxamide a) 1-[4-(4-Fluorophenoxy)phenyl]ethanone: A mixture of 4'-fluoroacetophenone (2.2 mL, 17.9 mmol), 4-fluorophenol (2.34 g, 20.6 mmol), and potassium carbonate (5.2 g, 38 mmol) in DMF (17 mL) was refluxed for 16 hours. The mixture was diluted with ethyl acetate and washed several times with an aqueous sodium hydroxide solution (2 N). The organic layer was separated, dried over sodium sulfate, filtered, and evaporated under reduced pressure to give 1-[4-(4-fluorophenoxy)phenyl]ethanone. $^1$H NMR (CDCl$_3$): δ 7.93 (d, J=8.7 Hz, 2H), 7.09–7.04 (m, 4H), 6.96 (d, J=8.4 Hz, 2H), 2.57 (s, 3H).

b) 3-[4-(4-Fluorophenoxy)phenyl]-1H-pyrazole. A mixture of crude 1-[4-(4-fluorophenoxy)phenyl]ethanone (17.9 mmol) and N,N-dimethylformamide dimethylacetal (2.6 mL, 18.4 mmol) in DMF (20 mL) was refluxed for 24 hours. The solution was then partitioned between ethyl acetate and water. The aqueous layer was extracted twice with ethyl acetate and the combined ethyl acetate layers were washed twice with water, dried over sodium sulfate, filtered, and evaporated under reduce pressure to give a yellow solid. The solid was dissolved in ethanol and neat hydrazine hydrate (2.2 mL, 70 mmol) was added. The solution was refluxed for 6 hours. After cooling to room temperature, the reaction was partitioned between ethyl acetate and water. The aqueous layer was extracted twice with ethyl acetate. The combined ethyl acetate layers were washed several times with water, dried over sodium sulfate, and evaporated under reduced pressure to give 4.4 g (97% crude yield) of 3-[4-(4-fluorophenoxy)phenyl]-1H-pyrazole. $^1$H NMR (CDCl$_3$): δ 10.6 (bs, 1H), 7.71 (d, J=8.4 Hz, 2H), 7.60 (d, J=2.1 Hz, 1H), 7.04–6.99 (m, 6H), 6.57 (d, J=2.4 Hz, 1H).

c) 3-[4-(4-Fluorophenoxy)phenyl]-1H-pyrazole-1-carboxamide. A solution of crude 3-[4-(4-fluorophenoxy)phenyl]-1H-pyrazole (4.4 g, 17.3 mmol) in glacial acetic acid (60 mL) and water (5 mL) was treated with a solution of sodium cyanate (1.4 g, 21 mmol) in 5 mL of water. After stirring at room temperature for 16 hours, the reaction was diluted with water, giving a solid precipitate. The crude product was filtered, dried and purified by column chromatography to give 2.79 g (52%) of the title compound as solid, mp 141–143° C. $^1$H NMR (DMSO-d$_6$): δ 8.28 (d, J=3.0 Hz, 1H), 7.94 (d, J=8.7 Hz, 2H), 7.84 (bs, 2H), 7.24 (t, J=8.4 Hz, 2H, 7.13–7.08 (m, 2H), 7.04 (d, J=8.4 Hz, 2H), 6.94 (d, J=2.7 Hz, 1H).

The following pyrazole-1-carboxamides were prepared by using a similar procedure:

3-[4-(2,4-Difluorophenoxy)phenyl]-1H-pyrazole-1-carboxamide; mp 132–134° C. $^1$H NMR (CDCl$_3$): δ 8.24 (d, J=2.7 Hz, 1H), 7.79 (d, J=8.7 Hz, 2H), 7.15–7.08 (m, 2H), 6.99 (d, J=8.4 Hz, 2H), 6.94–6.85 (m, 1H), 6.67 (d, J=3.0 Hz, 1H), 530 (bs, 2H).

3-[4-(4-Chloro-2-fluorophenoxy)phenyl]-1H-pyrazole-1-carhoxamide; mp 150–151° C. $^1$H NMR (CDCl$_3$): δ 8.24 (d, J=2.4 Hz, 1H), 7.80 (d, J=8.7 Hz, 2H), 7.23 (d, J=10.0 Hz, 1H), 7.13 (d, J=9.6 Hz, 1H), 7.06 (d, J=8.4 Hz, 1H), 7.02 (d, J=8.7 Hz, 2H), 6.68 (d, J=3.0 Hz, 1H), 5.25 (bs, 2H).

3-[4-(4-Trifluoromethylphenoxy)phenyl]-1H-pyrazole-1-carboxamide; mp 131–132° C. $^1$H NMR (CDCl$_3$): δ 8.27 (d, 1H, J=2.7 Hz), 7.86 (d, 2H, J=8.4 Hz), 7.59 (d, 2H, J=8.4 Hz), 7.16 (br s, 1H), 7.11 (d, 2H, J=8.4 Hz), 7.09 (d, 2H, J=8.4 Hz), 6.71 (d, 1H, J=2.7 Hz), 5.81 (br s, 1H). The compound was prepared from 3-[4-(4-trifluoromethylphenoxy)phenyl]-1H-pyrazole, mp 102–104° C., $R_f$ 0.33 (7/3 hexane/EtOAc), which in turn was prepared from 1-[4-(4-trifluoromethylphenoxy)phenyl] ethanone using the procedure described for the synthesis of 3-[4-(4-fluoromethylphenoxy)phenyl]-1H-pyrazole.

3-[4-(2-chloro-4-fluorophenoxy)phenyl]-1H-pyrazole-1-carboxamide can also be prepared by a similar method.

The following 3-substituted-pyrazole-1-carboxamides were prepared from the commercially available 3-substituted-1H-pyrazoles (Ryan Scientific, Isle of Palms, S.C.) as described for the conversion of 3-[4-(4-fluorophenoxy)phenyl]-1H-pyrazole to 3-[4-(4-fluorophenoxy)phenyl]-1H-pyrazole-1-carboxamide:

3-[4-(4-Methoxyphenoxy)phenyl]-1H-pyrazole-1-carboxamide; mp 156–159° C.; $^1$H NMR (CDCl$_3$): δ 8.23 (d, J=2.4 Hz, 1H), 7.77 (d, J=8.7 Hz, 2H), 7.14 (bs, 1H), 7.00 (dd, J=9.0, 7.8 Hz, 4H), 6.90 (d, J=9.3 Hz, 2H), 6.67 (d, J=2.4 Hz, 1H), 5.25 (bs, 1H), 8.32 (s, 3H).

5-Methylthio-3-(4-phenoxyphenyl)-1H-pyrazole-1-carboxamide; mp 142–144° C.; $^1$H NMR (CDCl$_3$): δ 7.77 (d, J=8.7 Hz, 2H), 7.37 (t, J=8.4 Hz, 2H), 7.14 (t, J=7.2 Hz, 1H), 7.07–7.04 (m, 4H), 6.34 (s, 1H), 5.20 (bs, 2H), 2.53 (s, 3H).

3-[4-(4-Nitrophenoxy)phenyl]-1H-pyrazole-1-carboxamide; mp 145–147° C.; $^1$H NMR (CDCl$_3$): δ 8.28 (d, J=2.4 Hz, 1H), 8.23 (d, J=9.0 Hz, 2H), 7.91 (d, J=8.4 Hz, 2H), 7.16 (d, J=8.7 Hz, 2H), 7.07 (d, J=9.3 Hz, 2H), 6.73 (d, J=3.0 Hz), 5.3 (bs, 2H).

3-[4-(3-Chloro-2-cyanophenoxy)phenyl]-1H-pyrazole-1-carboxamide; mp 180–181° C.; $^1$H NMR (CDCl$_3$): δ 8.27 (d, J=3.0 Hz, 1H), 7.90 (d, J=8.4 Hz, 2H), 7.40 (d, J=8.1 Hz, 1H), 7.21 (d, J=8.1 Hz, 1H), 7.16 (d, J=8.4 Hz, 1H), 6.80 (d, J=8.4 Hz, 1H), 6.72 (d, J=3.0 Hz, 1H), 5.27 (bs, 2H).

EXAMPLE 2

5-Methanesulfinyl-3-(4-phenoxyphenyl)-1H-pyrazole-1-carboxamide

To a solution of 5-thiomethyl-3-(4-phenoxyphenyl)-1H-pyrazole-1-carboxamide (122 mg, 0.375 mmol) in CHCl$_3$ at 0° C. was added solid m-chloroperoxybenzoic acid (57–86%; 129 mg). After several hours at 0° C., solid Na$_2$S$_2$O$_3$ was added and the mixture was stirred overnight. The reaction was added to a water/EtOAc mixture. The aqueous layer was washed with EtOAc and the pooled EtOAc layers were dried (Na$_2$SO$_4$), filtered, and concentrated to dryness. Column chromatography (1:1 hexane/EtOAc) gave 74 mg (58%) of the sulfoxide as a white solid, mp 92° C. $^1$H NMR (CDCl$_3$): δ7.79 (d, 2H–1, J=8.7 Hz), 7.38 (t, 2 H, J=8.0 Hz), 7.29 (s, 1H), 7.14 (t, 1H, J=7.2 Hz), 7.06 (d, 4H, J=8.4 Hz), 5.45 (br s, 2H), 3.05 (s, 3H).

EXAMPLE 3

3-[4-(4-Aminophenoxy)phenyl]-1H-pyrazole-1-carboxamide

A solution of 3-[4-(4-nitrophenoxy)phenyl]-1H-pyrazole-1-carboxamide (100 mg, 0.308 mmol) in ethanol was flushed with nitrogen for 5 min, then palladium (10% on carbon, 20 mg) was added. The mixture was shaken under 40 psi of hydrogen for 16 hours. The mixture was then filtered through a bed of Celite and the solvent was removed in vacuo. The crude product was purified by column chromatography to give 57 mg (60%) of the title compound as a solid, mp 158–160° C. $^1$H NMR (CDCl$_3$): δ 8.22 (d, J=3.0 Hz, 1H), 7.75 (d, J=8.7 Hz, 2H), 6.98 (d, J=8.7 Hz, 2H), 7.10 (bs, 1H), 6.90 (d, J=9.0 Hz, 2H), 6.70 (d, J=9.0 Hz, 2H), 6.66 (d, J=3.0 Hz, 1H), 5.25 (bs, 1H), 3.61 (bs, 2H).

EXAMPLE 4

3-[4-(2Cyanophenoxy)phenyl]-1H-pyrazole-1-carboxamide

A solution of 3-[4-(3-chloro-2-cyanophenoxy)phenyl]-1H-pyrazole-1-carboxamide (65 mg, 0.192 mmol) in ethanol formed upon heating. The solution was allowed to cool to room temperature, purged with nitrogen for 5 minutes, and 10% palladium on carbon (25 mg) was added. The mixture was stirred for 16 hours under a balloon filled with hydrogen. The mixture was then filtered through a bed of Celite and the filtrate was partitioned between water and ethyl acetate. The aqueous layer was extracted with ethyl acetate. The combined ethyl acetate layers were dried over sodium sulfate, filtered and evaporated under reduced pressure to give the crude product. Purification by column chromatography (60:40 hexane/ethyl acetate) afforded 15 mg (26%) of the title compound as a solid. TLC $R_f$=0.38 (60:40 hexane/ethyl acetate). $^1$H NMR (CDCl$_3$): δ 8.26 (d, J=2.4 Hz, 1H), 7.88 (d, J=9.0 Hz, 2H), 7.69 (dd, J=7.5, 1.5 Hz, 1H), 7.53–7.47 (m, 1H), 7.20–7.14 (m, 1H). 7.15 (d, J=9.0 Hz, 2H), 6.93 (d, J=8.7 Hz, 1H), 6.72 (d, J=2.7 Hz, 1H), 5.30 (bs, 2H).

EXAMPLE 5

1-[3-[4-(4-Nitrophenoxy)phenyl]-1H-pyrazolyl] ethanone

A solution of 3-[4-(-4-nitrophenoxy)phenyl]-1H-pyrazole (0.16 g, 0.57 mmol) in pyridine (12 mL) was treated with neat acetic anhydride (1.0 mL, 1.0 mmol) and allowed to stir at room temperature for 16 hours. The reaction was then diluted with ethyl acetate, washed several times with an aqueous 2N HCl solution, dried over sodium sulfate, and evaporated under reduced pressure. The crude product was purified by column chromatography, affording 116 mg (63%) of the title compound. TLC $R_f$ 0.78 (70:30 hexane/ethyl acetate). $^1$H NMR (CDCl$_3$): δ 8 8.31 (d, J=3.0 Hz, 1H), 8.22 (d, J=9.3 Hz, 2H), 7.94 (d, J=8.7 Hz, 2H), 7.17 (d, J=9.0 Hz, 2H), 7.07 (d, J=9.3 Hz, 2H), 6.77 (d, J=3.0 Hz, 1H), 2.78 (s, 3H).

EXAMPLE 6

2-Methyl-1-[3-(4-phenoxyphenyl)-1H-pyrazol-1-yl]-propan-1-one

A mixture of 3-(4-phenoxyphenyl)-1H-pyrazole (123 mg, 0.52 mmol) and NaH (28 mg, 0.70 mmol) in 5 mL of DMF was stirred at room temperature for 30 minutes. Neat isobutyryl chloride (80 μL, 0.75 mmol) was added and the reaction was stirred at room temperature. The reaction was then partitioned between water and EtOAc. The aqueous layer was extracted twice with EtOAc and the pooled organic layers were dried (Na$_2$SO$_4$), filtered and concentrated in vacuo. Column chromatography (5% EtOAc/hexane) gave 127 mg (80%) of the title compound as a white solid, mp 49–51° C. $^1$H NMR (CDCl$_3$): δ 8.30 (d, J=3.0 Hz, 1H), 7.88 (d, J=8.7 Hz, 2H), 7.39 (t, J=8.0 Hz, 2H), 7.17 (t, J=7.2 Hz, 2H), 7.12–7.08 (m, 4H), 6.75 (d, J=3.0 Hz, 1H), 4.03 (m, 1H), 1.78 (d, J=6.9 Hz, 6H).

EXAMPLE 7

1-Methanesulfonyl-3-(4-phenoxyphenyl)-1H-pyrazole

To a solution of 3-(4-phenoxyphenyl)-1H-pyrazole (125 mg, 0.529 mmol) in pyridine (10 mL) at room temperature was added neat methanesulfonyl chloride (50 µL, 0.64 mmol). After stirring overnight at room temperature, the reaction was diluted with water. Column chromatography afforded 152 mg (91%) of the title compound as white solid, mp 136° C. $^1$H NMR (CDCl$_3$): δ 8.06 (d, J=3.0 Hz, 1H), 7.84 (d, J=8.7 Hz, 2H), 7.37 (t, J=8.7 Hz, 2H), 7.14 (t, J=7.5 Hz, 1H)), 7.06 (d, J=8.7 Hz, 2H), 7.06–7.04 (m, 2H), 6.72 (d, J=3.0 Hz, 1H), 3.38 (s, 3H).

EXAMPLE 8

1-[2-(Methanesulfonylamino)ethyl]-5-[4-(4-fluorophenoxy)phenyl]-1H-pyrazole a) 2-[2-[5-[4-(4-Fluorophenoxy)phenyl]pyrazol-1-yl]ethyl]-isoindole-1,3-dione. A solution of 2-[5-[4-(4-fluorophenoxy)phenyl]-pyrazol-1-yl]ethanol (210 mg, 0.704 mmol), triphenylphosphine (249 mg, 0.949 mmol) and phthalimide (149 mg, 1.01 mmol) in 5 mL of dry THF was cooled in an ice-water bath and neat diethyl azodicarboxylate (145 µL, 160 mg, 0.919 mmol) was added dropwise via syringe. The resulting yellow solution was stirred at room temperature overnight. TLC (9:1 CH$_2$Cl$_2$/EtOAc) indicated the reaction was not complete and it was allowed to stir at room temperature for an additional 24 hours. The reaction was then cooled in an ice-water bath and quenched with a brine solution. Water was added and the aqueous layer was separated and washed with EtOAc (3×5 mL). The pooled organic layers were washed with brine, dried (Na$_2$SO$_4$), filtered and concentrated. The crude product was dissolved in 1:1 EtOAc/hexane with a minimum of CH$_2$Cl$_2$ added to give a clear solution. The resulting solution was added to 11 cm of flash silica gel in a 4 cm diameter column. Elution with 1:1 EtOAc/hexane afforded 218 mg of the desired product contaminated with 1,2-bis(ethoxycarbonyl) hydrazine. Column chromatography (silica gel, 9:1 CH$_2$Cl$_2$/EtOAc) afforded 196 mg (65%) of pure product, mp 126–127° C. $^1$H NMR (CDCl$_3$): δ 7.76–7.64 (m, 4H), 7.48 (d, 1H, J=2 Hz), 7.17 (d, 2H, J=8 Hz), 7.10–6.99 (m, 4H), 6.82 (d, 2H, J=8 Hz), 6.20 (d, 1H, J=2 Hz), 4.49 (t, 2H, J=7 Hz), 3.96 (t, 2H, J=7 Hz).

b) 1-[2-(Methanesulfonylamino)ethyl]-5-[4-(4-fluorophenoxy)phenyl]-1H-pyrazole. A suspension of 2-[2-[5-[4-(4-fluorophenoxy)phenyl]pyrazol-1-yl]ethyl]-isoindole-1,3-dione (126 mg, 0.295 mmol) in 3 mL of a 2M solution of MeNH$_2$ in MeOH was stirred at room temperature for 48 hours. The reaction was then conc. to dryness. Column chromatography (34 cm of flash silica gel in a 2 cm dia. column; eluted with 9:1 CHCl$_3$/MeOH) afforded 36 mg of the desired amine. A solution of this amine (34 mg, 0.12 mmol) in 1 ml, of pyridine was treated with neat methanesulfonyl chloride (22 µL, 32 mg, 0.28 mmol) added via syringe. After stirring overnight, an additional 50 µL (74 mg, 0.65 mmol) of methanesulfonyl chloride was added dropwise via syringe. After stirring overnight, the reaction was diluted with EtOAc and extracted with an aqueous 1M HCl solution (1×15 mL and 1×5 mL). The aqueous layer was back extracted with EtOAc and the combined EtOAc layers were washed with water and brine, dried (Na$_2$SO$_4$), filtered and concentrated. The residue was added to 4.5 g of flash silica gel in a 1 cm diameter column. Elution with 140 ml, of 3:1 EtOAc/hexane afforded 43 mg (95%) of the title compound as a light yellow solid, mp 96–98° C. $^1$H NMR (CDCl$_3$): δ 7.53 (d, 1H, J=2.1 Hz), 7.32 (d, 2H, J=8.7 Hz), 7.10–7.05 (m, 4H), 7.25 (d, 2H, J=9 Hz), 6.29 (d, 1H, J=1.8 Hz), 5.45 (br t, 1H, J=6 Hz), 4.26 (m, 2H), 3.59 (m, 2H), 2.89 (s, 3H).

EXAMPLE 9

1-(2-Carbamoyloxyethyl)-5-[4-(4-fluorophenoxy)phenyl]-1H-pyrazole

A solution of 2-[5-[4-(4-fluorophenoxy)phenyl]-pyrazol-1-yl]ethanol (118 mg, 0.40 mmol) in 1 mL of toluene was treated with solid sodium cyanate (2 eq.; 53 mg, 0.82 mmol) added in one portion. The resulting mixture was cooled in an ice-water bath and neat trifluoroacetic acid (60 µL, 89 mg, 0.78 mmol) was added dropwise via syringe. The reaction was stirred at room temperature. After 2 hours, the reaction had completely solidified and an additional 1 mL of toluene was added. After stirring overnight, the reaction was recooled to 0° C. and diluted with 3 mL of a saturated aqueous NaHCO$_3$ solution. The aqueous layer was separated and extracted with EtOAc (3×5 mL). The organic layers were combined, washed with brine, dried (Na$_2$SO$_4$), filtered and concentrated. Column chromatography (13 cm of flash silica in a 2 cm diameter column eluted with 600 mL of 3:2 CH$_2$Cl$_2$/EtOAc) afforded 21 mg (15%) of the carbamate as a solid, mp 120–125° C. $^1$H NMR (CDCl$_3$): δ 7.57 (d, 1H, J=2 Hz), 7.35 (d, 2H, J=9 Hz), 7.10–7.05 (m, 4H), 7.02 (d, 2H, J=9 Hz), 6.26 (d, 1H, J=2 Hz), 4.60 (br s, 2H), 4.43 (t, 2H), 4.35 (t, 2H).

EXAMPLE 10

3-[4-(4-Fluorophenylthio)phenyl]-1H-pyrazole a) 4-Acetyl-4'-fluoro-diphenyl thioether. A mixture of 4'-fluoroacetophenone (0.98 g, 7.1 mmol), 4-fluorothiophenol (1.0 g, 7.8 mmol) and K$_2$CO3 (0.88 g, 6.4 mmol) was heated in 50 mL N,N-dimethylacetamide at 155° C. for 15 hours. After cooling to room temperature, the reaction was quenched with 50 mL of water. Chloroform (2×50 mL) was used to extract the product. The combined organic layers were washed with an aqueous 2 N NaOH solution and brine, dried over Na$_2$SO$_4$ and evaporated. The oil that was obtained was dissolved in 300 ml, of ether and washed four times with water to remove N,N-dimethylacetamide. The ethereal solution was dried over Na$_2$SO$_4$ and evaporated to give 1.9 g of 4-acetyl-4'-fluorodiphenyl thioether as an oil.

b) 3-[4-(4-Fluorophenylthio)phenyl]-1H-pyrazole. A solution of 4-acetyl-4'-fluoro-diphenyl thioether (0.75 g, 3.1 mmol) and N,N-dimethylformarnide dimethylacetal (0.47 mL, 3.4 mmol) in 6 mL of DMF was heated at 155° C. overnight. Once at room temperature, the solution was poured into 30 mL of water. EtOAc (2×100 mL) was used to extract the product. The combined organic layers were washed with water three times, dried over Na$_2$SO$_4$ and evaporated to yield 0.85 g of a dark-brown oil. A solution of the oil in 6 mL of EtOH containing hydrazine-hydrate (0.47 mL, 15.3 mmol) was heated at reflux for 1.5 h. After cooling to room temperature, 30 mL of water was poured into the reaction mixture. EtOAc (2×75 mL) was used to extract the product. The organic layer was separated, washed with water, dried over Na$_2$SO$_4$ and evaporated. The crude product was purified on a silica gel column, eluting with 40% EtOAc/hexane, to yield 0.65 g (79%) of the title compound as a yellow oil, TLC $R_f$=0.45 (1:1 EtOAc/hexane). $^1$H NMR (300 MHz, DMSO-d$_6$): δ 12.95 (s, 1H, NH), 7.83 (br s, 1H), 7.81, 7.44 and 7.29 (m, 8H, PhH), 6.72 (br s, 1H).

EXAMPLE 11

3-[4-(4-Fluorophenylthio)phenyl]-1H-pyrazole-1-carboxamide

A solution of 3-[4-(4-fluorophenylthio)phenyl]-1H-pyrazole (85 mg, 0.31 mmol) in 1.5 mL glacial acetic acid was treated with a solution of sodium cyanate (31 mg, 0.47 mmol) in 0.5 mL of water. The resulting white suspension was stirred at room temperature overnight. The suspension was then diluted with 10 mL of EtOAc, resulting in a yellow solution which was washed with water and sat. NaHCO$_3$ solution, dried over Na$_2$SO$_4$ and evaporated. The residue was triturated with 3 mL of 25% EtOAc/hexane. The white solid that formed was collected by filtration and dried to give 65 mg (66%) of the title compound, mp 150–155° C. (TLC $R_f$=0.22 (25% EtOAc/hexane)). $^1$H NMR (300 MHz, CDCl$_3$): δ 8.27 (d, J=2.1 Hz, 1H, pyrazole H), 7.77 (d, J=7.5 Hz, 2H, PhH), 7.48–7.06 (m, 6H, PhH), 6.71 (d, J=2.1 Hz, 1H, pyrazole H), 5.31 (br s, 2H, NH$_2$).

EXAMPLE 12

2-[5-[4-(4-Fluorophenoxy)phenyl]-pyrazol-1-yl]ethanol

A solution of 3-dimethylamino-1-[4-(4-fluorophenoxy)phenyl]-propenone (1.00 g, 3.50 mmol) and 2-hydroxyethylhydrazine (307 mg, 4.03 mmol) in 8 mL of EtOH was heated at reflux for 2 hours. TLC indicated incomplete reaction and an additional 88 mg (1.12 mmol) of the hydrazine was added. After 3.5 hours at reflux, the reaction was allowed to cool and concentrated in vacuo. The residue was dissolved in EtOAc and added to 12.5 cm of flash silica gel in a 4 cm diameter column. Elution with 100% EtOAc afforded 920 mg (88%) of the product as a 10:1 mixture of 1,5- and 1,3-isomers. The mixture (900 mg) was suspended in 5 mL of pyridine, cooled in an ice-water bath and treated with neat acetic anhydride (355 μL, 384 mg, 3.76 mmol) added dropwise via syringe. The resulting clear solution was stirred at room temperature overnight. The reaction was cooled in an ice-water bath and added to 35 mL of an ice-cold aqueous 2N HCl solution and 30 mL of EtOAc. The organic layer was washed with a saturated aqueous NaHCO$_3$ solution and brine. After drying (Na$_2$SO$_4$), the solvent was removed in vacuo. Column chromatography (12 cm of flash silica in a 4 cm diameter column, elution with 600 mL of 5% EtOAc/CH$_2$Cl$_2$ and 200 mL of 10%, 300 mL of 15% and 100 mL each of 20 and 30% EtOAc/CH$_2$Cl$_2$) afforded 737 mg of the desired 1,5-pyrazole (Rf 5% EtOAc/CH$_2$Cl$_2$ 0.28) and 100 mg of the 1,3-isomer (Rf 5% EtOAc/CH$_2$Cl$_2$ 0.52).

To a solution of the 1,5-isomer (719 mg, 2.11 mmol) in 10 mL of MeOH cooled in an ice-water bath was added solid K$_2$CO$_3$ (283 mg, 2.05 mmol) in one portion. After stirring for 1 hour, 1.3 ml, of a 2N aqueous HOAc solution was added dropwise via syringe. The reaction was then added to 25 mL of water. The resulting mixture was extracted with EtOAc (3×25 mL). The EtOAc layers were pooled and washed with brine, dried (Na$_2$SO$_4$), filtered and concentrated to dryness. The light yellow oil that formed was triturated with hexane giving 555 mg (88%) of the title compound as a light yellow solid, mp 71–72° C. $^1$H NMR (CDCl$_3$): δ 7.55 (d, 1H, J=1.8 Hz), 7.35 (d, 2H, J=7.0 Hz), 7.10–7.00 (m, 6H), 6.29 (d, 1H, J=1.8 Hz), 4.20 (m, 2H), 4.00 (m, 2H), 3.72 (t, 1H, J=6.2 Hz).

EXAMPLE 13

3-[4-(4-Fluorophenoxy)phenyl]-1H-pyrazole-1-carboxylic Acid Dimethylamide

A solution of 3-[4-(4-fluorophenoxy)phenyl]-1H-pyrazole (467 mg, 1.84 mmol) in 7 mL of THF containing 0.3 mL (2.13 mmol) of triethylamine was treated with 0.3 mL (3.2 mmol) dimethylcarbamyl chloride added via syringe. No reaction was observed at room temperature. An additional 0.3 mL of dimethylcarbamyl chloride was added and the reaction was heated at reflux overnight. The reaction was then added to a saturated aqueous NaHCO$_3$ solution and EtOAc. The aqueous layer was washed with EtOAc and the pooled organic layers were dried (Na$_2$SO$_4$), filtered and concentrated to dryness. Column chromatography (7/3 hexane/EtOAc) afforded 282 mg of the title compound as a yellow oil that solidified on standing, mp 59–63° C. $^1$H NMR (CDCl$_3$): δ 8.15 (d, 1H, J=2.7 Hz), 7.80 (d, 2H, J=8.4 Hz), 7.06–6.88 (m, 6H), 6.62 (d, 1H, J=2.7 Hz), 3.30 (br s, 6H).

EXAMPLE 14

1-Benzyl-5-[4-(4-fluorophenoxy)phenyl]-1H-pyrazole

To a solution of 3-dimethylamino-1-[4-(4-fluorophenoxy)phenyl]-propenone (580 mg, 2.04 mmol) in EtOH was added benzyl hydrazine dihydrochloride (500 mg, 2.49 mmol). The reaction was heated at reflux until TLC showed complete consumption of the starting enone. The resulting mixture was allowed to cool to room temperature and was added to water/EtOAc. The aqueous layer was separated and extracted with EtOAc. The combined EtOAc layers were dried (Na$_2$SO$_4$), filtered and concentrated in vacuo. Purification by column chromatography (gradient from 9:1 to 8:2 hexane/EtOAc) gave 220 mg of the title compound as an oil. $^1$H NMR (CDCl$_3$): δ 7.59 (d, 1H, J=1.5 Hz), 7.30–6.90 (m, 13H), 6.32 (d, 1H, J=1.8 Hz), 5.34 (s, 2H).

EXAMPLE 15

2-[3-[4-(4-Fluorophenoxy)phenyl]-2H-pyrazol-2-yl]-pyrrolidin-1-yl Ethanone

A solution of [5-(4-fluorophenoxy)phenyl)pyrazol-1-yl]-acetic acid ethyl ester (104 mg, 0.306 mmol) in 1 mL of MeOH was treated with neat pyrrolidine (0.1 mL, 85 mg, 1.20 mmol). After stirring at room temperature for 4 days, the reaction was concentrated to dryness. The solid residue was triturated with hexane, affording 80 mg (71%) of the amide as a solid, mp 90–95° C. $^1$H NMR (CDCl$_3$): δ 7.58 (br s, 1H), 7.46 (d, 2H, J=8.7 Hz), 7.10–6.98 (m, 6H), 6.30 (br s, 1H), 3.51 (t, 2H, J=6.6 Hz), 3.44 (t, 2H, J=6.9 Hz), 1.98 (p, 2H, J=6.6 Hz), 1.85 (p, 2H, J=6.6 Hz).

EXAMPLE 16

2-(N-methylacetamido)-3-[4-(4-fluorophenoxy)phenyl]-2H-pyrazole

The methyl amide was prepared similarly by allowing [5-(4-fluorophenoxy)phenyl)pyrazol-1-yl]-acetic acid ethyl ester to react with methylamine in MeOH, mp 132–135° C. $^1$H NMR (CDCl$_3$): δ 7.64 (d, 1H, J=1.8 Hz), 7.28 (d, 2H, J=8.7 Hz), 7.10–7.00 (m, 4H), 7.01 (d, 2H, J=8.7 Hz), 6.38 (br s, 1H), 6.35 (d, J=1.8 Hz), 4,77 (s, 2H), 2.83 (d, 3H, J=5.4 Hz).

The following amides were prepared using the procedure described for the methyl amide:

2-{5-[4-(4-Fluorophenoxy)phenyl]-pyrazol-1-yl}-1-(4-methyl)piperazine-1-yl-ethanone; $R_f$ 0.30 (10:1 $CH_2Cl_2$/MeOH); $^1$H NMR (300 MHz, $CDCl_3$): δ 7.61 (d, J=1.8 Hz, 1H), 7.44 (d, J=9.0 Hz, 2H), 7.10–7.01 (m, 6H), 6.34 (d, J=1.8 Hz, 1H), 4.96 (s, 2H), 3.68–3.65 (m, 2H), 3.51–3.48 (m, 2H), 2.42 (t, J=5.0 Hz, 4), 2.33 (s, 3H).

1-{5-[4-(4-Fluorophenoxy)phenyl]-pyrazol-1-yl}-2-methyl-propane-2-ol; $R_f$ 0.59 (100% EtOAc); $^1$H NMR (300 MHz, $CDCl_3$): δ 7.60 (d, J=1.8 Hz, 1H), 7.35–7.28 (m, 2H), 7.11–7.03 (m, 6H), 6.32 (d, J=1.8 Hz, 1H), 5.17 (s, 1H), 4.06 (s, 2H), 1.06 (s, 6H).

1-{5-[4-(4-Fluorophenoxy)phenyl]-pyrazol-1-yl}-propane-2-one; $R_f$ 0.53 (EtOAc); $^1$H NMR (300 MHz, $CDCl_3$): δ 7.63 (d, J=1.8 Hz, 1H), 7.31–7.28 (m, 2H), 7.13–7.01 (m, 6H), 6.37 (d, J=1.8 Hz, 1H), 4.91 (s, 2H), 2.09 (s, 3H).

1-Morpholin-4-yl-2-{5-[4-(4-fluorophenoxy)phenyl]-pyrazol-1-yl}-ethanone; $R_f$ 0.40 (19:1 $CHCl_3$/MeOH); mp 122–124° C.; $^1$H NMR (300 MHz, $CDCl_3$): δ 7.61 (d, J=1.8 Hz, 1H), 7.46 (d, J=9.0 Hz, 2H), 7.13–7.02 (m, 6H), 6.34 (d, J=1.5 Hz, 1H), 4.96 (s, 2H), 3.69–3.66 (m, 6H), 3.51–3.50 (m, 2H).

EXAMPLE 17

2-{5-[4-(4-Fluorophenoxy)phenyl]-pyrazol-1-yl}-acetamide

To a solution of 3-dimethylamino-1-[4-(4-fluorophenoxy)phenyl]-propenone (860 mg, 3.0 mmol) in EtOH was added ethyl hydrazinoacetate hydrochloride (580 mg, 3.64 mmol) as a solid in one portion. After 1 hour at reflux, the reaction was allowed to cool and was partitioned between water and EtOAc. The aqueous layer was extracted with EtOAc and the combined EtOAc layers were dried ($Na_2SO_4$), filtered and concentrated in vacuo. Column chromatography (2% EtOAc/$CH_2Cl_2$) gave the desired ethyl ester (1,5-isomer; Rf 0.28 5% EtOAc/$Cl_2C_2$) and its 1,3-isomer (Rf 0.68 EtOAc/$CH_2Cl_2$). A solution of the 1,5-isomer in MeOH was treated with an aqueous $NH_4OH$ solution and stirred at room temperature for 48 hours. Work-up after described for the ethyl ester and column chromatography (100% EtOAc) gave 276 mg of the title compound as a white solid, mp 168–169° C. $^1$H NMR ($CDCl_3$): δ 7.65 (d, 1H, J=1.8 Hz), 7.31 (d, 2H, J=8.7 Hz), 7.10–7.00 (m, 6.35 (d, 1H, J=1.8 Hz), 6.30 (br s, 1H), 5.56 (br s, 1H), 4.78 (s, 2H).

EXAMPLE 18

2-{3-[4-(4-Fluorophenoxy)phenyl]-pyrazol-1-yl}-acetamide

Reaction of the 1,3-isomer using the method described in example 17 for its 1,5-isomer gave 35 mg of the title compound as a white solid, mp 145° C. $^1$H NMR ($CDCl_3$): δ 7.76 (d, 2H, J=9 Hz), 7.49 (d, 1H, J=2.1 Hz), 7.05–6.99 (m, 6H), 6.59 (d, 1H, J=2.4 Hz), 6.40 (br s, 1H), 5.45 (br s, 1H), 4.83 (s, 3H).

EXAMPLE 19

3-{5-[4-(4-Fluorophenoxy)phenyl}-pyrazol-1yl}-propionamide

Reaction of 3-dimethylamino-1-[4-(4-fluorophenoxy)phenyl]-propenone with 2-cyanoethylhydrazine as described above gave 1-(2-cyanoethyl)-5-[4-(4-fluorophenoxy)phenyl]pyrazole. Reaction of a solution of the nitrile with 10 mL of a 20% aqueous KOH solution and 4 mL of an aqueous 30% $H_2O_2$ solution at reflux gave 64 mg of the amide as a white solid, mp 118–120° C. $^1$H NMR ($CDCl_3$): δ 7.54 (d, 1H, J=1.8 Hz), 7.35 (d, 2H, J=8.7 Hz), 7.10–6.98 (m, 61H), 6.26 (d, 1H, J=1.8 Hz), 6.08 (br s, 1H), 5.30 (br s, 1H), 4.39 (t, 2H, J=6.6 Hz), 2.86 (t, 3H, J=6.6 Hz).

EXAMPLE 20

2-{3-[4-(4-Fluorophenoxy)phenyl]-pyrazol-1-yl}-pyrimidine

To a solution of 3-[4-(4-fluorophenoxy)phenyl]-1H-pyrazole (930 mg, 3.66 mmol) in 15 mL of dry THF was slowly added 240 mg (6.00 mmol) of NaH. After stirring at room temperature for 20 minutes, 500 mg (4.15 mmol) of 2-chloropyrimidine was added in one portion. The reaction was allowed to stir overnight at room temperature and concentrated to dryness. The residue was dissolved in $CHCl_3$ and subjected to flash chromatography. Elution with 3:2 hexane/EtOAc gave 994 mg of the title compound as a solid, mp 123–125° C. $^1$H NMR ($CDCl_3$): δ 8.77 (d, 2H, J=4.8 Hz), 8.65 (d, 1H, J=3.0 Hz), 7.95 (d, 2H, J=8.7 Hz), 7.20 (t, 1H, J=4.9 Hz), 7.07–6.98 (m, 5H), 6.78 (d, 1H, J=3.0 Hz).

The following compound was prepared using a similar procedure but using 3-[4-(4-trifluoromethylphenoxy)phenyl]-1H-pyrazole:

2-{3-[4-(4-Trifluoromethylphenoxy)phenyl]pyrazol-1-yl}pyrimidine, mp 141–144° C.

EXAMPLE 21

4-[4-(4-Fluorophenoxy)phenyl]-1H-imidazole a) 1-[4-(4-Fluorophenoxy)phenyl]ethanone. A mixture of 4-fluorophenol (4.45 g, 39.3 mmol), 4-fluoroacetophenone (4.4 mL, 36 mmol), and potassium carbonate (13 g, 94 mmol) in DMF (40 mL) was refluxed overnight. The mixture was allowed to cool to room temperature, then partitioned between ethyl acetate (200 mL) and water (200 mL). The separated aqueous layer was extracted with ethyl acetate (3×100 mL). The combined ethyl acetate layers were washed with an aqueous sodium hydroxide solution (2N, 200 mL), washed twice with water (200 mL each), dried over sodium sulfate, filtered, and evaporated under reduced pressure to give a dark oil. The oil solidified on standing at room temperature overnight. The weight of crude 1-[4-(4-fluorophenoxy)phenyl]ethanone was 6.7 g (80%). $^1$H NMR ($CDCl_3$): δ 7.96 (d, J=9.0 Hz, 2H), 7.11–7.06 (m, 4H), 6.98 (d, J=8.7 Hz, 2H), 2.59 (s, 3H).

b) 2-Bromo-1-[4-(4-fluorophenoxy)phenyl]ethanone. To a solution of 1-[4-(4-fluorophenoxy)phenyl]ethanone (2.1 g, 9.1 mmol) and aqueous hydrobromic acid (3 drops) in methanol (50 mL) was added dropwise a solution of bromine (0.6 mL, 11.6 mmol) in methanol (20 mL). After the addition, the solution was stirred at room temperature overnight. The solution was then partitioned between water and ethyl acetate. The separated aqueous layer was extracted one more time with ethyl acetate. The combined ethyl acetate layers were dried over sodium sulfate, filtered, and evaporated under reduced pressure to give oil, which solidified on standing (2.5 g, 87%). $^1$H NMR ($CDCl_3$): δ 7.96 (d, J=9.0 Hz, 2H), 7.10–7.06 (m, 4H), 6.98 (d, J=9.0 Hz, 2H), 4.39 (s, 2H).

c) 4-[4-(4-Fluorophenoxy)phenyl]-1H-imidazole. A solution of 2-bromo-1-[4-(4-fluorophenoxy)phenyl]ethanone (0.547 g, 17.7 mmol) in formamide (25 mL) was refluxed at 190° C. for 1 hour. The solution was allowed to cool to room temperature and partitioned between water and ethyl acetate. The organic layer was washed 3 times with water, dried over sodium sulfate, filtered, and evaporated under reduced pressure to give an oil. The oil was purified by column chromatography (flash silica gel, 9:1 ethyl acetate/methanol) to give 94 mg (21%) of the title compound, mp 165–168° C. $^1$H NMR (DMSO-d$_6$): δ 7.76 (d, J=8.4 Hz, 2H), 7.71 (s, 1H), 7.52 (s, 1H), 7.23 (t, J=9.0 Hz, 2H), 7.07 (dd, J=8.5, 4.9 Hz, 2H), 6.99 (d, J=8.4 Hz, 2H).

The following compounds were prepared similarly:

4-[4-(4-Fluorophenoxy)-3-fluorophenyl]-1H-imidazole; $^1$H NMR (CDCl$_3$): δ 7.70 (s, 1H), 7.56 (dd, J=2.0, 12.0 Hz, 1H), 7.46 (dd, J=1.2, 8.4 Hz, 1H), 7.30 (s, 1H), 7.04–6.93 (m, 5H).

4-[4-(4-Fluorophenoxy)-3-fluorophenyl]-1H-imidazole, hydrochloride salt; the free base prepared above was dissolved in chloroform and a 1N solution of HCl in ether was added until precipitation occurred. The mixture was evaporated under reduced pressure to afford the salt. $^1$H NMR (DMSO-d$_6$): δ 14.8 (bs, 2H), 9.16 (s, 1H), 8.17 (s, 1H), 7.97 (d, J=11.7 Hz, 1H), 7.71 (d, J=9.0 Hz, 1H), 7.25 (t, J=8.4 Hz, 3H), 7.11 (dd, J=4.5, 8.7 Hz, 2H).

4-[4-(2,4-Difluorophenoxy)phenyl]-1H-imidazole; $^1$H NMR (CDCl$_3$): δ 7.65 (d, J=8.4 Hz, 2H), 7.66 (s, 1H), 7.26 (s, 1H), 7.09–7.01 (m, 1H), 6.97–6.90 (m, 1H), 6.94 (d, J=9.0 Hz, 2H), 6.98–6.80 (m, 1H); mp 144–148° C.

4-[4-(2,4-Difluorophenoxy)phenyl]-1H-imidazole, hydrochloride salt; $^1$H NMR (DMSO-d$_6$): δ 9.24 (s, 1H), 8.14 (s, 1H), 7.95 (d, J=8.4 Hz, 2H), 7.56–7.48 (m, 1H), 7.42–7.34 (m, 1H), 7.21–7.15 (m, 1H), 7.09 (d, J=8.7 Hz, 2H); mp 192–195° C.

4-[4-(4-Chloro-2-fluorophenoxy)phenyl]-1H-imidazole, hydrochloride salt; $^1$H NMR (DMSO-d$_6$): δ 9.24 (s, 1H), 8.14 (s, 1H), 7.96 (d, J=8.7 Hz, 2H), 7.67 (dd, J=10.5, 1.8 Hz, 1H), 7.37–7.26 (m, 2H), 7.14 (d, J=8.4 Hz, 2H); mp 216–220° C.

4-(4-(4-Trifluoromethylphenoxy)phenyl]-1H-imidazole, hydrochloride salt; $^1$H NMR (DMSO-d$_6$): δ 15.0 (bs, 2H), 9.25 (s, 1H), 8.18 (s, 1H), 7.98 (d, J=8.4 Hz, 2H), 7.77 (d, J=9.0 Hz, 2H), 7.29 (d, J=8.7 Hz, 2H), 7.21 (d, J=8.7 Hz, 2H); mp 230–232° C. The intermediate 1-[4-(4-trifluoromethylphenoxy)phenyl]ethanone was prepared from 4-hydroxyacetophenone and 4-fluorobenzotrifluoride using the method described for the synthesis of 1-[4-(4-fluorophenoxy)phenyl]ethanone.

EXAMPLE 22

4-[4-(2,4-Difluorophenoxy)phenyl]-2-methyl]-1H-imidazole

A solution of acetamidine hydrochloride (120 mg, 1.71 mmol) in DMF was treated with 2 mL (2.0 mmol) of a 1M solution of potassium tert-butoxide in THF. The resulting mixture was heated at 95° C. for 1 hour. Solid 2-bromo-1-[4-(4-fluorophenoxy)-3-fluorophenyl]ethanone (prepared as described for 2-bromo-1-[4-(4-fluorophenoxy)phenyl]ethanone; 345 mg, 1.00 mmol) was added and the reaction was stirred at 95° C. overnight. Once at room temperature, the mixture was partitioned between water and EtOAc. The separated aqueous layer was extracted once with EtOAc and the pooled organic layers were washed with water (3×), dried (Na$_2$SO$_4$), filtered and concentrated. Column chromatography (100% EtOAc) gave 86 mg of the imidazole as a solid, TLC R$_f$0.54 (5% MeOH/EtOAc). $^1$H NMR (CDCl$_3$): δ 7.53 (dd, 1H, J=11.9, 1.6 Hz), 7.43 (d, 1H, J=8.4 Hz), 7.16 (s, 1H), 7.03–6.92 (m, 5H), 2.47 (s, 3H).

EXAMPLE 23

4-[4-(2,4-Difluorophenoxy)phenyl]-1-methyl-1H-imidazole-2-carboxamide a) 2-Cyano-4-[4-(2,4-difluorophenoxy)phenyl]-1-methyl-1H-imidazole. A mixture of crude 4-[4-(2,4-difluorophenoxy)phenyl]-1H-imidazole (prepared from 4.14 g of 2-bromo-1-[4-(2,4-difluorophenoxy)phenyl]ethanone and 35 mL of formamide as described above), solid KOH (2.57 g) and MeI (1 mL) was heated at reflux overnight. After filtration, the reaction was concentrated to dryness and the residue was purified by flash chromatography, affording 4-[4-(2,4-difluorophenoxy)phenyl]-1-methyl-1H-imidazole as a solid. A solution of 4-(dimethylamino)pyridine (1.34 g, 10.9 mmol) in 30 mL of dry DMF at –10° C. was added cyanogen bromide (5.0 M solution in MeCN; 2.1 mL, 10.5 mmol), giving a pale yellow precipitate. Solid 4-[4-(2,4-difluorophenoxy)phenyl]-1-methyl-1H-imidazole (1.39 g, 4.86 mmol) was added and the reaction was heated at 60° C. overnight. The reaction was allowed to cool to room temperature and added to water and EtOAc. The separated aqueous layer was extracted twice with EtOAc and the pooled organic layers were washed with water (3×), dried (Na$_2$SO$_4$), filtered and concentrated. The oily residue was purified by flash chromatography (gradient from 8.5/2.5 to 7/3 hexane/EtOAc) affording 713 mg of 2-cyano-4-[4-(2,4-difluorophenoxy)phenyl]-1-methyl-1H-imidazole as a solid, mp 109–110° C. (Rf 0.42, 7/3 hexane/EtOAc) along with 122 mg of 4-cyano-4-[4-(2,4-difluorophenoxy)phenyl]-1-methyl-1H-imidazole, mp 169–170° C. (Rf 0.32, 7/3 hexane/EtOAc). $^1$H NMR (2-cyano; CDCl$_3$): δ 7.65 (d, 2H, J=9.0 Hz), 7.16 (s, 1H), 7.06 (dt, 1H, J=9.3, 5.4 Hz), 6.93 (d, 2H, J=8.7 Hz), 6.98–6.80 (m, 2H), 3.65 (s, 3H). $^1$H NMR (4-cyano; CDCl$_3$): δ 7.69 (d, 2H, J=8.7 Hz), 7.27 (s, 1H), 7.09 (dt, J=8.7, 5.7 Hz), 6.96 (d, 2H, J=8.7 Hz), 7.00–6.82 (m, 2H), 3.90 (s, 3H).

b) 4-[4-(2,4-Difluorophenoxy)phenyl]-1-methyl-1H-imidazole-2-carboxamide. A mixture of 2-cyano-4-[4-(2,4-difluorophenoxy)phenyl]-1-methyl-1H-imidazole (0.40 g, 1.27 mmol), ethylenediamine (0.3 mL, 4.5 mmol), p-toluenesulfonic acid monohydrate (110 mg, 0.58 mmol) in ethylene glycol was heated at reflux for 20 hours. Work-up as described above and column chromatography (gradient from 100% EtOAc to 5% MeOH/EtOAc) gave 47 mg of the title compound as a yellow solid, mp 183–187° C. $^1$H NMR (CDCl$_3$): δ 10.44 (br s, 1H), 7.38 (d, 2H, J=9.0 Hz), 7.10–6.80 (m, 5H), 6.40 (s, 1H), 3.32 (s, 3H).

EXAMPLE 24

2-[4-(4-Fluorophenoxy)phenyl]-1H-imidazole

A mixture of 4-(4-fluorophenoxy)benzonitrile (720 mg, 3.38 mmol), ethylenediamine (0.3 mL, 4.4 mmol) and p-toluenesulfonic acid monohydrate (420 mg, 2.20 mmol) in ethylene glycol was heated at reflux for 48 hours. Once at room temperature, the reaction was added an aqueous 2N NaOH solution. The resulting precipitate was isolated by filtration and was carried on without further purification. A solution of the imidazoline (0.53 g, 2.0 mmol) in 20 mL of toluene was treated with 10% Pd/C (0.53 g) and heated at reflux for 40 hours. The reaction was partitioned between 100 mL of EtOAc and 200 mL of an aqueous 2N NaOH solution. The separated organic layer was filtered through a bed of Celite and evaporated to give a solid. A solution of the free base in MeOH was treated with HCl/ether and evaporated to give the hydrochloride salt, mp 86–91° C. $^1$H NMR (DMSO-$d_6$): δ 14.8 (br s, 2H), 8.11 (d, 2H, J=8.7 Hz), 7.76 (s, 2H), 7.31 (t, 2H, J=8.9 Hz), 7.22–7.19 (m, 2H), 7.19 (d, 2H, J=9.0 Hz).

EXAMPLE 25

2-[4-(4-Fluorophenoxy)phenyl]-1H-benzimidazole

A mixture of 4-(4-fluorophenyl)benzoic acid (190 mg, 0.88 mmol) and phenylenediamine (133 mg, 1.22 mmol) in 25 g of polyphosphoric acid was heated at 150° C. overnight. Once at room temperature, the reaction was diluted with water. The resulting solid was washed with water, dried and chromatographed (gradient from 8/2 to 7/3 hexane/EtOAc) affording 104 mg (39%) of the benzimidazole as a solid, mp 243–245° C. $R_f$0.40 7/3 hexane/EtOAc. $^1$H NMR (DMSO-$d_6$): δ 12.8 (s, 1H), 8.16 (d, J=8.4 Hz, 2H), 7.61 (m, 1H), 7.49 (m, 1H), 7.29 (t, J=8.4 Hz, 2H), 7.20–7.16 (m, 4H), 7.12 (d, J=8.4 Hz, 2H).

EXAMPLE 26

2-[4-(4-Fluorophenoxy)phenyl]-1H-imidazole-4-carboxamide

To a solution of 0.56 g (6.83 mmol) of sodium acetate in 10 mL of water was added 1.29 g (4.78 mmol) of 1,1-dibromo-3,3,3-trifluoroacetone. The resulting solution was warmed for 30 minutes and then cooled in an ice/water bath. A solution of 4-(fluorophenoxy)benzaldehyde (789 mg, 3.65 mmol) in MeOH was added, followed by 10 mL of a concentrated aqueous NH$_4$OH solution. Additional MeOH was added until a homogenous solution formed. After stirring at room temperature overnight, the reaction was diluted with water. The precipitate that formed was collected, washed with water and dried. Column chromatography (gradient from 8/2 to 2/3 hexane/EtOAc) afforded 0.6 g of a solid. A mixture of 0.5 g of the solid and 80 mL of a concentrated aqueous NH$_4$OH solution was diluted with MeOH until a solution formed. The reaction was heated in a sealed tube for 1.5 days. After cooling to room temperature, the mixture was added to a water/EtOAc mixture. The aqueous layer was extracted with EtOAc and the combined organic layers were washed with water, dried (Na$_2$SO$_4$), filtered and concentrated to dryness. Column chromatography (1:1 hexane/EtOAc) gave 2-[4-(4-fluorophenoxy)phenyl]-1H-imidazole-4-carbonitrile as a solid. $^1$H NMR (DMSO-$d_6$): δ 13.37 (br s, 1H), 8.23 (s, 1H), 7.95 (d, 2H, J=8.7 Hz), 7.27 (t, 2H, J=8.9 Hz), 7.15 (dd, 2H, J=9.3, 4.5 Hz), 7.08 (d, 2H, J=8.7 Hz). To a solution of the nitrile in EtOH was added 1 g of KOH dissolved in 5 ml of water and 1.5 mL of a 30% aq. H$_2$O$_2$ solution. After heating at reflux for 3 hours, the reaction was added to water/EtOAc. The organic layer was dried (Na$_2$SO$_4$), filtered and evaporated in vacuo. The residue was subjected to flash chromatography (100% EtOAc) affording the title compound as a white solid, TLC $R_f$0.34 (5% MeOH/EtOAc). $^1$H NMR (CDCl$_3$): δ 12.90 (br s, 1H), 8.08 (br s, 1H), 7.97 (d, 2H, J=9.0 Hz), 7.70 (s, 1H), 7.63 (br s, 1H), 7.26 (t, 2H, J=8.7 Hz), 7.15–7.10 (m, 2H), 7.07 (d, 2H, J=8.7 Hz).

EXAMPLE 27

5-[4-(4-Fluorophenoxy)phenyl]-pyrrole-2-carboxamide a) 5-(Butoxycarbonyl)-1-(tert-butoxycarbonyl)-2-pyrrolidone. To a solution of butyl 2-pyrrolidone-5-carboxylate (Aldrich; 7.41 g, 40 mmol) in dry CH$_2$Cl$_2$ (150 mL) was added di-tert-butyl dicarbonate (13.5 g, 61.5 mmol) and Et$_3$N (12 mL). After stirring at room temperature for 3 days, the reaction was concentrated to dryness. The resulting residue was chromatographied (hexane-EtOAc, 1:1) affording 9.8 g (86%) of 5-(butoxycarbonyl)-1-(tert-butoxycarbonyl)-2-pyrrolidone as a yellowish oil. $^1$H NMR (CDCl$_3$): δ 4.63 (dd, 1H, J=9 Hz, 3 Hz), 4.19 (t, 2H, J=7 Hz), 2.72–2.27 (m, 2H), 2.10–2.00 (m, 2H), 1.69–1.62 (m, 2H), 1.52 (s, 9H), 1.48–1.37 (m, 2H), 0.96 (t, 3H, J=7.5 Hz).

b) 4-Fluorodiphenyl ether. A mixture of 4-fluorophenol (5.6 g, 50 mmol), potassium tert-butoxide (5.6 g, 50 mmol), bromobenzene (7.85 g, 50 mmol) and copper powder (2 g) in DMSO (20 mL) was refluxed for 18 hours, allowed to cool to room temperature, diluted with EtOAc (150 mL), and filtered. The filtrate was evaporated and the residue was chromatographed (hexane) to give 6.0 g (63.8%) of the ether as a colorless oil. $^1$H NMR (CDCl$_3$): δ 7.25 (dt, 2H, J=8 Hz, 2.5 Hz), 7.11 (dt, 1H, J=8 Hz, 2.5 Hz), 7.06–6.98 (m, 6H).

c) 4-Bromo-4'-fluorodiphenyl ether. To a solution of 4-fluorodiphenyl ether (6.0 g, 32 mmol) and a crystal of I$_2$ in CS$_2$ (20 mL) cooled in an ice-water bath was slowly added bromine (2 mL). After stirring at room temperature for 16 hours the reaction was concentrated in vacuo and the residue was chromatographed (hexane) to give 7 g (80%) of the ether as a colorless oil. $^1$H NMR(CDCl$_3$): δ 7.46–7.42 (m, 2H), 7.10–6.97 (m, 4H), 6.88–6.84 (m, 2H).

d) Butyl 5-[4-(4-fluorophenoxy)phenyl]-5-keto-2-Boc-amino-pentanoate. To a solution of 4-bromo-4'-fluorodiphenyl ether (3.88 g, 14.5 mmol) in dry THF (60 mL) was added Mg metal (500 mg, 20.6 mmol) and a small piece of I$_2$. The mixture was refluxed for 16 hours and allowed to cooled. The liquid phase was transferred with a syringe into a solution of 5-(butoxycarbonyl)-1-(tert-butoxycarbonyl)-2-pyrrolidone (3.9 g, 13.7 mmol) in dry THF (80 mL) cooled below 0° C. The reaction mixture was stirred at room temperature for 5 hours then at reflux. Once at room temperature, the reaction mixture was treated with 10 mL of 50% AcOH and MeOH (10 mL), stirred for 30 minutes and evaporated. The residue was dissolved in EtOAc (300 mL), washed with brine (2×50 mL), evaporated, and chromatographed (hexane-EtOAc, 7:3) affording 2.4 g (39%) of the desired ester as a colorless oil. $^1$H NMR (CDCl$_3$): δ 7.95 (d, 2H, J=8 Hz), 7.11–6.85 (m, 6H), 4.95–4.90 (m, 1H), 4.20 (t, 2H, J=7 Hz), 3.21–2.94 (m, 2H), 2.35–2.00 (m, 2H), 1.73–1.64 (m, 3H), 1.51 (s, 9H), 1.48–1.36 (m, 2H), 0.95 (t, 3H, J=7.5 Hz).

e) Butyl 5-[4-(4-fluorophenoxy)phenyl]-ρ$^1$-pyrroline-2-carboxylate. To a cooled (ice-water bath) solution of butyl 5-[4-(4-fluorophenoxy)phenyl]-5-keto-2-Boc-aminopentanoate (2.4 g, 5.36 mmol) in dry CH$_2$Cl$_2$ (12 mL) was added trifluoroacetic acid (5 mL). After stirring cold for 2 hours, the reaction was diluted with CH$_2$Cl$_2$ (200 mL). The CH$_2$Cl$_2$ solution was washed with a saturated aqueous NaHCO$_3$ solution, brine, dried (Na$_2$SO$_4$), filtered and evaporated to give 1.69 g (84%) of the desired pyrroline as a yellowish oil. $^1$H NMR(CDCl$_3$): δ 7.87 (d, 2H, J=9 Hz), 7.12–6.80 (m, 5H), 4.95–4.90 (m, 1H), 4.20 (t, 2H, J=7 Hz), 3.21–2.94 (m, 2H), 2.35–2.00 (m, 2H), 1.73–1.64 (m, 3H), 1.48–1.36 (m, 2H), 0.96 (t, 3H, J=7.5 Hz).

f) Butyl 5-[4-(4-fluorophenoxy)phenyl]-pyrrole-2-carboxylate. A solution of pyrroline ester (1.69 g, 4.76 mmol) and 2,3-dichloro-5,6-dicyano-1,4-benzoquinone (DDQ; 1.71 g, 5.16 mmol) in dry CH$_2$Cl$_2$ (100 mL) was stirred at room temperature for 1 hour. A solid that formed was removed by filtration, and the filtrate was evaporated to dryness. The residue was chromatographed (hexane-EtOAc, 4:1) to give 400 mg (24%) of the pyrrole ester as a solid, mp.133–134° C. $^1$H NMR(CDCl$_3$): δ 9.34 (bs, 1H), 7.55 (dd, 2H, J=9 Hz, 2 Hz), 7.11–6.96 (m, 6H), 6.50–6.49 (m, 1H), 4.31 (t, 2H, J=7 Hz), 1.80–1.71 (m, 2H), 1.55–1.42 (m, 2H), 1.00 (t, 3H, J=7.5 Hz).

g) 5-[4-(4-Fluorophenoxy)phenyl]-pyrrole-2-carboxylic acid. To a solution of the pyrrole ester (900 mg, 2.55 mmol) in MeOH (60 mL) was added a 2N aqueous NaOH solution (15 mL) and the resulting mixture was refluxed for 1.5 hours. Once at room temperature, the reaction was acidified to pH 4 with an aqueous 1N HCl solution. The resulting precipitate was collected by filtration, washed with H$_2$ and dried to give 700 mg (92%) of the acid as a grey solid, mp.154–155° C. $^1$H NMR (DMSO-d$_6$): δ 7.86 (d, 2H, J=9 Hz), 7.29–7.23 (m, 2H), 7.14–7.09 (m, 2H), 7.00 (d, 2H, J=9 Hz), 6.84 (d, 1H, J=3.6 Hz), 6.58 (d, 1H, J=3.6 Hz).

h) 5-[4-(4-Fluorophenoxy)phenyl]-pyrrole-2-carboxamide. To a solution of the acid (356 mg, 1.2 mmol) in DMF (10 mL) was added 1,1'-carbonyldiimidazole (CDI, 406 mg, 2.5 mmoL). The solution was heated at reflux for 1 hour, followed by the addition of solid NH$_4$OAc (1.2 g, 15.6 mmoL). After an additional 16 hours at reflux, the reaction mixture was allowed to cool to room temperature, diluted with EtOAc (100 mL), washed with brine, evaporated, and the residue was chromatographed (1/1 hexane/EtOAc) to give 180 mg (51%) of the amide as an off-white powder, mp 218–220° C. $^1$H NMR (DMSO-d$_6$): δ 11.59 (s, 1H), 7.82 (d, 2H, J=9 Hz), 7.52 (bs, 2H), 7.25 (t, 2H, J=9 Hz), 7.10–7.04 (m, 2H), 6,97 (d, 2H, J=9 Hz), 6.83 (dd, 1H, J=4 Hz, 1 Hz), 6.50 (dd, 1H, J=4 Hz, 1.2 Hz).

EXAMPLE 28

Methyl 5-[4-(4-Fluorophenoxy)phenyl]pyrrole-2-carboxylate

A mixture of 5-[4-(4-fluorophenoxy)phenyl]-pyrrole-2-carboxylic acid (300 mg, 1.0 mmol) and SOCl$_2$ (2 mL) was stirred at room temperature for 1 h and the resulting solution was evaporated to dryness. The residue was cooled in an ice-water bath, and a 2M solution of NH$_3$ in MeOH (5 mL) was added slowly. The reaction was stirred for 2 hours and then evaporated to dryness. The residue was taken up into CHCl$_3$, the CHCl$_3$ solution was evaporated, and the residue was chromatographed (7/3 hexane/EtOAc) to give 200 mg (64%) of the methyl ester as a light yellow solid, mp 144–145° C. $^1$H NMR (CDCl$_3$): δ 9.23 (bs, 1H), 7.54 (d, 2H, J=9 Hz), 7.11–6.96 (m, 5H), 6.51–6.49 (m, 1H), 3.90 (s, 3H).

EXAMPLE 29

2-[4-(4-Fluorophenoxy)phenyl]oxazole-4-carboxamide a) 4-(4-Fluorophenoxy)benzoic acid. A solution of 4-(4-fluorophenoxy)benzaldehyde (1.1 g, 5.1 mmol) in pyridine (25 mL) was treated with solid potassium permanganate (1.0 g, 6.3 mmol). The resulting mixture was stirred at room temperature for 16 hours. The mixture was then partitioned between an aqueous 2N HCl solution and a hexane/ethyl acetate solution. The aqueous layer was extracted two more times with hexane/ethyl acetate. The combined organic layers were filtered through a bed of Celite. The filtrate was washed with an aqueous 2N HCl solution, dried over sodium sulfate, filtered, and evaporated under reduced pressure to give 790 mg (67%) of the desired product as a white solid. $^1$H NMR (DMSO-d$_6$): 12.80 (bs, 1H), 7.94 (d, J=8.1 Hz, 2H), 7.30 (t, J=8.7 Hz, 2H), 7.21–7.17 (m, 2H), 7.01 (d, J=8.4 Hz, 2H).

b) N-[4-(4-Fluorophenoxy)benzoyl]-L-serine methyl ester. To an ice cold solution of 4-(4-fluorophenoy)benzoic acid (0.79 g, 3.4 mmol), L-serine methyl ester hydrochloride (0.59 g, 3.7 mmol), and a 1-hydroxybenzotriazole hydrate (0.57 g, 3.7 mmol) in DMF (20 mL) was added N-methylmorpholine (82 mL, 7.4 mmol), and 1-[3-(dimethylamino)propyl]-3-ethylcarbodiimide hydrochloride (0.72 g, 3.7 mmol). The resulting solution was allowed to warm to room temperature overnight and was then partitioned between water and ethyl acetate. The aqueous layer was extracted twice with ethyl acetate and the combined ethyl acetate layers were washed with water (3×), dried over sodium sulfate, filtered, and evaporated under reduced pressure to give the desired product as an oil. $^1$H NMR (DMSO-d$_6$): 8.51 (d, J=7.5 Hz, 1H), 7.92 (d, J=8.7 Hz, 2H), 7.28 (t, J=8.4 Hz, 2H), 7.18–7.13 (m, 2H), 7.04 (d, J=9.0 Hz, 2H), 5.06 (t, J=6.3 Hz, 1H), 4.53 (q, J=7.8 Hz, 1H), 3.79 (t, J=5.4 Hz, 2H), 3.71 (s, 3H).

c) Methyl 4,5-dihydro-2-[4-(4-fluorophenoxy)phenyl] oxazole-4-carboxylate. To a solution of N-[4-(4-fluorophenoxy)benzoyl]-L-serine methyl ester (assumed to be 37 mmol from the previous reaction) and triphenylphosphine (0.38 g, 6.8 mmol) in acetonitrile (40 mL) was added diisopropylethyl amine (1.2 ml, 6.8 mmol) and carbon tetrachloride (0.66 mL, 6.8 mmol). The resulting solution was stirred at room temperature for 48 hours when TLC analysis indicated incomplete reaction. Triphenylphosphine (1.9 g, 7.2 mmol), diisopropylethyl amine (1.2 mL. 6.8 mmol) and carbon tetrachloride (0.66 mL, 6.8 mmol) was added to the reaction. The solution was stirred at room temperature for 16 hours and concentrated to dryness. The resulting solid was purified by column chromatography affording 910 mg (89%) of the desired product. $^1$H NMR (DMSO-d$_6$): 7.88 (d, J=8.7 Hz, 2H), 7.29 (t, J=9.3 Hz, 2H), 7.20–7.17 (m, 2H), 7.03 (d, J=8.7 Hz, 2H), 4.95 (dd, J=8.1 Hz, 1H), 4.64–4.25 (m, 2H), 3.71 (s, 3H).

d) Methyl 2-[4-(4-fluorophenoxy)phenyl]oxazole-4-carboxylate. A mixture of methyl 4,5-dihydro-2-[4-(4-fluorophenoxy)phenyl]oxazole-4-carboxylate (0.91 g, 2.88 mmol), manganese dioxide (2.2 g, 85%, 21.5 mmol) and 4Å molecular sieves (1.2 g) in benzene (30 mL) was refluxed for 3 hours. An additional 1.2 g (11.7 mmol) of manganese dioxide was added and the reaction was heated at reflux for an additional 2 hours. After the mixture was cooled to room temperature, water was added to the mixture. The mixture was filtered through a bed of Celite. The filtrate was extracted twice with dichloromethane and the combined dichloromethane layers were dried over sodium sulfate, filtered, and evaporated under reduced pressure to give the product as a light yellow solid. $^1$H NMR (CDCl$_3$): 8.28 (s, 1H), 8.09 (d, J=8.7 Hz, 2H), 7.11–7.02 (m, 6H), 3.98 (s, 3H).

e) 2-[4-(4-Fluorophenoxy)phenyl]-oxazole-4-carboxamide. The crude methyl ester prepared above was dissolved in MeOH and an aqueous ammonium hydroxide solution (10 mL) was added. After stirring at room temperature for several hours, TLC analysis showed incomplete reaction. An additional 10 mL of an aqueous ammonium hydroxide solution was added, and the solution was stirred at room temperature for 16 hours. The solution was then partitioned between water and ethyl acetate. The aqueous layer was extracted 2 times with ethyl acetate. The combined ethyl acetate layers were dried over sodium sulfate, filtered, and evaporated under reduced pressure to give the crude product. Purification by column chromatography gave 227 mg (26%) of the title compound as a white solid, mp 164° C. $^1$H NMR (CDCl$_3$): 8.27 (s, 1H), 8.02 (d, J=9.0 Hz, 2H), 7.15–7.04 (m, 6H), 6.93 (bs, 1H), 5.61 (bs, 1H).

EXAMPLE 30

4-[4-(4-Fluorophenoxy)-3-fluorophenyl]-thiazole-2-carboxamide a) 2-Bromo-1-[4-(4-fluorophenoxy)-3-fluorophenyl]-ethanone. A solution of 1-[4-(4-fluorophenoxy)-3-fluorophenyl]-ethanone (2.68 g, 10.8 mmol, prepared as described for 1-[4-(4-fluorophenoxy)phenyl]-ethanone) in methanol containing an aqueous 48% HBr solution (4 drops) was treated with a solution of bromine (0.61 mL, 11.8 mmol) in methanol. After stirring at room temperature for several hours, the solution was evaporated in vacuo. The residue was partitioned between water and ethyl acetate. The ethyl acetate layer was dried over sodium sulfate, filtered and evaporated under reduced pressure to give 3.45 g (97%) of the crude bromide. $^1$H NMR (CDCl$_3$): 7.82 (dd, J=11.4, 2.4 Hz, 1H), 7.24 (d, J=8.7 Hz, 1H), 7.28–7.07 (m, 3H), 6.92 (t, J=8.4 Hz, 2H), 4.37 (s, 2H).

b) Ethyl 4-[4-(4-fluorophenoxy)-3-fluorophenyl]-thiazole-2-carboxylate. A solution containing 2-bromo-1-[4-(4-fluorophenoxy)-3-fluorophenyl]ethanone (1.30 g, 3.97 mmol) and ethyl thioxamate (0.60 g, 4.3 mmol) in ethanol was refluxed for 16 hours. The solution was then partitioned between water and ethyl acetate. The aqueous layer was extracted twice with ethyl acetate/hexane. The combined organic layers were dried over sodium sulfate, filtered, and evaporated under reduced pressure to give the crude product. This material was carried on to the next step without purification. $^1$H NMR (CDCl$_3$): 7.80 (d, J=11.7 Hz, 1H), 7.69 (s, 1H), 7.66 (d, J=7.2 Hz, 1H), 7.06–6.97 (m, 5H), 4.51 (q, J=6.9 Hz, 2H), 1.47 (t, J=6.9 Hz, 3H).

c) 4-[4-(4-Fluorophenoxy)-3-fluorophenyl]-thiazole-2-carboxamide. A solution of crude ethyl 4-[4-(4-fluorophenoxy)-3-fluorophenyl]-thiazole-2-carboxylate in methanol (40 mL) and an aqueous ammonium hydroxide solution (10 mL) was stirred at room temperature for several hours. The solution was evaporated under reduced pressure and the residue was partitioned between water and ethyl acetate. The aqueous layer was extracted once with ethyl acetate. The combined ethyl acetate layers were dried over sodium sulfate, filtered, evaporated under reduced pressure, and purified by column chromatography to give 765 mg (58%) of the title compound as a yellow solid, mp 183° C. $^1$H NMR (CDCl$_3$): 7.76 (dd, J=11.7, 2.1 Hz, 1H), 7.70 (s, 1H), 7.60 (d, J=8.7 Hz, 1H), 7.18 (bs, 1H), 7.08–7.00 (m, 5H), 5.66 (bs, 1H).

EXAMPLE 31

3-[4-(2,4-Difluorophenoxy)phenyl]-1H-pyrazole-1-carboxamitle as Anticonvulsant

The ability of 3-[4-(2,4-difluorophenoxy)phenyl]-1H-pyrazole-1-carboxamide to block maximal electroshock-induced seizures (MES) was determined as described earlier.

3-[4-(2,4-Difluorophenoxy)phenyl]-1H-pyrazole-1-carboxamide was administered p.o. to mice 30 minutes before the test procedure. The compound exhibited protection against MES with an ED$_{50}$ (the dose provided protection of 50% of animals) of 3.5 mg/kg.

The following compounds in Table 1 were tested in MES as described for 3-[4-(2,4-difluorophenoxy)phenyl]-1H-pyrazole-1-carboxamide:

TABLE 1

Anticonvulsant Evaluation after Oral Administration to Mice

| Compound name | MES p.o. ED$_{50}$/ mg/kg |
|---|---|
| 4-[4-(4-fluorophenoxy)phenyl]-1H-imidazole | 4.2 |
| 4-[4-(4-fluorophenoxy)-3-fluorophenyl]-1H-imidazole | 3.2 |
| 4-[4-(2-fluoro-4-chlorophenoxy)phenyl]-1H-imidazole, hydrochloride | 10 |
| 4-(4-(4-trifluoromethylphenoxy)phenyl]-1H-imidazole, hydrochloride | 7.7 |
| 4-[4-(2,4-difluorophenoxy)phenyl]-2-methyl-1H-imidazole | 7.5 |
| Methyl 5-[4-(4-fluorohenoxy)phenyl]pyrrole-2-carboxylate | 6.0 |
| 5-[4-(4-fluorohenoxy)phenyl]-pyrrole-2-carboxamide | 10 |
| 3-[4-(4-fluorophenoxy)phenyl]-1H-pyrazole-1-carboxamide | 7.0 |
| 3-[4-(4-chloro-2-fluorophenoxy)phenyl]-1H-pyrazole-1-carboxamide | 3.1 |
| 3-[4-(4-nitrophenoxy)phenyl]-1H-pyrazole-1-carboxamide | 2.0 |
| 5-[4-(4-fluorophenoxy)phenyl]-1H-pyrazole | 8.0 |
| 3-[3-fluoro-4-(4-fluorophenoxy)phenyl]-1H-pyrazole-1-carboxamide | 4.5 |
| 2-{5-[4-(4-fluorophenoxy)phenyl]-pyrazol-1-yl}-acetamide | 2.6 |
| 2-{3-[4-(4-fluorophenoxy)phenyl]-pyrazol-1-yl}-pyrimidine | 4.7 |
| 3-[4-(4-trifluoromethylphenoxy)phenyl]-1H-pyrazole-1-carboxamide | 3.9 |
| 2-(N-methylacetamido)-3-[4-(4-fluorophenoxy)phenyl]-2H-pyrazole | 2.9 |
| 3-[4-(4-fluorophenoxy)phenyl]-1H-pyrazole-1-carboxylic acid dimethylamide | 8.6 |
| 1-[2-(methanesulfonylamino)ethyl]-5-[4-(4-fluorophenoxy)phenyl]-1H-pyrazole | 7.5 |
| 1-morpholin-4-yl-2-{5-[4-(4-fluoro-phenoxy)phenyl]pyrazol-1-yl}-ethanone | 4.4 |
| 2-{5-[4-(4-fluorophenoxy)phenyl]-pyrazol-1-yl}-1-(4-methyl)-piperazin-1-yl-ethanone | 10 |

EXAMPLE 32

Activity of 3-[4-(4-Fluorophenoxy)phenyl]-1H-pyrazole-1-carboxantide as Sodium Channel Blocker 3-[4-(4-Fluorophenoxy)phenyl]-1H-pyrazole-1-carboxamide was tested in the electrophysiological and binding assays described above and produced dose-dependent inhibition of voltage-gated sodium currents recorded in HEK-293 cells stably expressing hSkM1 sodium channels. The blocking effect of this compound on Na$^+$ currents was highly sensitive to the holding voltage, indicating that 3-[4-(4-fluorophenoxy)phenyl]-1H-pyrazole-1-carboxamide binds to voltage-sensitive Na$^+$ channels in their inactivated states and has weak potency towards Na$^+$ channels in their resting states (Ragsdale et al., *Mol. Pharmacol.* 40:756–765 (1991); Kuo and Bean, *Mol. Pharmacol.* 46:716–725 (1994)). The apparent antagonist dissociation constant (K$_d$) of this compound for inactivated sodium channels is ~8 nM.

The K$_i$ (the concentration of a compound that produces half maximal inhibition) value for 3-[4-(4-fluorophenoxy)phenyl]-1H-pyrazole-1-carboxamide and other tested compounds are presented in Table 2.

TABLE 2

Evaluation of the Tested Compounds as Sodium Channel Blockers after an Electrophysiological in vitro Assay

| Compound name | HSkM1 $K_i/\mu M$ |
|---|---|
| 3-[4-(4-fluorophenoxy)phenyl]-1H-pyrazole-1-carboxamide | 0.008 |
| 3-(4-phenoxyphenyl)-1H-pyrazole-1-carboxamide | 0.015 |
| 3-[4-(2,4-difluorophenoxy)phenyl]-1H-pyrazole-1-carboxamide | 0.010 |
| 3-[4-(4-chloro-2-fluorophenoxy)phenyl]-1H-pyrazole-1-carboxamide | 0.003 |
| 5-methylthio-3-(4-phenoxyphenyl)-1H-pyrazole-1-carboxamide | 0.08 |
| 3-[4-(nitrophenoxy)phenyl]-1H-pyrazole-1-carboxamide | 0.011 |
| 1-{3-[4-(4-nitrophenoxy)phenyl]-pyrazol-1-yl}ethanone | 0.009 |
| 5-[4-(4-nitrophenoxy)phenyl]-1H-pyrazole | 0.11 |
| 4-[4-(4-fluorophenoxy)-3-fluorophenyl]thiazole-2-carboxamide | 0.02 |

EXAMPLE 33

Activity of 4-[4-(4-Fluorophenoxy)-3-fluorophenyl]-1H-imidazole, Hydrochloride Salt as Sodium Channel Blocker 4-[4-(4-Fluorophenoxy)-3-fluorophenyl]-1H-imidazole, hydrochloride salt was tested in the electrophysiological and binding assays described above and produced dose-dependent inhibition of voltage-gated sodium currents recorded in HEK-293 cells stably expressing the rBIIA isoform of $Na^+$ channels. The blocking effect of this compound on $Na^+$ currents was highly sensitive to the holding voltage, indicating that 4-[4-(4-fluorophenoxy)-3-fluorophenyl]-1H-imidazole hydrochloride binds to voltage-sensitive $Na^-$ channels in their inactivated states and has weak potency towards $Na^+$ channels in their resting states (Ragsdale et al., *Mol. Pharmacol.* 40:756–765 (1991); Kuo and Bean, *Mol. Pharmacol.* 46:716–725 (1994)). The apparent antagonist dissociation constant ($K_d$) of this compound for inactivated sodium channels is 250 nM.

The $K_i$ (the concentration of a compound that produces half maximal inhibition) value for 4-[4-(4-fluorophenoxy)-3-fluorophenyl]-1H-imidazole hydrochloride and other tested compounds are presented in Table 3.

TABLE 3

Evaluation of the Tested Compounds as Sodium Channel Blockers after an Electrophysiological in vitro Assay

| Compound name | RBIIA $K_i/\mu M$ |
|---|---|
| 4-[4-(4-fluorophenoxy)-3-fluorophenyl]-1H-imidazole, hydrochloride | 0.25 |
| 2-{5-[4-(4-fluorophenoxy)phenyl]-pyrazol-1-yl}acetamide | 1.56 |
| 2-{3-(4-(4-fluorophenoxy)phenyl]-pyrazol-1-yl}pyrimidine | 0.42 |
| 4-[4-(2,4-difluorophenoxy)phenyl]-1H-imidazole | 1.03 |
| 4-[4-(2-fluoro-4-chlorophenoxy)phenyl]-1H-imidazole, hydrochloride | 0.12 |
| 2-[4-(4-fluorophenoxy)phenyl]-]1H-imidazole, hydrochloride | 1.1 |
| 2-[4-(4-fluorophenoxy)phenyl]oxazole-4-carboxamide | 1.31 |

Having now fully described this invention, it will be understood by those of ordinary skill in the art that the same can be performed within a wide and equivalent range of conditions, formulations and other parameters without affecting the scope of the invention or any embodiment thereof. All patents and publications cited herein are fully incorporated by reference herein in their entirety.

What is claimed is:

1. A compound having the Formula I:

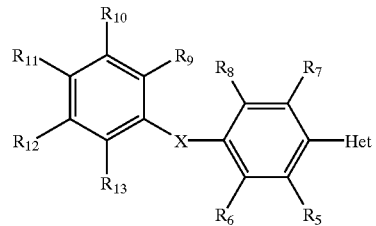

or a pharmaceutically acceptable salt, prodrug or solvate thereof, wherein:

Het is a heteroaryl selected from the group consisting of

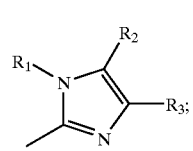

(iii)

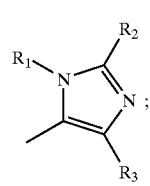

(iv)

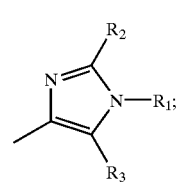

(v)

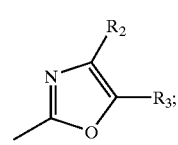

(vii)

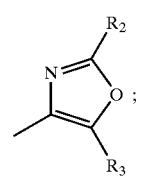

(viii)

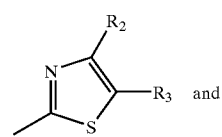

(ix)

and

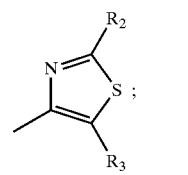

(x)

$R_1$ is selected from the group consisting of hydrogen, alkyl, cycloalkyl, aryl, aralkyl, heteroaryl, $C(O)R_{14}$, $CH_2C(O)R_{14}$, $S(O)R_{14}$, and $SO_2R_{14}$ all of which may be optionally substituted;

$R_2$ and $R_3$ are independently selected from the group consisting of hydrogen, cycloalkyl, alkenyl, alkynyl, haloalkyl, aminoalkyl, hydroxyalkyl, alkoxyalkyl, alkylthio, alkylsulfinyl, alkylsulfonyl, carboxyalkyl, cyano, alkylamino, aminocarbonyl, alkylaminocarbonyl, arylaminocarbonyl, aralkylaminocarbonyl, arylcarbonylamino, aralkylcarbonylamino, alkylcarbonyl, heterocyclocarbonyl, aminosulfonyl, alkylaminosulfonyl, alkylsulfonyl, and heterocyclosulfonyl, or the R groups on adjacent carbon atoms can be taken together with the carbon atoms to which they are attached to form a heterocycle;

$R_5$, $R_6$, $R_7$, $R_8$, $R_9$, $R_{10}$, $R_{11}$, $R_{12}$, and $R_{13}$ are independently selected from the group consisting of hydrogen, halo, haloalkyl, aryl, cycloalkyl, saturated or partially unsaturated heterocycle, heteroaryl, alkyl, alkenyl, alkynyl, arylalkyl, arylalkenyl, arylalkynyl, heteroarylalkyl, heteroarylalkenyl, heteroarylalkynyl, cycloalkylalkyl, heterocycloalkyl, hydroxyalkyl, aminoalkyl, carboxyalkyl, alkoxyalkyl, nitro, amino, ureido, cyano, acylamino, amide, thiol, acyloxy, azido, carboxy, carbonylamido and alkylthiol; or $R_9$ and $R_{10}$ or $R_{10}$ and $R_{11}$ are taken together with the carbon atoms to which they are attached to form a carbocycle or a heterocycle;

$R_{14}$ is selected from the group consisting of amino, alkyl, alkenyl, alkynyl, $OR_{16}$, alkylamino, dialkylamino, alkenylamino, cycloalkyl, aralkyl, aryl, heteroaryl, arylalkenyl, arylalkynyl, arylalkylamino, dialkylaminoalkenyl, heterocycle, heterocycloalkylamino, and cycloalkylalkylamino, all of which can be optionally substituted; wherein $R_{16}$ is selected from the group consisting of hydrogen, optionally substituted alkyl, and an alkalimetal; and X is one of O, S, $NR_{15}$, $CH_2$, $NR_{15}C(O)$, or $C(O)NR_{15}$, wherein $R_{15}$ is hydrogen, alkyl or cycloalkyl, with the provisos that:

1) when Het is (iii),
   a) $R_1$ is H, X is O or $CH_2$ and $R_2$ and $R_3$ together form —CH=CH—CH=CH—, $R_5$–$R_{13}$ are not all H;
   b) $R_1$ is Et and $R_2$ and $R_3$ together form —CH=CH—CH=CH—, X is not —NEt; or
   c) $R_1$ is H and X is O, $R_5$–$R_{13}$ are not all H; or
2) when Het is (iv) and $R_1$ is H or alkyl, $R_2$–$R_{13}$ are not all H.

2. The compound of claim 1, wherein the two R groups attached to adjacent carbon atoms taken together form —OCH$_2$O—, —OCF$_2$O—, —OCH$_2$CH$_2$O—, —CH$_2$N(R$_{15}$)CH$_2$, —CH$_2$CH$_2$N(R$_{15}$)CH$_2$— or —CH$_2$N(R$_{15}$)CH$_2$CH$_2$—, wherein $R_{15}$ is hydrogen, alkyl or cycloalkyl.

3. The compound of claim 1, wherein $R_9$ and $R_{10}$ or $R_{10}$ and $R_{11}$ taken together are —OCH$_2$O—, —OCF$_2$O—, —(CH$_2$)$_3$—, —(CH$_2$)$_4$—, —OCH$_2$CH$_2$O—, —CH$_2$N(R$_{15}$)CH$_2$—, —CH$_2$CH$_2$N(R$_{15}$)CH$_2$—, —CH$_2$N(R$_{15}$)CH$_2$CH$_2$— and —CH=CH—CH=CH—, wherein $R_{15}$ is hydrogen, alkyl or cycloalkyl.

4. The compound of claim 1, wherein Het is selected from the group consisting of (iv) and (v).

5. The compound of claim 1, wherein $R_1$ is selected from the group consisting of an alkyl optionally substituted by halogen, hydroxy, carbamoyloxy, $C_{1-6}$ acyl, $C_{1-6}$ alkylsulfonylamino, aryl, or aminocarbonyl; heteroaryl; $C(O)R_{14}$; $CH_2C(O)R_{14}$; and $SO_2R_{14}$; wherein $R_{14}$ is selected from the group consisting of $C_{1-6}$ alkyl, $C_{2-6}$ alkenyl, $OR_{16}$, amino, $C_{1-6}$ alkylamino, di($C_{1-6}$)alkylamino, $C_{2-6}$ alkenylamino, di($C_{1-6}$)alkylaminoalkenyl, heterocycle, and heterocyclo($C_{1-6}$)alkylamino, all of which can be optionally substituted, and wherein $R_{14}$ and $R_{16}$ are as defined in claim 1.

6. The compound of claim 1, wherein $R_{14}$ is selected from the group consisting of $C_{1-6}$ alkyl, $C_{2-6}$ alkenyl, $OR_{1-6}$, amino, $C_{1-6}$ alkylamino, di($C_{1-6}$)alkylamino, $C_{2-6}$ alkenylamino, di($C_{1-6}$)alkylamino($C_{2-6}$)alkenyl, heterocycle, and heterocyclo($C_{1-6}$)alkylamino, all of which can be optionally substituted, wherein $R_{16}$ is as defined in claim 1.

7. The compound of claim 5, wherein $R_1$ is $C(O)R_{14}$ or $SO_2R_{14}$, wherein $R_{14}$ is as defined in claim 1 and X is O or S.

8. The compound of claim 7, wherein $R_{14}$ is amino or $C_{1-6}$ alkyl.

9. The compound of claim 5, wherein $R_1$ is optionally substituted heteroaryl, optionally substituted $C_{1-6}$ alkyl, or $CH_2C(O)R_{14}$, wherein $R_{14}$ is an optionally substituted heterocycle, optionally substituted $C_{1-6}$ alkyl, $C_{1-6}$ alkylamino, $C_{1-6}$ dialkylamino, or $OR_{16}$, wherein $R_{16}$ is $C_{1-6}$ alkyl.

10. The compound of claim 9, wherein $R_{14}$ is an optionally substituted heterocycle selected from the group consisting of optionally substituted N-morpholinyl, N-pyrrolidinyl and N-piperazinyl.

11. The compound of claim 1, wherein Het is (iii), (iv) or (v), $R_1$ is H or alkyl and $R_2$ and $R_3$ are both hydrogen.

12. The compound of claim 1, wherein Het is (vii), (viii), (ix) or (x), $R_2$ is hydrogen or aminocarbonyl, and $R_3$ is hydrogen.

13. The compound of claim 1, wherein $R_2$ and $R_3$ are independently selected from the group consisting of hydrogen, $C_2$–$C_6$ alkenyl, $C_2$–$C_6$ alkynyl, amino($C_1$–$C_6$)alkyl, $C_1$–$C_6$ alkylthio, cyano, $C_1$–$C_6$ alkylsulfinyl, hydroxy($C_1$–$C_6$)alkyl, $C_1$–$C_6$ alkoxy, aminocarbonyl, $C_1$–$C_6$ alkylaminocarbonyl, $C_6$–$C_{10}$ arylaminocarbonyl, $C_6$–$C_{10}$aryl($C_1$–$C_6$)alkylaminocarbonyl, $C_6$–$C_{10}$ arylcarbonylamino, $C_6$–$C_{10}$ aryl($C_1$–$C_6$)alkylcarbonylamino, $C_1$–$C_6$ alkylcarbonyl heterocyclocarbonyl, aminosulfonyl, $C_1$–$C_6$ alkylaminosulfonyl, $C_1$–$C_6$ alkylsulfonyl and heterocyclosulfonyl.

14. The compound of claim 13, wherein $R_2$ and $R_3$ are independently selected from the group consisting of hydrogen, $C_1$–$C_6$ alkoxy, amino($C_1$–$C_6$)alkyl, $C_1$–$C_6$ alkylthio and aminocarbonyl.

15. The compound of claim 1, wherein $R_5$–$R_{13}$ are independently selected from the group consisting of hydrogen, halo, $C_1$–$C_6$ haloalkyl, $C_6$–$C_{10}$ aryl, $C_4$–$C_7$ cycloalkyl, $C_1$–$C_6$ alkyl, $C_2$–$C_6$ alkenyl, $C_2$–$C_6$ alkynyl, $C_6$–$C_{10}$ aryl($C_1$–$C_6$)alkyl, $C_6$–$C_{10}$ aryl($C_2$–$C_6$)alkenyl, $C_6$–$C_{10}$ aryl($C_2$–$C_6$)alkynyl, $C_1$–$C_6$ hydroxyalkyl, nitro, amino, ureido, cyano, $C_1$–$C_6$ acylamido, thiol, $C_1$–$C_6$ acyloxy, azido, and carboxy.

16. The compound of claim 15, wherein $R_5$–$R_8$ are all hydrogen.

17. The compound of claim 1, wherein X is O or S.

18. The compound of claim 17, wherein X is O.

19. A compound having Formula III:

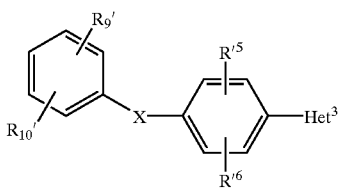

or a pharmaceutically acceptable salt, prodrug or solvate thereof, wherein

Het$^3$ is selected from the group consisting of

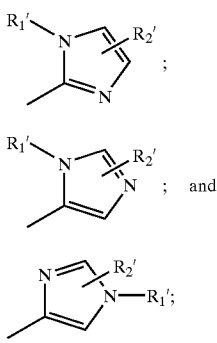

R'$_1$ is selected from the group consisting of hydrogen, optionally substituted alkyl, optionally substituted heteroaryl, C(O)R$_{14}$, CH$_2$C(O)R$_{14}$, S(O)R$_{14}$, and SO$_2$R$_{14}$;

R'$_2$ is attached to a carbon atom that is not the linking atom attached to the aryl group and is selected from the group consisting of hydrogen, alkyl, alkenyl, alkynyl, cyano, haloalkyl, aminoalkyl, hydroxyalkyl, alkoxyalkyl, alkylthio, alkylsulfinyl, alkylsulfonyl, carboxyalkyl, alkylamino, dialkylamino, aminocarbonyl, alkylaminocarbonyl, arylaminocarbonyl, aralkylaminocarbonyl, alkylcarbonylamino, arylcarbonylamino, aralkylcarbonylamino, alkylcarbonyl, heterocyclocarbonyl, aminosulfonyl, alkylaminosulfonyl, alkylsulfonyl, and heterocyclosulfonyl;

R'$_5$, R'$_6$, R'$_9$, and R'$_{10}$ are independently selected from the group consisting of hydrogen, halo, haloalkyl, alkyl, alkenyl, alkynyl, hydroxyalkyl, aminoalkyl, carboxyalkyl, alkoxyalkyl, nitro, amino, ureido, cyano, acylamino, amide, thiol, acyloxy, azido, alkoxy, carboxy, carbonylamido and alkylthiol;

R$_{14}$ is selected from the group consisting of amino, alkyl, alkenyl, alkynyl, OR$_{16}$, alkylamino, dialkylamino, alkenylamino, dialkylaminoalkenyl, cycloalkyl, aralkyl, aryl, heteroaryl, arylalkenyl, arylalkenyl, heterocycle, heterocycloalkyl, and cycloalkylalkylamino, all of which can be optionally substituted; wherein R$_{16}$ is selected from the group consisting of hydrogen, optionally substituted alkyl, and an alkalimetal; and X is one of O, S, NR$_{15}$, CH$_2$, NR$_{15}$C(O), or C(O)NR$_{15}$ where R$_{15}$ is defined as above, with the following provisos that:

1) when Het$^3$ is (iii)$^3$, R'$_1$ is H and X is O, R'$_5$, R'$_6$, R'$_9$ or R'$_{10}$ are not all H; or 2) when Het$^3$ is (iv)$^3$ and R'$_1$ is H or alkyl, R'$_5$, R'$_6$, R'$_9$ or R'$_{10}$ are not all H.

20. The compound of claim 19, wherein X is O or S.
21. The compound of claim 19, wherein Het$^3$ is (iv)$^3$.
22. The compound of claim 19, wherein Het$^3$ is (v)$^3$.
23. The compound of claim 19, wherein R'$_2$ is selected from the group consisting of hydrogen, C$_1$–C$_6$ alkyl, halo (C$_1$–C$_6$)alkyl, amino(C$_1$–C$_6$)alkyl, hydroxy(C$_1$–C$_6$)alkyl, alkoxy(C$_1$–C$_6$)alkyl, C$_1$–C$_6$ alkylthio, C$_1$–C$_6$ alkylsulfinyl, carboxy(C$_1$–C$_6$)alkyl, C$_1$–C$_6$ alkylamino, aminocarbonyl, C$_1$–C$_6$ alkylaminocarbonyl, C$_1$–C$_6$ alkylcarbonyl, heterocyclocarbonyl, aminosulfonyl, C$_1$–C$_6$ alkylaminosulfonyl, C$_1$–C$_6$ alkylsulfonyl and heterocyclosulfonyl.

24. The compound of claim 23, wherein R'$_2$ is hydrogen or aminocarbonyl.

25. The compound of claim 19, wherein R'$_5$, R'$_6$, R'$_9$, and R'$_{10}$ are independently selected from the group consisting of hydrogen, halo, halo(C$_1$–C$_6$)alkyl, C$_1$–C$_6$ alkyl, hydroxy (C$_1$–C$_6$)alkyl, amino(C$_1$–C$_6$)alkyl, carboxy(C$_1$–C$_6$)alkyl, alkoxy(C$_1$–C$_6$)alkyl, nitro, amino, C$_1$–C$_6$ acylamino, amide, thiol, C$_1$–C$_6$ acyloxy, C$_1$–C$_6$ alkoxy, carboxy, carbonylamido and C$_1$–C$_6$ alkylthiol.

26. The compound of claim 19, wherein Het$^3$ is (iii)$^3$.

27. A compound having Formula III:

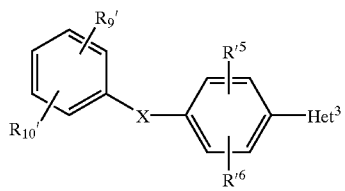

or a pharmaceutically acceptable salt, prodrug or solvate thereof, wherein

Het$^3$ is selected from the group consisting of

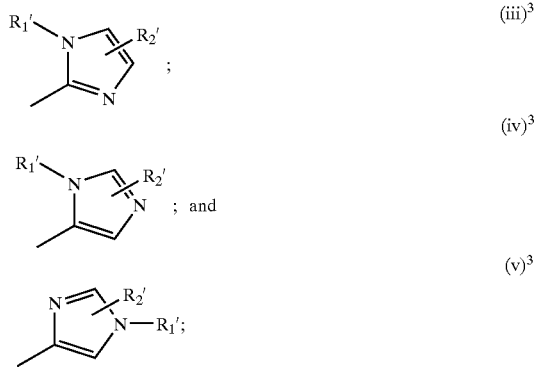

R'$_1$ is selected from the group consisting of hydrogen, optionally substituted alkyl, optionally substituted heteroaryl, C(O)R$_{14}$, CH$_2$C(O)R$_{14}$, S(O)R$_{14}$, and SO$_2$R$_{14}$;

R'$_2$ is attached to a carbon atom that is not the linking atom attached to the aryl group and is selected from the group consisting of hydrogen, alkyl, alkenyl, alkynyl, cyano, haloalkyl, aminoalkyl, hydroxyalkyl, alkoxyalkyl, alkylthio, alkylsulfinyl, alkylsulfonyl, carboxyalkyl, alkylamino, dialkylamino, aminocarbonyl, alkylaminocarbonyl, arylaminocarbonyl, aralkylaminocarbonyl, alkylcarbonylamino, arylcarbonylamino, aralkylcarbonylamino, alkylcarbonyl, heterocyclocarbonyl, aminosulfonyl, alkylaminosulfonyl, alkylsulfonyl, and heterocyclosulfonyl;

$R'_5$, $R'_6$, and $R'_{10}$ are independently selected from the group consisting of hydrogen, halo, haloalkyl, alkyl, alkenyl, alkynyl, hydroxyalkyl, aminoalkyl, carboxyalkyl, alkoxyalkyl, nitro, amino, ureido, cyano, acylamino, amide, thiol, acyloxy, azido, alkoxy, carboxy, carbonylamido and alkylthiol;

$R'_9$ is selected from the group consisting of halo, haloalkyl, alkenyl, alkynyl, hydroxyalkyl, aminoalkyl, carboxyalkyl, alkoxyalkyl, nitro, amino, ureido, cyano, acylamino, amide, thiol, acyloxy, azido, alkoxy, carboxy, carbonylamido and alkylthiol;

$R_{14}$ is selected from the group consisting of amino, alkyl, alkenyl, alkynyl, $OR_{16}$, alkylamino, dialkylamino, alkenylamino, dialkylaminoalkenyl, cycloalkyl, aralkyl, aryl, heteroaryl, arylalkenyl, arylalkenyl, heterocycle, heterocycloalkyl, and cycloalkylalkylamino, all of which can be optionally substituted; wherein $R_{16}$ is selected from the group consisting of hydrogen, optionally substituted alkyl, and an alkalimetal; and X is one of O, S, $NR_{15}$, $CH_2$, $NR_{15}C(O)$, or $C(O)NR_{15}$ where $R_{15}$ is hydrogen, alkyl or cycloalkyl.

28. The compound of claim 1, having Formula IV:

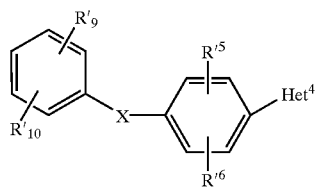

or a pharmaceutically acceptable salt, prodrug or solvate thereof, wherein

Het$^4$ is selected from the group consisting of

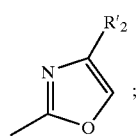 (vii)$^4$

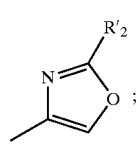 (viii)$^4$

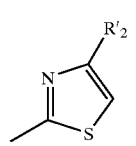 (ix)$^4$ and

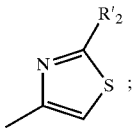 (x)$^4$ $R'_2$ is selected from the group consisting of hydrogen, alkenyl, alkynyl, cyano, haloalkyl, aminoalkyl, hydroxyalkyl, alkoxyalkyl, alkylthio, alkylsulfinyl, alkylsulfonyl, carboxyalkyl, alkylamino, dialkylamino, aminocarbonyl, alkylaminocarbonyl, arylaminocarbonyl, aralkylaminocarbonyl, arylcarbonylamino, aralkylcarbonylamino, alkylcarbonyl, heterocyclocarbonyl, aminosulfonyl, alkylaminosulfonyl, alkylsulfonyl, and heterocyclosulfonyl;

$R'_5$, $R'_6$, $R'_9$, and $R'_{10}$ are independently selected from the group consisting of hydrogen, halo, haloalkyl, alkyl, alkenyl, alkynyl, hydroxyalkyl, aminoalkyl, carboxyalkyl, alkoxyalkyl, nitro, amino, ureido, cyano, acylamino, amide, thiol, acyloxy, azido, carboxy, carbonylamido and alkylthiol; and X is one of O, S, $NR_{15}$, $CH_2$, $NR_{15}C(O)$, or $C(O)NR_{15}$ where $R_{15}$ is defined as above.

29. The compound of claim 28, wherein Het$^4$ is (vii)$^4$ or (x)$^4$.

30. The compound of claim 1, wherein said compound is:
4-[4-(4-fluorophenoxy)phenyl]-1H-imidazole;
4-[4-(4-fluorophenoxy)-3-fluorophenyl]-1H-imidazole;
4-[4-(2,4-difluorophenoxy)phenyl]-1H-imidazole;
4-[4-(2-fluoro-4-chlorophenoxy)phenyl]-1H-imidazole;
4-[4-(4-trifluoromethylphenoxy)phenyl]-1H-imidazole;
4-[4-(2,4-difluorophenoxy)phenyl]-2-methyl-1H-imidazole;
4-[4-(2,4-difluorophenoxy)phenyl]-1-methyl-1H-imidazole-2-carboxamide;
2-[4-(4-fluorophenoxy)phenyl]-1H-imidazole;
2-[4-(4-fluorophenoxy)phenyl]-1H-benzimidazole;
2-[4-(4-fluorophenoxy)phenyl]-1H-imidazole-4-carboxamide;
2-[4-(4-fluorophenoxy)phenyl]-1H-imidazole-4-carbonitrile;
2-[4-(4-fluorophenoxy)phenyl]oxazole-4-carboxamide; or
4-[4-(4-fluorophenoxy)-3-fluorophenyl]thiazole-2-carboxamide
or a pharmaceutically acceptable salt thereof.

31. A compound having the formula:

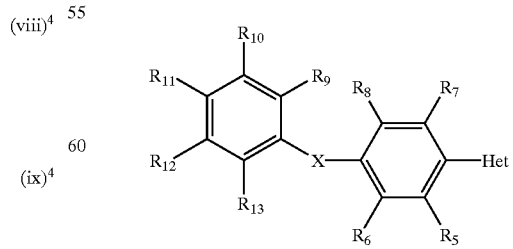 I or a pharmaceutically acceptable salt, prodrug or solvate thereof, wherein:

Het is a heteroaryl selected from the group consisting of

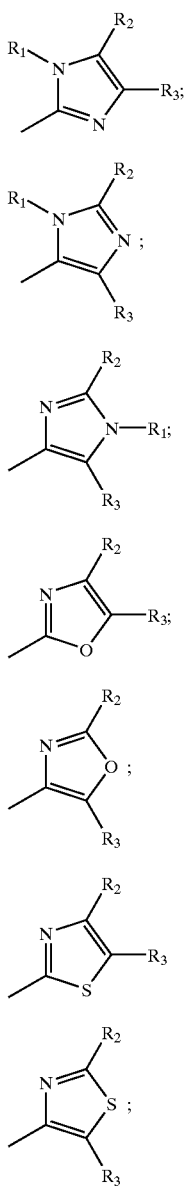

R₁ is selected from the group consisting of hydrogen, alkyl, cycloalkyl, aryl, aralkyl, heteroaryl, C(O)R₁₄, CH₂C(O)R₁₄, S(O)R₁₄, and SO₂R₁₄ all of which may be optionally substituted;

R₂ and R₃ are independently selected from the group consisting of hydrogen, alkyl, cycloalkyl, alkenyl, alkynyl, haloalkyl, aryl, aminoalkyl, hydroxyalkyl, alkoxyalkyl, alkylthio, alkylsulfinyl, alkylsulfonyl, carboxyalkyl, cyano, amino, alkylamino, aminocarbonyl, alkylaminocarbonyl, arylaminocarbonyl, aralkylaminocarbonyl, alkylcarbonylamino, arylcarbonylamino, aralkylcarbonylamino, alkylcarbonyl, heterocyclocarbonyl, aminosulfonyl, alkylaminosulfonyl, alkylsulfonyl, and heterocyclosulfonyl, or the R groups in adjacent carbon atoms can be taken together with the carbon atoms to which they are attached to form a carbocycle or a heterocycle;

R₅, R₆, R₇, R₈, R₉, R₁₀, R₁₁, R₁₂, and R₁₃ are independently selected from the group consisting of hydrogen, halo, haloalkyl, aryl, cycloalkyl, saturated or partially unsaturated heterocycle, heteroaryl, alkyl, alkenyl, alkynyl, arylalkyl, arylalkenyl, arylalkynyl, heteroarylalkyl, heteroarylalkenyl, heteroarylalkynyl, cycloalkylalkyl, heterocycloalkyl, hydroxyalkyl, aminoalkyl, carboxyalkyl, alkoxyalkyl, nitro, amino, ureido, cyano, acylamino, amide, hydroxy, thiol, acyloxy, azido, alkoxy, carboxy, carbonylamido and alkylthiol; or R₉ and R₁₀ or R₁₀ and R₁₁ are taken together with the carbon atoms to which they are attached to form a carbocycle or a heterocycle;

R₁₄ is selected from the group consisting of amino, alkyl, alkenyl, alkynyl, OR₁₆, alkylamino, dialkylamino, alkenylamino, cycloalkyl, aralkyl, aryl, heteroaryl, arylalkenyl, arylalkynyl, arylalkylamino, dialkylaminoalkenyl, heterocycle, heterocycloalkylamino, and cycloalkylalkylamino, all of which can be optionally substituted; wherein R₁₆ is selected from the group consisting of hydrogen, optionally substituted alkyl, and an alkalimetal; and X is one of O, S, NR₁₅, CH₂, NR₁₅C(O), or C(O)NR₁₅, wherein R₁₅ is hydrogen, alkyl or cycloalkyl,
    wherein said compound is ³H or ¹⁴C radiolabeled.

32. A pharmaceutical composition, comprising the compound of claim 1 and a pharmaceutically acceptable carrier or diluent.

33. A method of treating a disorder responsive to the blockade of sodium channels in a mammal suffering therefrom, comprising administering to a mammal in need of such treatment an effective amount of a compound of formula:

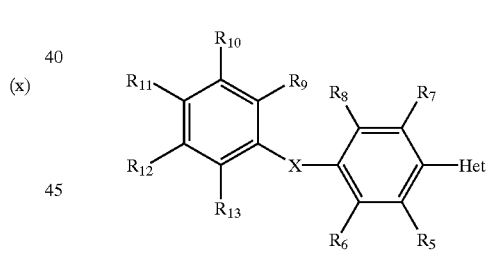

I or a pharmaceutically acceptable salt, prodrug or solvate thereof, wherein:

Het is a heteroaryl selected from the group consisting of

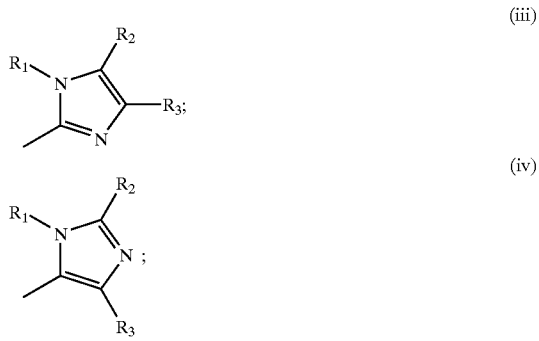

-continued

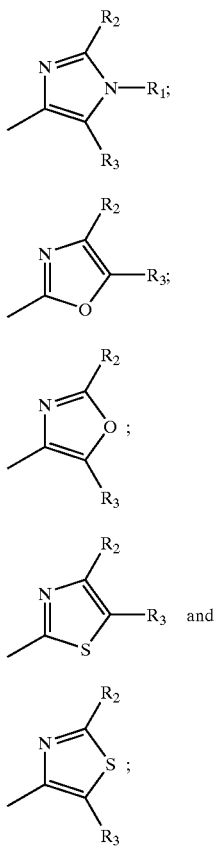

(v)

(vii)

(viii)

(ix)

(x)

R₁ selected from the group consisting of hydrogen, alkyl, cycloalkyl, aryl, aralkyl, heteroaryl, C(O)R₁₄, CH₂C(O)R₁₄, and SO₂R₁₄ all of which may by optionally substituted;

R₂ and R₃ are independently selected from the group consisting of hydrogen, alkyl, cycloalkyl, alkenyl, alkynyl, haloalkyl, aryl, aminoalkyl, hydroxyalkyl, alkoxyalkyl, alkylthio, alkylsulfinyl, alkylsulfonyl, carboxyalkyl, cyano, amino, alkylamino, aminocarbonyl, alkylaminocarbonyl, arylaminocarbonyl, aralkylaminocarbonyl, alkylcarbonylamino, arylcarbonylamino, aralkylcarbonylamino, alkylcarbonyl, heterocyclocarbonyl, aminosulfonyl, alkylaminosulfonyl, alkylsulfonyl, and heterocyclosufonyl, or the R groups in adjacent carbon atoms can be taken together with the carbon atoms to which they are attached to form a carbocycle or a heterocycle;

R₅, R₆, R₇, R₈, R₉, R₁₀, R₁₁, R₁₂, and R₁₃ are independently selected from the group consisting of hydrogen, halo, haloalkyl, aryl, cycloalkyl, saturated or partially unsaturated heterocycle, heteroaryl, alkyl, alkenyl, alkynyl, arylalkyl, arylalkenyl, arylalkynyl, heteroarylalkyl, heteroarylakenyl, heteroarylalkynyl, cycloalkylalkyl, heterocycloalkyl, hydroxyalkyl, aminoalkyl, carboxyalkyl, alkoxyalkyl, nitro, amino, ureido, cyano, acylamino, amide, hydroxy, thiol, acyloxy, azido, alkoxy, carboxy, carbonylamido and alkythiol; or R₉ and R₁₀ or R₁₀ and R₁₁ are taken together with the carbon atoms to which they are attached to form a carbocycle or a heterocycle;

R₁₄ is selected from the group consisting of amino, alkyl, alkenyl, alkynyl, OR₁₆, alkylamino, dialkylamino, alkenylamino, cycloalkyl, aralkyl, aryl, heteroaryl, arylalkenyl, arylalkynyl, arylalkylamino, dialkylaminoalkenyl, heterocycle, heterocycloalkylamino, and cycloalkylamino, all of which can be optionally substituted; wherein R₁₆ is selected from the group consisting of hydrogen, optionally substituted alkyl, and an alkalimetal; and X is one of O, S, NR₁₅, CH₂, NR₁₅C(O), or C(O)NR₁₅, wherein R₁₅ is hydrogen, alkyl or cycloalkyl.

34. The method of claim 33, wherein:

R₂ and R₃ are independently selected from the group consisting of hydrogen, cycloalkyl, alkenyl, alkynyl, haloalkyl, aminoalkyl, hydroxyalkyl, alkoxyalkyl, alkylthio, alkylsulfinyl, alkylsulfonyl, carboxyalkyl, cyano, alkylamino, aminocarbonyl, alkylaminocarbonyl, arylaminocarbonyl, aralkylaminocarbonyl, arylcarbonylamino, aralkylcarbonylamino, alkylcarbonyl, heterocyclcarbonyl, aminosulfonyl, alkylaminosulfonyl, alkylsulfonyl, and heterocyclosulfonyl, or the R groups on adjuvent carbon atoms can be taken together with carbon atoms to which they are attached to form a heterocycle; and R₅, R₆, R₇, R₈, R₉, R₁₀, R₁₁, R₁₂, and R₁₃ are independently selected from the group consisting of hydrogen, halo, haloalkyl, aryl, cycloalkyl, saturated or partially saturated heterocycle, heteroaryl, alkyl, alkenyl, alkynyl, arylalkyl, arylalkenyl, arylakynyl, heteroarylalkyl, heteroarylakenyl, heteroarylalkynyl, cycloalkylalkyl, heterocycloalkyl, hydroxyalkyl, aminoalkyl, carboxyalkyl, alkoxyalkyl, nitro, amino, ureido, cyano, acylamino, amide, thiol, acyloxy, azido, carboxy, carbonylamido and alkylthiol; or R₉ and R₁₀ and R₁₁ are taken together with the carbon atoms to which they are attached to form a carbocycle to a heterocycle;

with the provisos that;
1) when HET is (iii),
   a) R₁ is H, X is O or CH₂ and R₂ and R₃ together from —CH═CH—CH═CH—, R₅–R₁₃ are not all H;
   b) R₁ is Et and R₂ and R₃ together form —CH═CH—CH═CH—, X is not —NEt; or
   c) R₁ is H and X is O, R₅–R₁₃ are not all H; or
2) when Het is (iv) and R₁ is H or alkyl, R₂–R₁₃ are not all H.

35. A method for treating, or ameliorating neuronal loss following global and focal ischemia; treating or ameliorating neurodegenerative conditions; treating or ameliorating pain of tinnitus; treating or ameliorating manic depression; providing local anesthesia; or treating arrhythmias, or treating convulsions, comprising administering to a mammal in need of such treatment an effective amount of a compound formula:

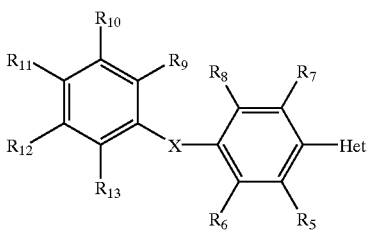

or a pharmaceutically acceptable salt, prodrug or solvate thereof, wherein:

Het is a heteroaryl selected from the group consisting of (iii)
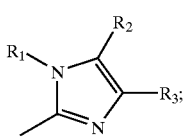

(iv)
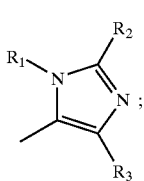

(v)
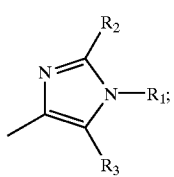

(vii)
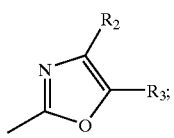

(viii)
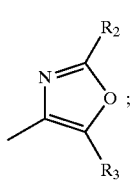

(ix)
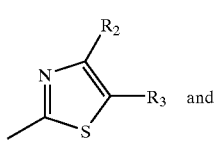 and (x)
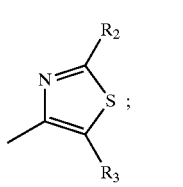

$R_1$ is selected from the group consisting of hydrogen, alkyl, cycloalkyl, aryl, aralkyl, heteroaryl, $C(O)R_{14}$, $CH_2C(O)R_{14}$, $S(O)R_{14}$, and $SO_2R$–all of which may be optionally substituted; $R_2$ and $R_3$ are independently selected from the group consisting of hydrogen, alkyl, cycloalkyl, alkenyl, alkynyl, haloalkyl, aryl, aminoalkyl, hydroxyalkyl, alkoxyalkyl, alkylthio, alkylsulfinyl, alkylsulfonyl, carboxyalkyl, cyano, amino, alkylamino, aminocarbonyl, alkylaminocarbonyl, arylaminocarbonyl, aralkylaminocarbonyl, alkylcarbonylamino, arylcarbonylamino, aralkylcarbonylamino, alkylcarbonyl, heterocyclocarbonyl, aminosulfonyl, alkylaminosulfonyl, alkylsulfonyl, and heterocyclosulfonyl, or the R groups in adjacent carbon atoms can be taken together with the carbon atoms to which they are attached to form a carbocycle or a heterocycle;

$R_5$, $R_6$, $R_7$, $R_8$, $R_9$, $R_{10}$, $R_{11}$, $R_{12}$, and $R_{13}$ are independently selected from the group consisting of hydrogen, halo, haloalkyl, aryl, cycloalkyl, saturated or partially unsaturated heterocycle, heteroaryl, alkyl, alkenyl, alkynyl, arylalkyl, arylakenyl, arylalkynyl, heteroarylalkyl, heteroarylalkenyl, heteroarylalkynyl, cycloalkylalkyl, heterocycloalkyl, hydroxyalkyl, aminoalkyl, carboxyalkyl, alkoxyalkyl, nitro, amino, ureido, cyano, acylamino, amide, hydroxy, thiol, acyloxy, azido, alkoxy, carboxy, carbonylamido and alkylthiol; or $R_9$ and $R_{10}$ or $R_{10}$ and $R_{11}$ are taken together with the carbon atoms to which they are attached to form a carbocycle or a heterocycle;

$R_{14}$ is selected from the group consisting of amino, alkyl, alkenyl, alkynyl, $OR_{16}$, alkylamino, dialkylamino, alkenylamino, cycloalkyl, aralkyl, aryl, heteroaryl, arylalkenyl, arylalkynyl, arylalkylamino, dialkylaminoalkenyl, heterocycle, heterocycloalkylamino, and cycloalkylalkylamino, all of which can be optionally substituted; wherein $R_{16}$ is selected from the group consisting of hydrogen, optionally substituted alkyl, and an alkalimetal; and X is one of O, S, $NR_{15}$, $CH_2$, $NR_{15}C(O)$, or $C(O)NR_{15}$, wherein $R_{15}$ is hydrogen, alkyl or cycloalkyl.

36. The method of claim 35, wherein:

$R_2$ and $R_3$ are independently selected from the group consisting of hydrogen, cycloalkyl, alkenyl, alkynyl, haloalkyl, aminoalkyl, hydroxyalkyl, alkoxyalkyl, alkylthio, alkylsulfinyl, alkylsulfonyl, carboxyalkyl, cyano, alkylamino, aminocarbonyl, alkylaminocarbonyl, arylaminocarbonyl, aralkylaminocarbonyl, arylcarbonylamino, aralkylcarbonylamino, alkylcarbonyl, heterocyclocarbonyl, aminosulfonyl, alkylaminosulfonyl, alkylsulfonyl, and heterocyclosulfonyl, or the R groups on adjacent carbon atoms can be taken together with the carbon atoms to which they are attached to form a heterocycle; and $R_5$, $R_6$, $R_7$, $R_8$, $R_9$, $R_{10}$, $R_{11}$, $R_{12}$, and $R_{13}$ are independently selected from the group consisting of hydrogen, halo, haloalkyl, aryl, cycloalkyl, saturated or partially unsaturated heterocycle, heteroaryl, alkyl, alkenyl, alkynyl, arylalkyl, arylalkenyl, arylalkynyl, heteroarylalkyl, heteroarylalkenyl, heteroarylalkynyl, cycloalkylalkyl, heterocycloalkyl, hydroxyalkyl, aminoalkyl, carboxyalkyl, alkoxyalkyl, nitro, amino, ureido, cyano, acylamino, amide, thiol, acyloxy, azido, carboxy, carbonylamido and alkylthiol; or $R_9$ and $R_{10}$ or $R_{10}$ and $R_{11}$ are taken together with the carbon atoms to which they are attached to form a carbocycle or a heterocycle;

with the provisos that:

1) when Het is (iii),
   a) $R_1$ is H, X is O or $CH_2$ and $R_2$ and $R_3$ together form —CH=CH—CH=CH—, $R_5$–$R_{13}$ are not all H;

b) $R_1$ is Et and $R_2$ and $R_3$ together form —CH=CH—CH=CH—, X is not —NEt; or c) $R_1$ is H and X is O, $R_5$–$R_{13}$ are not all H; or 2) when Het is (iv) and $R_1$ is H or alkyl, $R_2$–$R_{13}$ are not all H.

37. The method of claim 35, wherein the method is for treating or ameliorating pain and said pain is one of neuropathic pain, surgical pain or chronic pain.

38. A method of alleviating seizure activity in an animal subject, comprising administering to said animal in need of such treatment an effective amount of a compound of formula:

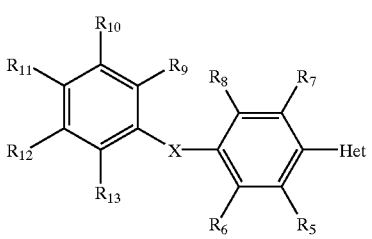

I or a pharmaceutically acceptable salt, prodrug or solvate thereof, wherein:

Het is a heteroaryl selected from the group consisting of

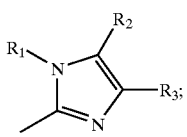
(iii)

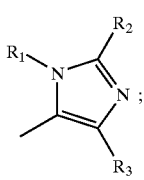
(iv)

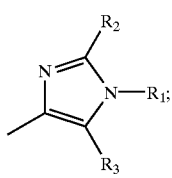
(v)

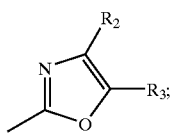
(vii)

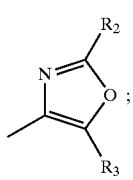
(viii)

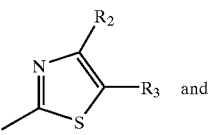
(ix)

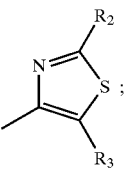
(x)

$R_1$ is selected from the group consisting of hydrogen, alkyl, cycloalkyl, aryl, aralkyl, heteroaryl, $C(O)R_{14}$, $CH_2C(O)R_{14}$, $S(O)R_{14}$, and $SO_2R_{14}$ all of which may be optionally substituted;

$R_2$ and $R_3$ are independently selected from the group consisting of hydrogen, alkyl, cycloalkyl, alkenyl, alkynyl, haloalkyl, aryl, aminoalkyl, hydroxyalkyl, alkoxyalkyl, alkylthio, alkylsulfinyl, alkylsulfonyl, carboxyalkyl, cyano, amino, alkylamino, aminocarbonyl, alkylaminocarbonyl, arylaminocarbonyl, aralkylaminocarbonyl, alkylcarbonylamino, arylcarbonylamino, aralkylcarbonylamino, alkylcarbonyl, heterocyclocarbonyl, aminosulfonyl, alkylaminosulfonyl, alkylsulfonyl, and heterocyclosulfonyl, or the R groups in adjacent carbon atoms can be taken together with the carbon atoms to which they are attached to form a carbocycle or a heterocycle;

$R_5$, $R_6$, $R_7$, $R_8$, $R_9$, $R_{10}$, $R_{11}$, $R_{12}$, and $R_{13}$ are independently selected from the group consisting of hydrogen, halo, haloalkyl, aryl, cycloalkyl, saturated or partially unsaturated heterocycle, heteroaryl, alkyl, alkenyl, alkynyl, arylalkyl, arylalkenyl, arylalkynyl, heteroarylalkyl, heteroarylalkenyl, heteroarylalkynyl, cycloalkylalkyl, heterocycloalkyl, hydroxyalkyl, aminoalkyl, carboxyalkyl, alkoxyalkyl, nitro, amino, ureido, cyano, acylamino, amide, hydroxy, thiol, acyloxy, azido, alkoxy, carboxy, carbonylamido and alkylthiol; or $R_9$ and $R_{10}$ or $R_{10}$ and $R_{11}$ are taken together with the carbon atoms to which they are attached to form a carbocycle or a heterocycle;

$R_{14}$ is selected from the group consisting of amino, alkyl, alkenyl, alkynyl, $OR_{16}$, alkylamino, dialkylamino, alkenylamino, cycloalkyl, aralkyl, aryl, heteroaryl, arylalkenyl, arylalkynyl, arylalkylamino, dialkylaminoalkenyl, heterocycle, heterocycloalkylamino, and cycloalkylalkylamino, all of which can be optionally substituted; wherein $R_{16}$ is selected from the group consisting of hydrogen, optionally substituted alkyl, and an alkalimetal; and X is one of O, S, $NR_{15}$, $CH_2$, $NR_{15}C(O)$, or $C(O)NR_{15}$, wherein $R_{15}$ is hydrogen, alkyl or cycloalkyl.

39. The method of claim 38, wherein:

$R_2$ and $R_3$ are independently selected from the group consisting of hydrogen, cycloalkyl, alkenyl, alkynyl, haloalkyl, aminoalkyl, hydroxyalkyl, alkoxyalkyl, alkythio, alkylsulfinyl, alkysulfonyl, carboxyalkyl, cyano, alkylamino, aminocarbonyl, alkulaminocarbonyl, arylaminocarbonyl, aralkylaminocarbonyl, arylcarbonylamino, aralkylcarbonylamino, alkylcarbonyl, heterocyclocarbonyl, aminosulfonyl, alkylaminosulfonyl, alkylsulfonyl, and heterocyclosulfonyl, or the R groups on adjacent carbon atoms can be taken together with the carbon atoms to which they are attached to form a heterocycle; and $R_5$, $R_6$, $R_7$, $R_8$, $R_9$, $R_{10}$, $R_{11}$, $R_{12}$ and $R_{13}$ are independently selected from the group consisting of hydrogen, halo, haloalkyl, aryl, cycloalkyl, saturated or partially unsaturated heterocycle, heteroaryl, alkyl, alkenyl, alkynyl, arylalkyl, arylakenyl, arylakynyl, heteroaryalkyl, heteroarylakenyl, heterozrylalkynyl, cycloalkylakyl, heterocycloalkyl, hydroxyalkyl, aminoalkyl, carboxyalkyl, alkoxyalkyl, nitro, amino, ureido, cyano, acylamino, amide, thiol, acyloxy, azido, carboxy, carbonylamido and alkylthiol; or $R_9$ or $R_{10}$ and $R_{11}$ are taken together with the carbon atoms to which they are attached to form a carbocycle or a heterocycle;

with the provisos that:
1) when Het is (iii),
   a) $R_1$ is H, X is O or $CH_2$ and $R_2$ and $R_3$ together form —CH=CH—CH=CH—, $R_5$–$R_{13}$ are not all H;
   b) $R_1$ is Et and $R_2$ and $R_3$ together form —CH=CH—CH=CH—, X is not —NEt; or
   c) $R_1$ is H and X is O, $R_5$–$R_{13}$ are not all H; or
2) when Het is (iv) and $R_1$ is H or alkyl, $R_2$–$R_{13}$ are not all H.

* * * * *